US011590244B2

(12) United States Patent
Rajagopalan et al.

(10) Patent No.: US 11,590,244 B2
(45) Date of Patent: *Feb. 28, 2023

(54) METHODS FOR RENAL FUNCTION DETERMINATION

(71) Applicant: MediBeacon Inc., St. Louis, MO (US)

(72) Inventors: Raghavan Rajagopalan, Solon, OH (US); Richard B. Dorshow, St. Louis, MO (US); William L. Neumann, St. Louis, MO (US); Thomas E. Rogers, St. Louis, MO (US); Martin P. Debreczeny, Berkeley, CA (US)

(73) Assignee: MediBeacon Inc., St. Louis, MO (US)

( * ) Notice: Subject to any disclaimer, the term of this patent is extended or adjusted under 35 U.S.C. 154(b) by 1070 days.

This patent is subject to a terminal disclaimer.

(21) Appl. No.: 16/171,695

(22) Filed: Oct. 26, 2018

(65) Prior Publication Data
US 2019/0125902 A1 May 2, 2019

Related U.S. Application Data

(60) Provisional application No. 62/577,951, filed on Oct. 27, 2017.

(51) Int. Cl.
A61K 51/00 (2006.01)
A61K 49/00 (2006.01)
A61M 5/00 (2006.01)
A61B 5/00 (2006.01)
A61B 5/20 (2006.01)
C09B 57/00 (2006.01)
A61P 13/12 (2006.01)
C09K 11/06 (2006.01)
C07D 241/26 (2006.01)

(52) U.S. Cl.
CPC ........ A61K 49/0021 (2013.01); A61B 5/0071 (2013.01); A61B 5/201 (2013.01); A61K 49/0004 (2013.01); A61K 49/0054 (2013.01); A61M 5/007 (2013.01); A61P 13/12 (2018.01); C09B 57/00 (2013.01); C09K 11/06 (2013.01); C07D 241/26 (2013.01); C09K 2211/1077 (2013.01)

(58) Field of Classification Search
CPC ............ A61K 49/0004; A61K 49/0021; A61K 49/0054; A61P 13/12; A61B 5/0071; A61B 5/201; A61M 5/007; C09B 57/00; C09K 11/06; C09K 2211/1077; C07D 241/26
See application file for complete search history.

(56) References Cited

U.S. PATENT DOCUMENTS

| 8,115,000 | B2 | 2/2012 | Rajagopalan et al. |
| 8,313,729 | B2 | 11/2012 | Neumann et al. |
| 8,664,392 | B2 | 3/2014 | Rajagopalan et al. |
| 8,697,033 | B2 | 4/2014 | Poreddy et al. |
| 8,722,685 | B2 | 5/2014 | Rajagopalan et al. |
| 8,778,309 | B2 | 7/2014 | Rajagopalan et al. |
| 9,005,581 | B2 | 4/2015 | Poreddy et al. |
| 9,114,160 | B2 | 8/2015 | Rajagopalan et al. |
| 9,283,288 | B2 | 3/2016 | Dorshow et al. |
| 9,376,399 | B2 | 6/2016 | Rajagopalan et al. |
| 9,480,687 | B2 | 11/2016 | Rajagopalan et al. |
| 10,264,977 | B2 | 4/2019 | Heinrich et al. |
| 2003/0236452 | A1 | 12/2003 | Melker et al. |
| 2006/0095102 | A1 | 5/2006 | Perez |
| 2008/0281173 | A1 | 11/2008 | Esenaliev et al. |
| 2009/0010851 | A1 | 1/2009 | Rajagopalan et al. |
| 2010/0010223 | A1 | 1/2010 | Dorshow |
| 2010/0105899 | A1 | 4/2010 | Neumann et al. |
| 2011/0250140 | A1 | 10/2011 | Poreddy et al. |
| 2013/0116512 | A1 | 5/2013 | Imran |
| 2015/0306486 | A1 | 10/2015 | Logan et al. |

FOREIGN PATENT DOCUMENTS

| WO | 2006071759 A2 | 6/2006 |
| WO | 2007149479 A1 | 12/2007 |
| WO | 2008108944 A2 | 9/2008 |
| WO | 2015070256 A1 | 5/2015 |
| WO | 2016183351 A1 | 11/2016 |

OTHER PUBLICATIONS

Dorshow et al. (Sci. Reports 2017, pp. 1-8).*
Clinical study NCT20772276 Jul. 27, 2016.*
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine And Urea Clearances In Newborn Infants," J. Physiol., vol. 106, (1947), pp. 431-439.
Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.
Friedman et al., "A comparison of the renal clearances of allantoin and inulin in man," Fed. Proc., vol. 7, No. 1 Pt 1, (1948), 1 page.

(Continued)

Primary Examiner — Michael G. Hartley
Assistant Examiner — Melissa J Perreira
(74) Attorney, Agent, or Firm — Armstrong Teasdale LLP

(57) ABSTRACT

The present disclosure relates to systems and methods for determining the renal glomerular filtration rate or assessing the renal function in a patient in need thereof. The method includes administering a pyrazine compound of Formula I to a patient and monitoring the rate in which the kidneys of the patient eliminate the pyrazine from the systemic circulation of the patient. The pyrazine compound fluoresces when exposed to electromagnetic radiation which is detected using one or more sensors. The rate in which the fluorescence decreases in the patient is used to calculate the renal glomerular filtration rate in the patient.

38 Claims, 19 Drawing Sheets

(56) References Cited

OTHER PUBLICATIONS

Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.
Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.
Nagpal et al., "Combined Fluorescein, Indocyanine angiography and Optical Coherent Tomography Using Spectralis," Rajasthan Journal Of Ophthalmology, (2011), 8 pages.
Navar et al., "Distal Tubular Feedback in the Autoregulation of Single Nephron Glomerular Filtration Rate," J. Clin. Invest., vol. 53, (1974), pp. 516-525.
Nicholson et al., "Renal Function as Affected by Experimental Unilateral Kidney Lesions: I. Nephrosis Due to odium Rartrate," J. Exp. Med., vol. 68, (1938), pp. 439-456.
Pill et al., "Fluorescein-labeled Sinistrin as Marker of Glomerular Filtration Rate," European Journal of Medicinal Chemistry, vol. 40, (2005), pp. 1056-1061.
Poujeol et al., "Glomerular Filtration Rate and Microsphere Distributions in Single Nephron of Rat Kidney," Pflugers Arch., vol. 357, (1975), pp. 291-301.
Robson et al., "The Determination of the Renal Clearance of Inulin in Man," Q. J. Exp. Physiol., vol. 35, (1949), pp. 111-134.
Schock-Kusch et al., "Transcutaneous measurement of glomerular filtration rate using FITC-sinistrin in rats," Nephrol Dial Transplant, vol. 24, (2009), pp. 2997-3001.
Shannon et al., "The Renal Excretion of Inulin and Creatinine by the Anaesthetized Dog and the Pump-Lung-Kidney Preparation", J. Physiol., vol. 98, (1940), pp. 97-108.
Yu et al., "Rapid determination of renal filtration function using an optical ratiometric imaging approach," Am. J. Physiol. Renal. Physiol., vol. 292, (2007), pp. F1873-F1880.
International Search Report received for PCT Patent Application No. PCT/US2019/013784, dated May 7, 2019, 3 pages.
International Preliminary Report on Patentability received for PCT Patent Application No. PCT/US2019/013784, dated Jul. 30, 2020, 8 pages.
Andreucci et al., "Side Effects of Radiographic Contrast Media: Pathogenesis, Risk Factors, and Prevention", BioMed Research International, 2014, vol. 2014, Article ID 741018, 20 pages.
Berge et al., "Pharmaceutical Salts", Journal of Pharmaceutical Sciences, Jan. 1977, vol. 66, No. 1, pp. 1-19.
Bugaj et al., "Initial Formal Toxicity Evaluation Of APC-2, a Novel Fluorescent Tracer Agent for Real-Time Measurement of Glomerular Filtration Rate in Preparation for a first-in-man clinical trial", SPIE, vol. 8956, Mar. 5, 2014, 15 pages.
Bugaj et al., "Pre-clinical toxicity evaluation of MB-102, a novel fluorescent tracer agent for real-time measurement of glomerular filtration rate", Regulatory Toxicology and Pharmacology, Jun. 2015, vol. 72, Issue 1, pp. 26-38.
Dorshow et al., "New optical proves for continuous monitoring of renal function", SPIE, Feb. 22, 2008, 11 pages.
National Kidney Foundation, "What You Should Know About Albuminuria (Proteinuria)", retrieved from https://www.kidney.org/atoz/content/proteinuriawyska, Aug. 12, 2016, pp. 1-3.
Poreddy et al., "Development of fluorescent tracers for the real-time monitoring of renal function", SPIE, Feb. 11, 2011, 7 pages.
Poreddy et al., "Exogenous fluorescent tracer agents based on pegylated pyrazine dyes for real-time point-of-care measurement of glomerular filtration rate", Bioorganic & Medicinal Chemistry, 2012, vol. 20, pp. 2490-2497.
Rajagopalan et al., "Hydrophilic Pyrazine Dyes as Exogenous Fluorescent Tracer Agents for Real-Time Point-of-Care Measurement of Glomerular Filtration Rate", Journal of Medicinal Chemistry, Jun. 13, 2011, vol. 54, pp. 5048-5058.

Solomon, Richard, "The role of osmolality in the incidence of contrast-induced nepthropathy: A systematic review of angiographic contrast media in high risk patients", Kidney International, 2005, vol. 68, pp. 2256-2263.
Traynor et al., "How to measure renal function in clinical practice", BMJ, Oct. 7, 2006, vol. 333, pp. 733-737.
International Search Report and Written Opinion for PCT/US2018/057743, dated Jan. 15, 2019, 9 pages.
Arana et al., "Dual Blockade of Endothelin a Receptor (ETA) and Sodium-Glucose Cotransporter 2 (SGLT2) to Prevent Diabetic Kidney Disease Progression on a Type 2 Murine Model", ERA-EDTA Meeting 2021, conference abstract FC088 NDT, vol. 36 (Supplement 1), May 2021, 2 pages.
Bugaj et al., "Pre-clinical toxicity evaluation of MB-102, a novel fluorescent tracer agent for real-time measurement of glomerular filtration rate", Regulatory Toxicology and Pharmacology, 2015, vol. 72, pp. 26-38.
Bugaj et al., "Initial Formal Toxicity Evaluation of APC-2, a Novel Fluorescent Tracer Agent for Real-Time Measurement of Glomerular Filtration Rate in Preparation for a first-in-man clinical trial", Proc. of SPIE vol. 8956, (2014), pp. 895601-1-8950601-15.
Burmakin et al., "Pharmacological HIF-PHD inhibition reduces renovascular resistance and increases glomerular filtration by stimulating nitric oxide generation", Acta Physiologica, 2021;00:e13668, https://doi.org/10.1111/apha.13668, 14 pages.
Chinen et al., "Fluorescence-enhanced europium complexes for the assessment of renal function", Molecular Probes for Biomedical Applications II, Progress in Biomedical Optics and Imaging, Proc. of SPIE vol. 6867, (2008), pp. 68670B-68670B.
Chinen et al., "Fluorescence-enhanced Europium-Diethylenetriaminepentaacetic (DTPA)-Monoamide complexes for the Assessment of Renal Function", Journal of Medicinal Chemistry, 2008, vol. 51, 957-962.
Dalmasso et al., "Intrarenal Renin Angiotensin System Imbalance During Postnatal Life Is Associated With Increased Microvascular Density in the Mature Kidney", Frontiers in Physiology, Sep. 2020, vol. 11, Article 1046, pp. 1-18.
Debreczeny et al., "Development and clinical trial results of a prototype device for trans-cutaneous monitoring of kidney function", Reporters, Markers, Dyes, Nanoparticles, and Molecular Probes for Biomedical Applications IX, Proc. of SPIE vol. 10079, (2017), pp. 10079K-1-10079K12.
Debreczeny et al., "Human skin autofluorescence decay as a function of irradiance and skin type", Optical Interactions with Tissue and Cells XXII, Proc. of SPIE vol. 7897, (2011), pp. 78971T-1-78971T-11.
Debreczeny et al., "Transdermal optical renal function monitoring in humans: development, verification, and validation of a prototype device", Journal of Biomedical Optics, 2018, vol. 23, No. 5, pp. 057003-1-057003-9.
De Chiara et al., "Tubular Epithelial Cell Polyploidy is Essential to Survive AKI but it Contributes to CKD Progression", ERA-EDTA Meeting 2021, conference abstract FC041 NDT, vol. 36 (Supplement 1), May 2021, 1 page.
Dorshow et al., "Latest Results from the On-going Clinical Studies Utilizing the Novel Fluorescent Tracer Agent MB-102 for Transdermal Glomerular Filtration Rate Measurement", MediBeacon Inc., St. Louis University, Washington University, presented at 23rd International Conference on Advances in Critical Care Nephrology, San Diego, CA, 2018-AKI-CRRT Poster, 1 page.
Dorshow et al., "Application of Fluorescent Tracer Agent Technology to Point-of-Care Gastrointestinal Permeability Measurement", Reporters, Markers, Dyes, Nanoparticles, and Molecular Probes for Biomedical Applications VIII, Proceedings of SPIE vol. 9723, (2016), pp. 97230A-1-97230A-4.
Dorshow et al., "Clinical Study Results of a Real-Time Point-of-Care Glomerular Filtration Rate Measurement", presented at the American Society of Nephrology Kidney Week Meeting, New Orleans, LA, 2017, 12 pages.
Dorshow et al., "Initial Clinical Trial Results of a Real-Time Point-of-Care Glomerular Filtration Rate Measurement Utilizing a

(56) References Cited

OTHER PUBLICATIONS

Novel Fluorescent Tracer Agent", presented at the American Society of Nephrology Kidney Week Meeting, San Diego, CA, 2015, 1 page.

Dorshow et al., "Measurement of gut permeability using fluorescent tracer agent technology", Scientific Reports, 2017, vol. 7: 10888, 8 pgs.

Dorshow et al., "New optical probes for the continuous monitoring of renal function", Molecular Probes for Biomedical Applications II, Proc. of SPIE vol. 6867, (2008), pp. 68670C-1-68670C-11.

Dorshow et al., "Next tier in vitro and in vivo nonclinical studies further elucidating the safety and toxicity profile of MB-102, a novel fluorescent tracer agent for measurement of glomerular filtration rate", Regulatory Toxicology and Pharmacology, 2019, vol. 107, No. 104417, 11 pages.

Dorshow et al., "Noninvasive point-of-care measurement of gastrointestinal permeability", Proc. of SPIE, 2019, vol. 10893, pp. 1089307-1-1089307-7.

Dorshow et al., "Real-time point-of-care measurement of impaired renal function in a rat acute injury model employing exogenous fluorescent tracer agents", presented at the BiOS Symposium, Photonics West, San Francisco, CA, 2013, 1 page.

Dorshow et al., "Real-time point-of-care measurement of impaired renal function in a rat acute injury model employing exogenous fluorescent tracer agents", Reporters, Markers, Dyes, Nanoparticles, and Molecular Probes for Biomedical Applications V, Proc. of SPIE vol. 8596, 85960Z (2013), 1 page.

Dorshow, R., "Kidney Function Monitoring: Pathway to the Future" in Renal Business Today, Nov. 2013, 2 pages.

Dorshow et al., "Results of the first-in-human clinical trial for MB-102, a novel fluorescent tracer agent for real-time measurement of glomerular filtration rate", Proc. of SPIE vol. 9339, (2015), pp. 933906-1-933906-4.

Dorshow et al., "Transdermal fluorescence detection of a dual fluorophore system for noninvasive point-of-care gastrointestinal permeability measurement", Biomedical Optics Express, Oct. 1, 2019, vol. 10, No. 10, pp. 5103-5116.

Garcia-Arroyo et al., "Osthol Ameliorates Kidney Damage and Metabolic Syndrome Induced by a High-Fat/High-Sugar Diet", International Journal of Molecular Sciences, 2021, vol. 22, No. 2431, 17 pages.

Jang et al., "MB-102 Clearance During Ex Vivo Continuous Renal Replacement Therapy", Department of Clinical Pharmacy, College of Pharmacy, University of Michigan, presented at 23rd International Conference on Advances in Critical Care Nephrology, San Diego, CA, 2018-AKI-CRRT Poster, 1 page.

Kougioumtzidou et al., "Reduction in Proximal Tubular Secretion Precedes Reduction in Glomerular Filtration Rate in the Adenine-Induced CKD Model", Am Soc. Nephrol Kidney Week Abstract Supplement: PO2361, 2020, 2 pages.

Li et al., "Proximal Tubule-Specific Deletion of Angiotensin II Type 1a Receptors in the Kidney Attenuates Circulating and Intratubular Angiotensin II-Induced Hypertension in PT-Agtrla-/- Mice", Hypertension, Apr. 2021, vol. 77, pp. 1285-1298.

Martino et al., "Endothelial SOCS3 Maintains Homeostasis and Promotes Survival in Endotoxemic Mice", JCI Insight, 2021, vol. 6, No. 14, e147280, 22 pages.

Pirie et al., "MB-102: A Novel Tracer Agent for Canine Ocular Angiography", MediBeacon Inc., College of Veterinary Medicine, Michigan State University, East Lansing MI, Presented at American College of Veterinary Ophthalmologists 2019 Annual Conference, Maui, HI, 2019, 1 page.

Pirie et al., "Effectiveness of MB-102, a novel fluorescent tracer agent, for conducting ocular angiography in dogs", American Journal of Veterinary Research, May 2020, vol. 81, No. 5, pp. 428-436.

Poreddy et al., "Exogenous fluorescent tracer agents based on pegylated pyrazine dyes for real-time point-of-care measurement of glomerular filtration rate", Bioorg. Med. Chem. 2012, vol. 20, pp. 2490-2497.

Poreddy et al., "A highly efficient method for the N-alkylation of amino pyrazines: synthesis of hydrophilic red fluorescent dyes", Synthesis 14, (2010), pp. 2383-2392.

Poreddy et al., "Development of fluorescent tracers for the real-time monitoring of renal function", Reporters, Markers, Dyes, Nanoparticles, and Molecular Probes for Biomedical Applications, Proc. of SPIE vol. 7910, (2011), pp. 791010-1-791010-7.

Poreddy et al., "N-Alkylated aminopyrazines for use as hydrophilic optical agents", Reporters, Markers, Dyes, Nanoparticles, and Molecular Probes for Biomedical Applications, Proc. of SPIE vol. 7190, (2009), pp. 71900P-1-71900P-10.

Rajagopalan et al., "Exogenous fluorescent agents for the determination of glomerular filtration rate", in Chronic Kidney Disease, edited by M. Gooz (Intech, Rijeka, Croatia 2012), Chapter 15, p. 251-260.

Rajagopolan et al., "Hydrophilic pyrazine dyes as exogenous fluorescent tracer agents for real-time point-of-care measurement of glomerular filtration rate", J. Med. Chem., 2011, vol. 54, pp. 5048-5058.

Rudloff et al., "Fetuin-A is a HIF target that safeguards tissue integrity during hypoxic stress", Nature Communications, 2021, vol. 12, No. 549, 16 pages.

Sano et al., "Glomerular hyperfiltration with hyperglycemia in the spontaneously diabetic Torii (SDT) fatty rat, an obese type 2 diabetic model", Physiol. Res., 2021, vol. 70, pp. 45-54.

Sano et al., "Glomerular hyperfiltration with hyperglycemia in the Spontaneously Diabetic Torii (SDT) fatty rat, an obese type 2 diabetic model", Physiological Research Pre-Press Article, Jan. 2021, https://www.biomed.cas.cz/physiolres/pdf/prepress/934533.pdf, 28 pages.

Scuron et al., "The PI3Kδ inhibitor parsaclisib ameliorates pathology and reduces autoantibody formation in preclinical models of systemic lupus erythematosus and Sjogren's syndrome", International Immunopharmacology, 2021, vol. 98, No. 107904, 11 pages.

Shieh et al., "Characterization of MB-102, a New Fluorescent Tracer Agent for Point-of-Care Renal Function Monitoring", Journal of Pharmaceutical Sciences, 2020, vol. 109, pp. 1191-1198.

Shieh et al., "Clinical analysis and quantitation of MB-102, a novel fluorescence tracer agent, in human plasma", The Analytical Methods, 2018, vol. 10, pp. 2376-2383.

Shultz et al., "Modeling of transdermal fluorescence measurements from first-in-human clinical trials for renal function determination using fluorescent tracer agent MB-102", Proc. of SPIE vol. 10079, (2017), pp. 1007901-1-1007901-10.

Sorrano et al., "Acute Kidney Injury Results in Long-Term Diastolic Dysfunction That Is Prevented by Histone Deacetylase Inhibition", JACC Basic to Translational Science, 2021, vol. 6, No. 2, pp. 119-133.

Terker et al., "Activation of hypoxia-sensing pathways promotes renal ischemic preconditioning following myocardial infarction", American Journal of Physiology Renal Physiology, Feb. 1, 2021, vol. 320, pp. F569-F577.

Uijl et al., "No evidence for brain renin-angiotensin system activation during DOCA-salt hypertension", Clinical Science, downloaded Jan. 11, 2021, 28 pages.

Waller et al., "A dose-escalating toxicology study of the candidate biologic ELP-VEGF", Scientific Reports, (2021), vol. 11, No. 6216 | https://doi.org/10.1038/s41598-021-85693-6, 15 pages.

Yang et al., "Hyperuricemia has Vasoactive Effects in Cholesterol Crystal-Induced Acute Kidney Injury", ERA-EDTA Meeting 2021, conference abstract FC003 NDT, vol. 36 (Supplement 1), May 2021, 1 page.

Zhuang et al., "The AGE receptor, OST48 drives podocyte foot process effacement and basement membrane expansion (alters structural composition)", Endocrinology, Diabetes & Metabolisim, May 22, 2021, 15 pages.

Dorshow et al., "Results of the first-in-human clinical trial for MB-102, a novel fluorescent tracer agent for real-time measurement of glomerular filtration rate", Progress in Biomedical Optics and Imaging, SPIE—International Society for Optical Engineering, Bellingham, WA, US, vol. 9339, Mar. 12, 2015, pp. 933906-933906.

Debreczeny et al., "Development and clinical trial results of a prototype device for trans-cutaneous monitoring of kidney func-

(56) References Cited

OTHER PUBLICATIONS tion", Progress in Biomedical Optics and Imaging, SPIE—International Society for Optical Engineering, Bellingham, WA, US, vol. 10079, Feb. 21, 2017, pp. 100790K-100790K.
Debreczeny et al., "Development and clinical trial results of a prototype device for trans-cutaneous monitoring of kidney function", Feb. 21, 2017, p. 1, retrieved from the Internet on Jun. 7, 2021: URL:https://www.spiedigitallibrary.org/conference-proceedings-of-spie/10079/100790K/Development-and-clinical-trial-results-of-a-prototypedevice-for/10.1117/12.2250975.full?SSO=1.
Abellan et al., "A Novel Model of Chronic Kidney Disease in Rats: Dietary Adenine in Combination with Unilateral Nephrectomy", (2019) Kidney Diseases, 9 pages.
Black et al., "Divergent effects of AKI to CKD models on inflammation and fibrosis", Am. J. of Physiology Renal Physiology, 2018, vol. 314, pp. F1107-F1118.
Black et al., "Myeloid Ferritin Heavy Chain Protects Against Ferroptosis in Ischemic AKI", Am. Soc. Nephrol. Kidney Week Abstract Supplement: TH-PO039, 2019, 2 pages.
Chang-Panesso et al., "Meis1 is specifically upregulated in kidney myofibroblasts during aging and injury but is not required for kidney homeostasis or fibrotic response", American Journal of Physiology Renal Physiol. Mar. 28, 2018, vol. 315, pp. F275-F290.
Chiara et al., "Polyploidization Is Essential to Survive AKI but It Contributes to CKD Development", Am. Soc. Nephrol. Kidney Week Abstract Supplement: TH-OR011, 2019, 2 pages.
Cippa et al., "A late B lymphocyte action in dysfunctional tissue repair following kidney injury and transplantation", Nature Communications, 2019, 11 pages.
Cunningham, Jr. et al., "AT1-AA (Angiotensin II Type 1 Receptor Agonistic Autoantibody) Blockade Prevents Preeclamptic Symptoms in Placental Ischemic Rats", Hypertension, American Heart Association, 2018, pp. 886-893.
Daya et al., "A Novel and Reproducible Model of CKD-Induced Vascular Calcification in Mice", Am. Soc. Nephrol. Kidney Week Abstract Supplement: SA-PO336, 2019, 2 pages.
Dizin et al., "Time-course of sodium transport along the nephron in nephrotic syndrome: The role of potassium", The FASEB Journal, 2019, 17 pages.
Eriguchi et al., "The Absence of the ACE N-Domain Decreases Renal Inflammation and Facilitates Sodium Excretion during Diabetic Kidney Disease", J Am Soc Nephrol., 2018, vol. 29, pp. 2546-2561.
Geraci et al., "Combining new tools to assess renal function and morphology: a holistic approach to study the effects of aging and a congenital nephron deficit", Am J of Physiology Renal Physiology, May 10, 2017, vol. 313, pp. F576-F584.
Granqvist et al., "The Distribution Profile of Anti-Sense Oligonucleotides Indicates That Proximal Tubular Targets Should Be Prioritized in Renal Disease", J. Am. Soc. Nephrol, Kidney Week Abstract Supplement: SA-PO631, 2018, 2 pages.
Harwood et al., "Murine models of renal ischaemia reperfusion injury: An opportunity for refinement using non-invasive monitoring methods", Cold Spring Harbor Laboratory Dec. 19, 2019, 23 pages.
Katsyuba et al., "De novo NAD+ synthesis enhances mitochondrial function and improves health", Nature, 2018, vol. 563, No. 7731, 39 pages.
Khalaf et al., "Paraoxonase 1 Regulation of Renal Inflammation and Fibrosis in CKD", Am. Soc. Nephrol. Kidney Week Abstract Supplement, 2019, 2 pages.
Kruger et al., "SP327 Inhibition of p53 improves renal outcome in adenine crystal-induced nephropathy", Nephrology Dialysis Transplantation, vol. 34, Jun. 2019, 2 pages.
Kuriakose et al., "Patrolling monocytes promote the pathogenesis of early lupus-like glomerulonephritis", Journal of Clinical Investigation, Apr. 29, 2019, 16 pages.
Lazzeri et al., "Endocycle-related tubular cell hypertrophy and progenitor proliferation recover renal function after acute kidney injury", Nature Communications, 2018, vol. 9, No. 1344, 19 pages.

Lazzeri et al., "Endocycle-Mediated Hypertrophy and Progenitor Proliferation as Central Mechanisms of Response to AKI", Am. Soc. Nephrol. Kidney Week Abstract Supplement: SA-OR085, 2017, 2 pages.
Li et al., "Proximal Tubule-Specific Deletion of the NHE3 (Na+/H+ Exchanger 3) in the Kidney Attenuates Ang II (Angiotensin II)-Induced Hypertension in Mice", American Heart Association, Inc., 2019, vol. 30, pp. 526-535.
Machado et al., "Gli1+ Pericytes Are Required for AKI Recovery and Regulate Renal Function", Am. Soc. Nephrol. Kidney Week Abstract Supplement: SA-OR087, 2017, 2 pages.
Marschner et al., "Endogenous pentraxin 3 inhibits nephrocalcinosis and protects from hyperoxalluria-induced Chronic Kidney Disease", Nephrology Dialysis Transplantation, 2018, 3 pages.
Moggio et al., "Assessment of acute kidney injury in rhabdomyolytic mice by transcutaneous measurement of sinistrin excretion", Nephrol Dial Transplant, 2017, vol. 32, pp. 1167-1175.
Moonen et al., "Varying Nephrectomy Delay Time After Unilateral Ischemic Injury Allows Development of an Animal Model with a Controllable Degree of Renal Dysfunction", Am. Soc. Nephrol. Kidney Week Abstract Supplement: PUB-168, 2018, 2 pages.
Newsome et al., "Renal injury after uninephrectomy in male and female intrauterine growth-restricted aged rats", PLOS ONE, Mar. 7, 2019, 16 pages.
Niculovic et al., "Podocyte-Specific Sialylation-Deficient Mice Serve as a Model for Human FSGS", JASN, 2019, pp. 1021-1035.
Ougaard et al., "Inhibitors of the renin-angiotensin system ameliorates clinical and pathological aspects of experimentally induced nephrotoxic serum nephritis", Renal Failure, 2018, vol. 40, No. 1, pp. 640-648.
Ougaard et al., "Murine Nephrotoxic Nephritis as a Model of Chronic Kidney Disease", Department of Diabetes Complications Pharmacology, Novo Nordisk, Denmark; Department of Histology and Bioimaging, Novo Nordisk, Denmark; Department of Veterinary and Animal Sciences, University of Copenhagen, Denmark, 2018, 24 pages.
Paauw et al., "Exposure to placental ischemia impairs postpartum maternal renal and cardiac function in rats", Am J of Physiology Regul Integrative Comp Physiol, Feb. 2017, vol. 312, pp. R664-R670.
Peired et al., "Papillary renal cell carcinoma originates from a population of renal progenitor cells and is promoted by Acute Kidney Injury", Nephrology Dialysis Transplantation 33 (Supplemental 1), 2018, 1 page.
Rath et al., "Anti-Histone IGG attenuates CKD upon AKI related to postischemic tubular necrosis in mice", Nephrology Dialysis Transplatation 32 (Supplement 3), 2018, 1 page.
Rush et al., "Genetic Nrf2 Enhancement Increases Proteinuric Renal Injury", Am. Soc. Nephrol. Kidney Week Abstract Supplement: SA-PO815, 2018, 2 pages.
Sabapathy et al., "A Novel Hybrid Cytokine IL233 Mediates regeneration following Doxorubicin-Induced Nephrotoxic Injury", Scientific Reports, (2019), 9:3215, 12 pages.
Santeramo et al., "Human Kidney-Derived Cells Ameliorate Acute Kidney Injury Without Engrafting into Renal Tissue", Stem Cells Translational Medicine, 2017, 12 pages.
Scarfe et al., "Long-term outcomes in mouse models of ischemia-reperfusion induced acute kidney injury", American Journal of Physiology, Renal Physiology Aug. 14, 2019, pp. F1068-F1080.
Schumacher et al., "Compensatory mechanisms for methylglyoxal detoxification in experimental & clinical diabetes", Molecular Metabolism, 2018, 11 pages.
Sellmayr et al., "Macrophage polarization and granuloma formation in hyperuricemia-associated chronic kidney disease", Jun. 2018, 2 pages.
Shepard et al., "Renal Olfactory Receptor 1393 Contributes to the Progression of Type II Diabetes in a Diet-Induced Obesity Model", Am. Journal of Physiology Renal Physiology, 2019, vol. 316, pp. F372-F381.
Shi et al., "A Novel Targeting Strategy That Can Prevent Cholesterol Crystal Embolism-Induced AKI and Kidney Infarction", Am Soc. Nephrol Kidney Week Abstract Supplement, 2019, 2 pages.

(56) References Cited

OTHER PUBLICATIONS

Shi et al., "Extracellular DNA Drives Cholesterol Crystal Embolism-Related Tissue Injury", Am. Soc. Nephrol., Kidney Week Abstract Supplement: TH-OR001, 2018, 2 pages.
Soranno et al., "Long-Term Sequelae of Aki: A Year-Long Male and Female Murine Model", Am. Soc. Nephrol. Kidney Week Abstract Supplement: TH-OPO090, 2018, 2 pages.
Sorrano et al., "Matching Human Unilateral AKI, a Reverse Translational Approach to Investigate Kidney Recovery after Ischemia", JASN, 2019, 30(6) pp. 990-1005.
Steiger et al., "Anti-Transforming Growth Factor β IgG Elicits a Dual Effect on Calcium Oxalate Crystallization and Progressive Nephrocalcinosis-Related Chronic Kidney Disease", Frontiers in Immunology, Mar. 29, 2018, vol. 9, Article 619, 15 pages.
Steiger et al., "The Role of Renal Uric Acid Crystal Granulomas on CKD Progression in Mice and Humans", Am. Soc. Nephrol, Kidney Week, Abstract Supplement: TH-P0491, 2019, 2 pages.
Steubl et al., "Circulating cathepsin-S levels correlate with GFR decline and sTNFRI and sTNFR2 levels in mice and humans", Scientific Reports, 2017, vol. 7, No. 43538, 11 pages.
Sukumuran et al., "Liraglutide improves renal endothelial function in obese Zucker rats on a high-salt diet", Journal of Pharmacology and Experimental Therapeutics, Mar. 25, 2019, 3 pages.
Sukumaran et al., "Microangiography Reveals the Protective Role of Liraglutide on Renal Microvascular Impairment in Rats with Metabolic Syndrome", Am. Soc. Nephrol Kidney Week Abstract Supplement: TH-PO856, 2018, 2 pages.
Terstappen et al., "Prenatal Sildenafil Therapy Improves Cardiovascular Function in Fetal Growth Restricted Offspring of Dahl Salt-Sensitive Rats", American Heart Association, Inc., 2019, pp. 1120-1127.
Toro et al., "Erythropoietin induces bone marrow and plasma fibroblast growth factor 23 during acute kidney injury", Kidney Int., 2018, 12 pages.
Uijl et al., "Strong and Sustained Antihypertensive Effect of Small Interfering RNA Targeting Liver Angiotensinogen", American Heart Association, Inc., 2019, pp. 1249-1257.
Dey et al., "Transcutaneous Measurement of Glomerular Filtration Rate in a Mouse Model of Diabetic Kidney Disease", Am. Soc. Nephrol., Kidney Week Abstract Supplement, PUB451, 2017, pp. 1078-1079.
Friedman et al., "Improved kinetic model for the transcutaneous measurement of glomerular filtration rate in experimental animals", Kidney International, 2106, vol. 90, pp. 1377-1385.
Geraci et al., "Transcutaneous Assessment of Glomerular Filtration Rate", Stud Health Technol. Inform., 2014, vol. 200, pp. 105-110.
Haimbach et al., "Longitudinal Characterization of Glomerular Filtration Rate of the Naïve ZSF1 Rat", J. Am. Soc. Nephrol., TH-P0464, 2016, vol. 27, 1 page.
Huang et al., "Analysis of Exogenous Near Infrared Fluorescent Markers for the Transcutaneous Measurement of Glomerular Filtration Rate", J. Am. Soc. Nephrol., Kidney Week Abstract Supplement, TH-PO740, 2015, vol. 26, pp. 259A-259B.
Kojima et al., "Longitudinal Transcutaneous Glomerular Filtration Rate (GFR) After Uninephrectomy (UNx) in Mice", J. Am. Soc Nephrol, Kidney Week Abstract Supplement, SA-PO455, 2015, vol. 26, p. 728A.
Mondritski et al., "Transcutaneous glomerular filtration rate measurement in a canine animal model of chronic kidney disease", Journal of Pharmacological and Toxicological Methods, 2018, vol. 90, pp. 7-12.
Scarfe et al., "Using Transdermal Measurement of GFR to Evaluation Long-Term Outcomes in Mouse Models of AKI", J. Am. Soc. Nephrol., TH-PO094, 2018, vol. 29, p. 134.
Shmarlouski et al., "Automatic artifact removal from GFT measurements", Biomedical Signal Processing and Control, 2014, vol. 14, pp. 30-41.
Shmarlouski et al., "A Novel Analysis Technique for Transcutaneous Measurement of Glomerular Filtration Rate With Ultralow Dose Marker Concentrations", IEEE Transactions on Biomedical Engineering, 2016, vol. 63, No. 8, pp. 1742-1750.
Soranno et al., "Transcutaneous Measurement of Glomerular Filtration Rate to Assess the Progression from Acute to Chronic Kidney Disease following Bilateral Ischemic Injury in Mice", J. Am. Soc. Nephrol., TH-PO085, 2016, vol. 27, p. 114A.
Su et al., "A Longitudinal Study on Kidney Function, Pathology, and Multiple Urinary Biomarkers in ZSF1 Rat Model of Type II Diabetic Nephropathy", J. Am. Soc. Nephrol., SA-PO364, 2015, vol. 26, p. 709A.
William-Olsson et al., "Non-Invasive GFR Assessment in Conscious Rats with Puromycin Induced Nephropathy", J. Am. Soc. Nephrol., FR-PO091, 2014, vol. 25, p. 392A.
Anaam et al., "Pathobiology of Cyst Progression in Nbce1A and Pkd1 (RC/RC) Mouse Models", Am. Soc. Nephrol. Kidney Week Abstract Supplement: PO1554, (2020), 4 pages.
Bidwell et al., "Dose Escalating Toxicology Study of ELP-VEGF, a Novel Biologic for Renal Therapeutic Angiogenesis", ERA-EDTA Meeting 2020, Nephrology Dialysis Transplantation 35 (Supplement 3):P0117, 2 pages.
Bode et al., "Deficiency of the Anaphylatoxin Receptors C5aR2 and C3aR Aggravates Hypertensive Renal Injury", Am. Soc. Nephrol. Kidney Week Abstract Supplement: SA-PO339 2019, 14 pages.
Bovee et al., "Abstract MP32: Effectiveness Of Investigational RNAi Therapeutics Targeting Liver Angiotensinogen In Experimental Chronic Kidney Disease", American Heart Association Journals—Hypertension, Sep. 9, 2020, https://doi.org/10.1161/hyp.76.suppl_1.MP32, Hypertension. 2020;76:AMP32; 5 pages.
Cornelius et al., "NLRP3 inflammasome inhibition attenuates sepsis-induced platelet activation and prevents multi-organ injury in cecal-ligation puncture", PLOS ONE, Jun. 17, 2020, https://doi.org/10.1371/journal.pone.0234039, 15 pages.
De Chiari et al., "Tubular Epithelial Cell Polyploidzation is Required to Survive AKI but Promotes CKD Development", ERA-EDTA Meeting 2020, Nephrology Dialysis Transplantation 35 (Supplement 3):MO065,1 page.
Faubel et al., "Sex as a Biological Variable in Cardiac Outcomes after AKI in Mice", Am. Soc. Nephrol. Kidney Week Abstract Supplement: PO0147, (2020), 2 pages.
Fu et al., "Chronic effects of repeated low dose cisplatin treatment in mouse kidneys and renal tubular cells", American Journal of Physiology, Renal Physiology, Sep. 18, 2019, https://doi.org/10.1152/ajprenal.00385.2019, pp. F1582-F1592.
Geng et al., "The urea transporter UT-A1 plays a predominant role in a urea-dependent urine-concentrating mechanism", Journal of Biological Chemistry, JBC Papers in Press., May 27, 2020, https://www.jbc.org/cgi/doi/10.1074/jbc.RA120.013628, 22 pages.
Giralt-Lopez et al., "Revisiting Experimental Models of Diabetic Nephropathy", International Journal of Molecular Sciences, 2020, vol. 21, No. 3587, doi: 10.3390/ijms21103587, 23 pages.
Gomez et al., "Glycogen synthase kinases 3-α/β inhibition attenuates progression of diabetic kidney disease beyond treatment with metformin/Ramipril/empagliflozin", Nephrology Dialysis Transplantation, vol. 34, Supplement 1, Jun. 2019, gfz096.FO051, https://doi.org/10.1093/ndt/gfz096.FO051, 2 pages.
Gupta et al., "Targeted Inhibition of Gut Microbial TMAO Production Reduces Renal Tubulointerstitial Fibrosis and Functional Impairment in a Murine Model of Chronic Kidney Disease", American Heart Association Journals, Arteriosclerosis, Thrombosis, and Vascular Biology, 2020;40:00-00. DOI: 10.1161/ATVBAHA.120.314139, 18 pages.
Hering et al., "α2A-Adrenoceptors Modulate Renal Sympathetic Neurotransmission and Protect against Hypertensive Kidney Disease", JASN Feb. 2020, ASN.2019060599; DOI: https://doi.org/10.1681/ASN.2019060599, pp. 783-798.
Hu et al., "Renomedullary Interstitial Cell Endothelin A Receptors Regulate BP and Renal Function", Journal of the American Society of Nephrology, JASN, Jun. 2020, ASN.2020020232; DOI: https://doi.org/10.1681/ASN.2020020232, 18 pages.
Iwakura et al., "HMGB1 in myeloid cells drives postischemic acute kidney injury by promoting neutrophil infiltration", Nephrology Dialysis Transplantation, vol. 34, Issue Supplement 1, Jun. 2019, gfz106.FP251, https://doi.org/10.1093/ndt/gtz106.FP251, 2 pages.

(56) References Cited

OTHER PUBLICATIONS

Kasztan et al., "Hyperfiltration predicts long-term renal outcomes in humanized sickle cell mice", The American Society of Hematology, 2019, vol. 3, No. 9, pp. 1460-1475.

Kodama et al., "Effect of Canagliflozin on Glomerular Hyperfiltration Evaluated by Transcutaneous GFR Monitor in Spontaneously Diabetic Torii Fatty Rats", Am. Soc. Nephrol. Kidney Week Abstract Supplement: FR-PO187, (2019), 2 pages.

Kodama et al., "Empagliflozin as an Add-On to Linagliptin Ameliorates Renal Interstitial Fibrosis in Spontaneously Diabetic Torii Fatty Rats", Am. Soc. Nephrol. Kidney Week Abstract Supplement: TH-PO910, (2019), 2 pages.

Lakshmipathi et al., "Nephron-Specific Disruption of Polycystin-1 Induces Cyclooxygenase-2-Mediated Blood Pressure Reduction Independent of Cystogenesis", Journal of the American Society of Nephrology, JASN Apr. 2020, ASN.2019090934; DOI: https://doi.org/10.1681/ASN.2019090934, 17 pages.

Li et al., "Phase-Specific IRF4 and IRF8 Regulation/Expression of Mononuclear Phagocytes During Ischemic Acute Kidney Injury/Disease", ERA-EDTA Meeting 2020, Nephrology Dialysis Transplantation 35 (Supplement 3):MO067, 1 page.

McPherson et al., "Altered renal hemodynamics is associated with glomerular lipid accumulation in obese Dahl salt-sensitive leptin receptor mutant rats", American Journal of Physiology, Renal Physiology, Feb. 18, 2020, https://doi.org/10.1152/ajprenal.00438.2019, 11 pages.

Menshikh et al., "Capillary rarefaction is more closely associated with CKD progression after cisplatin, rhabdomyolysis, and ischemia reperfusion-induced AKI than renal fibrosis", American Journal of Physiology, Renal Physiology, Sep. 11, 2019, https://doi.org/10.1152/ajprenal.00366.2019, pp. F1383-F1397.

Moonen et al., "Early, but Not Late, Contralateral Nephrectomy Overcomes Progression to CKD After Unilateral Ischemic Injury", ERA-EDTA Meeting 2020, Nephrology Dialysis Transplantation 35 (Supplement 3):P0546, 1 page.

Motrapu et al., "Drug Testing for Residual Progression of Diabetic Kidney Disease in Mice Beyond Therapy with Metformin, Ramipril, and Empagliflozin", Journal of the American Society of Nephrology, JASN, Jun. 2020, ASN.2019070703; DOI: https://doi.org/10.1681/ASN.2019070703, 45 pages.

Nagata et al., "Regular exercise and branched-chain amino acids prevent ischemic acute kidney injury-related muscle wasting in mice", The Physiological Society, Physiological Reports, 2020;8:e14557, 13 pages.

Ofori-Acquah et al., "Hemopexin deficiency promotes acute kidney injury in sickle cell disease", American Society of Hematology, Blood, Mar. 26, 2020, https://doi.org/10.1182/blood.2019002653, pp. 1044-1048.

Oltra et al., "Cardiac, renal and uterine hemodynamics changes throughout pregnancy in rats with a prolonged high fat diet from an early age", PLOS ONE, Jun. 30, 2020, https://doi.org/10.1371/journal.pone 0234861, 12 pages.

Ow et al., "The Effects of Chronic Dapagliflozin Treatment on the Renal Microvasculature in a Rat Model of Type 2 Diabetes", ERA-EDTA Meeting 2020, Nephrology Dialysis Transplantation 35 (Supplement 3):P0978, 1 page.

Pastor-Soler et al., "Effects of AMPK Deficiency and Sex-Differences in Kidney Parameters Post Uninephrectomy", Am. Soc Nephrol. Kidney Week Abstract Supplement: SA-PO732, (2019), 2 pages.

Qi et al., "Elevated Podocyte DAAM2 Expression in Diabetic Nephropathy", Am. Soc. Nephrol. Kidney Week Abstract Supplement: FR-PO192, (2019), 2 pages.

Rush et al., "Genetic or Pharmacologic Activation of Nrf2 Worsens Glomerular Injury and Proteinuria", Am. Soc. Nephrol. Kidney Week Abstract Supplement: TH-PO1082, (2019), 2 pages.

Saritas et al., "Disruption of CUL3-mediated ubiquitination causes proximal tubule injury and kidney fibrosis", Scientific Reports, Mar. 14, 2019, vol. 9., No. 4596, https://doi.org/10.1038/s41598-019-40795-0, 14 pages.

Shaver et al., "Cell-free hemoglobin augments acute kidney injury during experimental sepsis", American Journal of Physiology—Renal Physiology, Jul. 31, 2019, https://doi.org/10.1152/ajprenal.00375.2018, pp. F922-F929.

Shi et al., "Crystal Clots as Therapeutic Target in Cholesterol Crystal Embolization", Nephrology Dialysis Transplantation, vol. 34, Issue Supplement 1, Jun. 2019, gfz106.FP312, https://doi.org/10.1093/ndt/gfz106.FP312, 23 pages.

Shi et al., "Crystal Clots as Therapeutic Target in Cholesterol Crystal Embolism", American Heart Association Journals, Circulation Research, Feb. 24, 2020, https://doi.org/10.1161/CIRCRESAHA.119.315625, 1 page.

Shi, C., "Necroinflammation Versus Crystal Clots as Therapeutic Target in Cholesterol Crystal Embolism-Related Kidney Infarct", ERA-EDTA Meeting 2020, Nephrology Dialysis Transplantation 35 (Supplement 3):P0513, 1 page.

Shi et al., "Platelets vs. Neutrophils as Therapeutic Targets in Cholesterol Embolism-Related Arterial Occlusion, Kidney Infarction, and AKI", Am. Soc. Nephrol. Kidney Week Abstract Supplement: PO0215, (2020), 2 pages.

Sims et al., "Rolipram Improves Outcome in a Rat Model of Infant Sepsis-Induced Cardiorenal Syndrome", Frontiers in Pharmacology., 2017, vol. 8, Article 237, 13 pages.

Skrypnyk et al., "Fractional Excretion of NGAL Is Useful to Distinguish Prerenal Azotemia (PRA) from Acute Tubular Injury (ATI) in Mice", Am. Soc. Nephrol. Kidney Week Abstract Supplement: PO0174, (2020), 2 pages.

Sukumaran et al., "Liraglutide treatment improves the coronary microcirculation in insulin resistant Zucker obese rats on a high salt diet", Cardiovascular Diabetology, 2020, https://doi.org/10.1186/s12933-020-01000-z, 16 pages.

Szczepanski et al., "Acute kidney injury during pregnancy leads to increased sFlt-1 and sEng and decreased renal T regulatory cells in pregnant rats with HELLP syndrome", Biol Sex Differ, vol. 11, No. 54 (2020), 10 pages.

Tourki et al., "Deficit of resolution receptor magnifies inflammatory leukocyte directed cardiorenal and endothelial dysfunction with signs of cardiomyopathy of obesity", The FASEB Journal, May 27, 2020, DOI: 10.1096/fj.202000495RR, 14 pages.

Ullah et al., "Impact of choice of kinetic model for the determination of transcutaneous FITC-sinistrin clearance in rats with streptozotocin-induced type 1 diabetes", Clinical and Experimental Pharmacology and Physiology, Mar. 11, 2020, https://doi.org/10.1111/1440-1681.13301, 12 pages.

Wakasaki et al., "Glomerular filtrate proteins in acute cardiorenal syndrome", JCI Insight, 2019, vol. 4, No. 4, e122130. https://doi.org/10.1172/jci.insight.122130, DOI: 10.1159/000495750, 18 pages.

Wang et al., "Integrin P6 Knockout Ameliorates Glomerular Sensitization to Podocyte-Specific Injury", Am. Soc. Nephrol. Kidney Week Abstract Supplement: SA-PO568 2019.

Wang et al., "Intracellular Reactive Oxygen Species Mediate the Therapeutic Effect of Induced Pluripotent Stem Cells for Acute Kidney Injury", Hindawi, Oxidative Medicine and Cellular Longevity, Mar. 26, 2020, vol. 2020, Article ID 1609638, https://doi.org/10.1155/2020/1609638, 14 pages.

Wang et al., "Soluble (pro)renin receptor treats metabolic syndrome in mice with diet-induced obesity via interaction with PPARγ", American Society for Clinical Investigation, Feb. 13, 2020, https://doi.org/10.1172/jci.insight.128061, 18 pages.

Zarjou et al., "Ferritin Light Chain Confers Protection Against Sepsis-Induced Inflammation and Organ Injury", Frontiers in Immunology, Feb. 2019, vol. 10, Article 131, doi: 10.3389/fimmu.2019.00131, 15 pages.

Zhang et al., "Discovery of diarylamides as novel orally active diuretics targeting urea transporters", Acta Pharmaceutica Sinica B, May 26, 2020, https://doi.org/10.1016/j.apsb.2020.06.001, pp. 181-202.

Zhang et al., "Renal Fibrosis Is Significantly Attenuated Following Targeted Disruption of Cd40 in Experimental Renal Ischemia", Journal of the American Heart Association, 2020;9:e014072. DOI: 10.1161/JAHA.119.014072, 26 pages.

(56) References Cited

OTHER PUBLICATIONS

Abdelmageed et al., "TNFα Inhibition Decreases Fibrosis After Ischemia-Reperfusion Injury", Am. Soc. Nephrol. Kidney Week Abstract Supplement: TH-PO494, 2019, 2 pages.
Barnett et al., "Low birth weight is associated with impaired murine kidney development and function", Pediatric Research, 2017, vol. 82, No. 2, pp. 340-348.
Berns, J. S., "Clinical Decision Making in a Patient with Stage 5 CKD—Is eGFR Good Enough", American Society of Nephrology, 2015, doi: 10.2215/CJN.00340115, 8 pages.
Cowley et al., "Progression of glomerular filtration rate reduction determined in conscious Dahl salt-sensitive hypertensive rats", Hypertension, 2013, vol. 62, pp. 85-90.
Ellery et al., "Transcutaneous Measurement of Glomerular Filtration Rate in Small Rodents; Through the Skin for the Win", Nephrology, 2015, vol. 20, No. 3, pp. 117-123.
Endre et al., "Clearance and beyond: the complementary roles of GFR measurement and injury biomarkers in acute kidney injury (AKI)", Am J Physiol Renal Physiol, 2011, vol. 301, pp. F697-F707.
Eriguchi et al., "Renal Tubular ACE-Mediated Tubular Injury is The Major Contributor to Microalbuminuria in Early Diabetic Nephropathy", American Journal of Physiology—Renal Physiology, 2017, vol. 314, pp. F531-F542.
Evans et al., "Null Mutation of the Nicotinamide Adenine Dinucleotide Phosphate-Oxidase Subunit p67phox Protects the Dahl-S Rat From Salt-Induced Reductions in Medullary Blood Flow and Glomerular Filtration Rate", Hypertension, 2015, vol. 65, No. 3, pp. 561-568.
Ferguson et al., "Established and Emerging Markers of Kidney Function", Clinical Chemistry, 2012, vol. 58, No. 4, pp. 680-689.
Gagnon et al., "PBI-4425, A novel anti-inflamantory/fibrotic compound, improves kidney function and glomerular integrity in the diabetic DB/DB mouse mode", Nephrology Dialysis Transplantation, 2016, vol. 31, Abstract SO022, 1 page.
Gallo et al., "Once daily administration of the SGLT2 inhibitor, empagliflozin, attenuates markers of renal fibrosis without improving albuminuria in diabetic db/db mice", Sci Rep., 2016, vol. 6, No. 26428, 16 pages.
Giani et al., "Renal Angiotensin-Converting Enzyme Is Essential for the Hypertension Induced by Nitric Oxide Synthesis Inhibition", J. Am. Soc. Nephrol., 2014, vol. 25, No. 12, pp. 2752-2763.
Giani et al., "Renal generation of angiotensin II and the pathogenesis of hypertension", Curr Hypertension Reports, 2014, vol. 16, No. 9, 477, 10 pages.
Hilliard et al., "Chronic recurrent dehydration associated with periodic water intake exacerbates hypertension and promotes renal damage in male spontaneously hypertensive rats", Sci. Rep. 2016, vol. 6, No. 33855, 13 pages.
Hokke et al., "Maternal Fat Feeding Augments Offspring Nephron Endowment in Mice", PLoS One, 2016, vol. 11, No. 8, e0161578, 19 pages.
Hokke et al., "Maternal Glucose Intolerance Reduces Offspring Nephron Endowment and Increases Glomerular Volume in Adult Offspring", Diabetes Metab Res Rev., 2016, DOI: 10.1002/dmrr [Epub ahead of print], 11 pages.
Honeycutt et al., "Medical Costs of CKD in the Medicare Population", Journal of American Society of Nephrology, 2013, vol. 24, pp. 1478-1483.
Hoste et al., "AKI patients have worse long-term outcomes, especially in the immediate post-ICU period", Hoste and De Corte Critical Care, 2012, vol. 16, No. 148, 2 pages.
Josephs et al., "Perioperative Risk Assessment, Prevention, and Treatment of Acute Kidney Injury", International Anesthesiology Clinics, 2009, vol. 47, No. 4, pp. 89-105.
Kittikulsuth et al., "Lack of an effect of nephron-specific deletion of adenylyl cyclase 3 on renal sodium and water excretion or arterial pressure", Physiol Rep., 2015, vol. 3, No. 3, e12316, 9 pages.
Kuhns et al., "Novel Differences in Renal Gene Expression in a Diet Induced Obesity Model", American Journal of Physiology—Renal Physiology, 2017, vol. 314, pp. F517-F530.
Ma et al., "Sodium glucose transporter-2 inhibition has no renoprotective effects on non-diabetic chronic kidney disease" Physiological Reports, 2017, vol. 5, Iss. 7, e13228, 8 pages.
McMahon et al., "GFR Measurement and Chemotherapy Dosing in Patients with Kidney Disease and Cancer", The American Society of Nephrology, Kidney360, 2020, vol. 1, No. 2, pp. 141-150.
Molitoris et al., "Measuring glomerular filtration rate in acute kidney injury: Yes, but not yet", Molitoris Critical Care, 2012, vol. 16, No. 158, 2 pages.
Mulay et al., "Beta-Hydroxybutyrate inhibits NLRP3-Mediated inflammation and delays progressive renal failure during primary hyperoxaluria related kidney stone Disease", Nephrology Dialysis Transplantation, 2016, vol. 31, Supplement 1, Abstract TO027, 1 page.
Perez et al., "Transcutaneous Assessment of Renal Function in Conscious Rodents", J. Vis. Exp., 2016, vol. 109, 253767, 8 pages.
Rabito et al., "Noninvasive, Real-Time Monitoring of Renal Function: The Ambulatory Renal Monitor", The Journal of Nuclear Medicine, 1992, vol. 34, No. 2, pp. 199-207.
Rule et al., "Measured and Estimated GFR in Healthy Potential Kidney Donors", American Journal of Kidney Diseases, 2004, vol. 1, No. 1, pp. 112-119.
Sadick et al., "Two non-invasive GFR-estimation methods in rat models of polycystic kidney disease: 3.0 Tesla dynamic contrast enhanced MRI and optical imaging", Nephrol. Dial. Transplant., 2011, vol. 26, No. 10, pp. 3101-3108.
Scarfe et al., "Measures of kidney function by minimally invasive techniques correlate with histological glomerular damage in SCID mice with adriamycin-induced nephropathy", Sci Rep., 2015, vol. 5, No. 13601, 13 pages.
Schock-Kusch et al., "Online feedback-controlled renal constant infusion clearances in rats", Kidney Int., 2012, vol. 82, No. 3, pp. 314-320.
Schock-Kusch et al., "Reliability of transcutaneous measurement of renal function in various strains of conscious mice", PLoS ONE, 2013, vol. 8, No. 8, e71519, 5 pages.
Schock-Kusch et al., "Transcutaneous assessment of renal function in conscious rats with a device for measuring FITC sinistrin disappearance curves", Kidney Int., 2011, vol. 79, pp. 1254-1258.
Schreiber et al., "Transcutaneous measurement of renal function in conscious mice", Am. J. Physiol. Renal Physiol., 2012, vol. 303, No. 5, pp. F783-F788.
Spradley et al.",Placental Growth Factor Administration Abolishes Placental Ischemia-Induced Hypertension", Hypertension, 2016, vol. 67, No. 4, pp. 740-747.
Steinbach et al., "A pilot study to assess the feasibility of transcutaneous glomerular filtration rate measurement using fluorescence-labelled sinistrin in dogs and cats", PLoS ONE, 2014, vol. 9, No. 11, e111734, pp. 1-10.
Su et al., "Longitudinal Changes in Measured Glomerular Filtration Rate, Renal Fibrosis and Biomarkers in a Rat Model of Type 2 Diabetic Nephropathy", Am J Nephrol, 2016, vol. 44, pp. 339-353.
Sukumaran et al., "Liraglutide Treatment Improves Renal Vascular Function in Zucker Rats as Visualized by Microangiography", Am. Soc. Nephrol. Kidney Week Abstract Supplement: SA-OR098, (2017), 3 pages.
Thomasova et al., "MDM2 Prevents Spontaneous Tubular Epithelial Cell Death and Acute Kidney Injury", D Cell Death and Disease, 2016, vol. 7, e2482; 14 pages.
Trudu et al., "Common noncoding UMOD gene variants induce salt-sensitive hypertension and kidney damage by increasing uromodulin expression", Nat. Med., 2013, vol. 19, No. 12, 19 pages.
Ward et al., "Targeted mitochondrial therapy using MitoQ shows equivalent renoprotection to angiotensin converting enzyme inhibition but no combined synergy in diabetes", Scientific Reports, 2017, vol. 7, No. 15190, 14 pages.
Zhou et al., "An integrin antagonist (MK-0429) decreases proteinuria and renal fibrosis in the ZSF1 rat diabetic nephropathy model", Pharmacology Research & Perspectives, 2017, vol. 5, Iss. 5, e00354, 14 pages.

(56) References Cited

OTHER PUBLICATIONS

Zollner et al., "Simultaneous Measurement of Kidney Function by Dynamic Contrast Enhanced MRI and FITC-Sinistrin Clearance in Rats at 3 Tesla: initial results", PLoS ONE, 2013, vol. 8, No. 11, e79992, 10 pages.

* cited by examiner

METHODS FOR RENAL FUNCTION DETERMINATION

CROSS-REFERENCE TO RELATED APPLICATIONS

This application claims priority to U.S. Provisional Patent Application No. 62/577,951, filed on Oct. 27, 2017, the disclosure of which is hereby incorporated herein by reference in its entirety.

BACKGROUND OF THE INVENTION

The field of the disclosure generally relates to methods and pharmaceutical compositions comprising pyrazine derivatives to assess the renal function of a patient in need thereof.

Acute renal failure (ARF) is a common ailment in patients admitted to general medical-surgical hospitals. Approximately half of the patients who develop ARF die either directly from ARF or from complications associated with an underlying medical condition, while survivors face marked increases in morbidity and prolonged hospitalization. Early diagnosis is generally believed to be important because renal failure is often asymptomatic and typically requires careful tracking of renal function markers in the blood. Dynamic monitoring of renal functions of patients is desirable in order to minimize the risk of acute renal failure brought about by various clinical, physiological and pathological conditions. Such dynamic monitoring tends to be particularly important in the case of critically ill or injured patients because a large percentage of these patients tend to face risk of multiple organ failure (MOF) potentially resulting in death. MOF is a sequential failure of the lungs, liver and kidneys and is incited by one or more of acute lung injury (ALI), adult respiratory distress syndrome (ARDS), hypermetabolism, hypotension, persistent inflammatory focus and sepsis syndrome. The common histological features of hypotension and shock leading to MOF generally include tissue necrosis, vascular congestion, interstitial and cellular edema, hemorrhage and microthrombi. These changes generally affect the lungs, liver, kidneys, intestine, adrenal glands, brain and pancreas in descending order of frequency. The transition from early stages of trauma to clinical MOF generally corresponds with a particular degree of liver and renal failure as well as a change in mortality risk from about 30% up to about 50%.

Traditionally, renal function of a patient has been determined using crude measurements of the patient's urine output and plasma creatinine levels. These values are frequently misleading because such values are affected by age, state of hydration, renal perfusion, muscle mass, dietary intake, and many other clinical and anthropometric variables. In addition, a single value obtained several hours after sampling may be difficult to correlate with other physiologic events such as blood pressure, cardiac output, state of hydration and other specific clinical events (e.g., hemorrhage, bacteremia, ventilator settings and others).

Chronic Kidney Disease (CKD) is a medical condition characterized in the gradual loss of kidney function over time. It includes conditions that damage the kidneys and decrease their ability to properly remove waste products from the blood of an individual. Complications from CKD include high blood pressure, anemia (low blood count), weak bones, poor nutritional health and nerve damage in addition to an increased risk of heart disease. According to the National Kidney Foundation, approximately two-thirds of all cases of CKD are caused by diabetes or hypertension. In addition to a family history of kidney disease, other risk factors include age, ethnicity, hypertension, and diabetes. The renal glomerular filtration rate (GFR) is the best test to determine the level of kidney function and assess the stage of a patient's CKD.

The GFR is an important test to determine the level of kidney function which determines the state of CKD. As shown in Table 1 and FIG. 28, the lower the GFR, the more serious the CKD. The GFR can be estimated based on a blood test measuring the blood creatinine level in combination with other factors. More accurate, and therefore more useful, methods require the injection of an endogenous substance into a patient followed by careful monitoring of urine output over a period of time. These are often contrast agents (CA) that can cause renal problems on their own. Radioisotopes or iodinated aromatic rings are two common categories of CAs that are used for GFR determination.

TABLE 1

| Stage | Description | GFR |
| --- | --- | --- |
| At increased risk | Increase of risk factors (e.g., diabetes, high blood pressure, family history, age, ethnicity) | >90 |
| 1 | Kidney damage with normal kidney function | >90 |
| 2 | Kidney damage with mild loss of kidney function | 60-89 |
| 3a | Mild to moderate loss of kidney function | 44-59 |
| 3b | Moderate to severe loss of kidney function | 30-44 |
| 4 | Severe loss of kidney function | 15-29 |
| 5 | Kidney failure; dialysis required | <15 |

Contrast Induced Nephropathy (CIN) is a serious complication connected to the use of radioisotopes or iodinated CAs. It is thought that CIN is caused by either renal vasoconstriction or tubular injury caused by the CA. The definition of CIN varies from study to study but the most common definition, based on the symptoms experienced by the patient, include an increase in serum creatinine by at least 25% above baseline occurring two to five days after exposure to the CA in the absence of other causes of acute renal failure. CIN can be fatal for up to 20% of patients hospitalized due to these complications. The more severe the CKD, the greater the risk for CIN. Thus, the patients most in need of accurate GFR data are most at risk for developing sometimes fatal complications in getting that data.

With regard to conventional renal monitoring procedures, an approximation of a patient's glomerular filtration rate (GFR) can be made via a 24 hour urine collection procedure that (as the name suggests) typically requires about 24 hours for urine collection, several more hours for analysis, and a meticulous bedside collection technique. Unfortunately, the undesirably late timing and significant duration of this conventional procedure can reduce the likelihood of effectively treating the patient and/or saving the kidney(s). As a further drawback to this type of procedure, repeat data tends to be equally as cumbersome to obtain as the originally acquired data.

Occasionally, changes in serum creatinine of a patient must be adjusted based on measurement values such as the patient's urinary electrolytes and osmolarity as well as derived calculations such as "renal failure index" and/or "fractional excretion of sodium." Such adjustments of serum creatinine undesirably tend to require contemporaneous collection of additional samples of serum and/or urine and, after some delay, further calculations. Frequently, dosing of medication is adjusted for renal function and thus can be equally as inaccurate, equally delayed, and as difficult to reassess as the measurement values and calculations upon which the dosing is based. Finally, clinical decisions in the critically ill population are often equally as important in their timing as they are in their accuracy.

It is known that hydrophilic, anionic substances are generally capable of being excreted by the kidneys. Renal clearance typically occurs via two pathways: glomerular filtration and tubular secretion. Tubular secretion may be characterized as an active transport process, and hence, the substances clearing via this pathway typically exhibit specific properties with respect to size, charge and lipophilicity.

Most of the substances that pass through the kidneys are filtered through the glomerulus (a small intertwined group of capillaries in the malpighian body of the kidney). Examples of exogenous substances capable of clearing the kidney via glomerular filtration (hereinafter referred to as "GFR agents") are shown in FIG. 1 and include creatinine (1), o-iodohippuran (2), and $^{99m}$Tc-DTPA (3). Examples of exogenous substances that are capable of undergoing renal clearance via tubular secretion include $^{99m}$Tc-MAG3 (4) and other substances known in the art. $^{99m}$Tc-MAG3 (4) is also widely used to assess renal function though gamma scintigraphy as well as through renal blood flow measurement. As one drawback to the substances illustrated in FIG. 1, o-iodohippuran (2), $^{99m}$Tc-DTPA (3) and $^{99m}$Tc-MAG3 (4) include radioisotopes to enable the same to be detected. Even if non-radioactive analogs (e.g., such as an analog of o-iodohippuran (2)) or other non-radioactive substances were to be used for renal function monitoring, such monitoring would typically require the use of undesirable ultraviolet radiation for excitation of those substances.

Pyrazine derivatives are known in the art for use in renal monitoring, including those disclosed in U.S. Pat. Nos. 8,155,000, 8,664,392, 8,697,033, 8,722,685, 8,778,309, 9,005,581, 9,114,160, 9,283,288, 9,376,399, and 9,480,687 which are incorporated by reference in their entirety.

BRIEF DESCRIPTION OF THE INVENTION

In one aspect, disclosed herein is a compound of Formula I, wherein each of

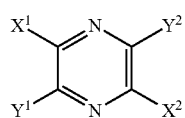

Formula I $X^1$ and $X^2$ is independently —$CO_2R^1$, —$CONR^1R^2$, —CO(AA) or —CONH(PS); each of $Y^1$ and $Y^2$ is independently selected from the group consisting of —$NR^1R^2$ and

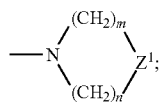

$Z^1$ is a single bond, —$CR^1R^2$—, —O—, —$NR^1$—, —$NCOR^1$—, —S—, —SO—, or —$SO_2$—; each of $R^1$ to $R^2$ are independently selected from the group consisting of H, —$CH_2(CHOH)_aH$, —$CH_2(CHOH)_aCH_3$, —$CH_2(CHOH)_a$ $CO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; AA is a peptide chain comprising one or more amino acids selected from the group consisting of natural and unnatural amino acids, linked together by peptide or amide bonds and each instance of AA may be the same or different than each other instance; PS is a sulfated or non-sulfated polysaccharide chain comprising one or more monosaccharide units connected by glycosidic linkages; and 'a' is a number from 1 to 10, 'c' is a number from 1 to 100, and each of 'm' and 'n' are independently a number from 1 to 3.

In another aspect, disclosed herein is a system for determining a GFR in a patient in need thereof. The system comprises a computing device, a display device communicatively coupled to said computing device, a power supply that is operatively coupled to said computing device and maintains electrical isolation of the system from external power sources, one or more sensor heads operatively coupled to said computing device, and at least one tracer agent configured to emit spectral energy when exposed to electromagnetic radiation. The computing device is configured to operate and control said sensor heads, record one or more measurements sent from said sensor heads, and calculate the GFR of said patient based on said measurements. The one or more sensor heads comprise at least one source of electromagnetic radiation and are configured to generate and deliver electromagnetic radiation, detect and measure the spectral energy emitted by said tracer agent, and transmit said measurement emitted by said tracer agent to said computing device. The tracer agent is configured to be administered to said patient, and emit spectral energy that is detectable by said sensor heads when exposed to electromagnetic radiation.

In still yet another aspect, disclosed herein is a system for transdermally determining a body-size normalized GFR in a patient. The system comprises a computing device, a display device communicatively coupled to said computing device, a power supply that is operatively coupled to said computing device and maintains electrical isolation of the system from external power sources, one or more sensor heads operatively coupled to said computing device, and at least one tracer agent configured to emit spectral energy when exposed to electromagnetic radiation. The one or more sensor heads comprise at least one source of electromagnetic radiation and are configured to generate and deliver electromagnetic radiation, detect and measure the spectral energy emitted by said tracer agent, and transmit said measurement emitted by said tracer agent to said computing device. The tracer agent is configured to be administered to said patient, and emit spectral energy that is detectable by said sensor heads when exposed to electromagnetic radiation. The computing device is configured to operate and control said sensor heads, record one or more measurements sent from said sensor heads, determine a decay parameter from the measured spectral energy over a measurement time window, determine a quality metric associated with the measured spectral energy over the measurement time window, use the quality metric to assess whether the decay parameter determination is sufficiently accurate, and if not, increase the measurement time window until the quality metric assessment indicates sufficient accuracy, convert the decay parameter into a body-size-corrected or volume of distribution ($V_d$) of the tracer agent normalized measurement of GFR and report the result on the display.

In still yet another aspect, disclosed herein is a method for determining a glomerular filtration rate (GFR) in a patient in need thereof. The method comprises administering to said patient a compound of Formula I, or a pharmaceutically acceptable salt thereof, measuring a concentration of the compound of Formula I in said patient over a measurement time window, and determining the GFR in said patient, wherein in the compound of Formula I, each of $X^1$ and $X^2$ is independently

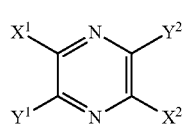

Formula I

—$CO_2R^1$, —$CONR^1R^2$, —CO(AA) or —CONH(PS); each of $Y^1$ and $Y^2$ is independently selected from the group consisting of —$NR^1R^2$ and

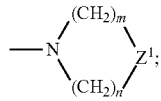

$Z^1$ is a single bond, —$CR^1R^2$—, —O—, —$NR^1$—, —$NCOR^1$—, —S—, —SO—, or —$SO_2$—; each of $R^1$ to $R^2$ are independently selected from the group consisting of H, —$CH_2(CHOH)_aH$, —$CH_2(CHOH)_aCH_3$, —$CH_2(CHOH)_a$ $CO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; AA is a peptide chain comprising one or more amino acids selected from the group consisting of natural and unnatural amino acids, linked together by peptide or amide bonds and each instance of AA may be the same or different than each other instance; PS is a sulfated or non-sulfated polysaccharide chain comprising one or more monosaccharide units connected by glycosidic linkages; and 'a' is a number from 1 to 10, 'c' is a number from 1 to 100, and each of 'm' and 'n' are independently a number from 1 to 3.

In still yet another aspect, disclosed herein is a method of assessing renal function in a patient. The method comprises administering a fluorescent compound, or a pharmaceutically acceptable salt thereof, to said patient; exposing said fluorescent compound to electromagnetic radiation, thereby causing spectral energy to emanate from said fluorescent compound; detecting the spectral energy emanated from said fluorescent compound; and assessing renal function of the patient based on the detected spectral energy.

Outlier Exclusion Method 1 (Hybrid offset method; GFR determination by MB-102 normalized to BSA).

Figure 22:
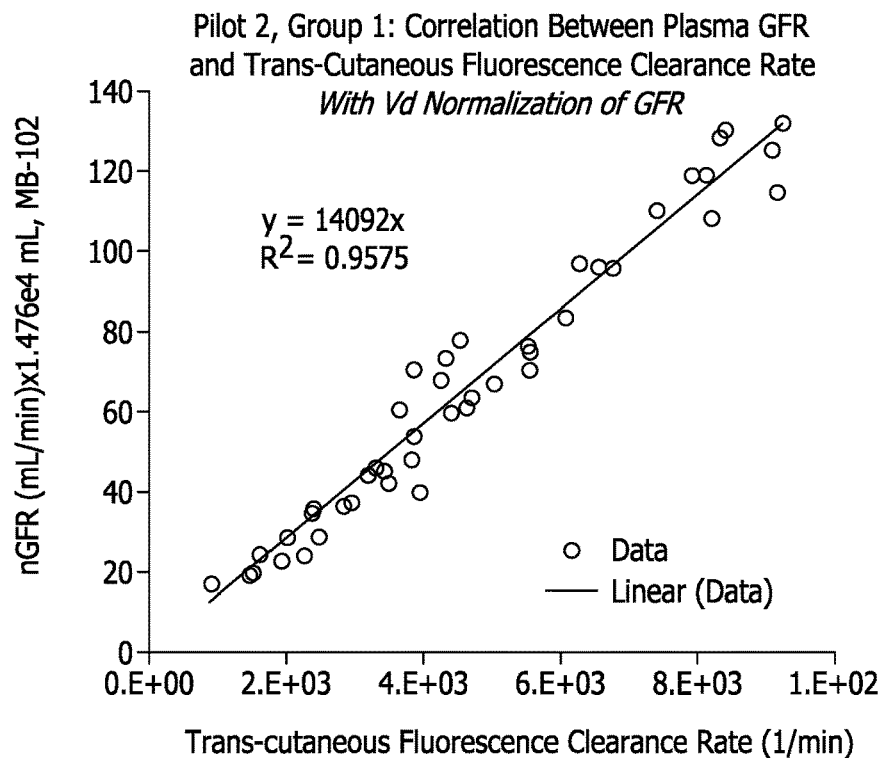

FIG. 22 is a graph correlating the plasma-determined GFR to the trans-cutaneous fluorescence clearance rate: Outlier Exclusion Method 1 (Hybrid offset method; GFR determination by MB-102 with $V_d$ normalization method 2).

Figure 23:
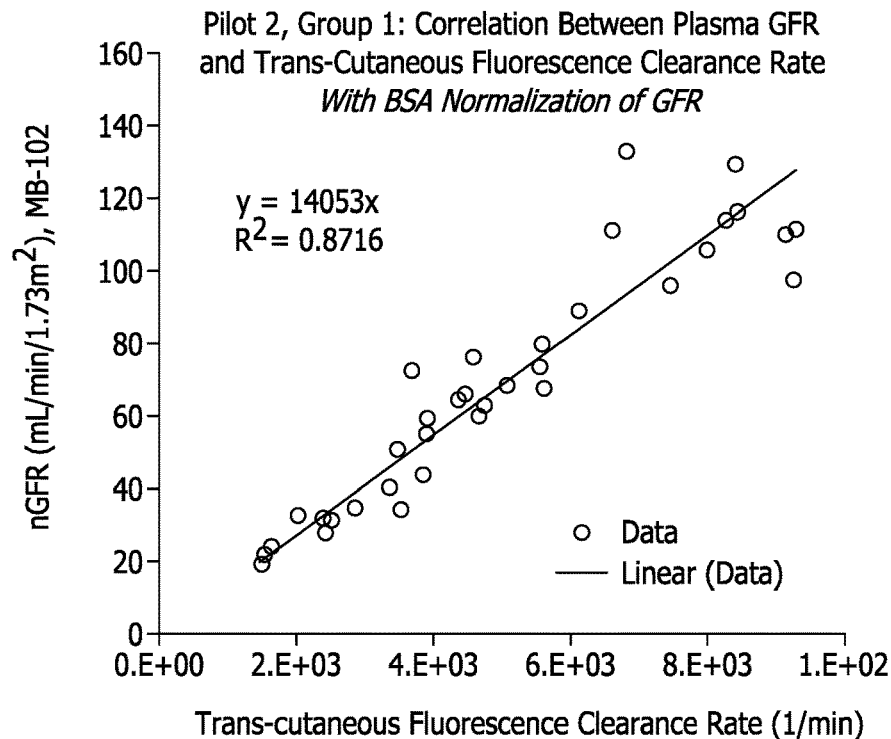

FIG. 23 is a graph correlating the plasma-determined GFR to the trans-cutaneous fluorescence clearance rate: Outlier Exclusion Method 2 (Hybrid offset method; GFR determination by MB-102 normalized to BSA).

Figure 24:
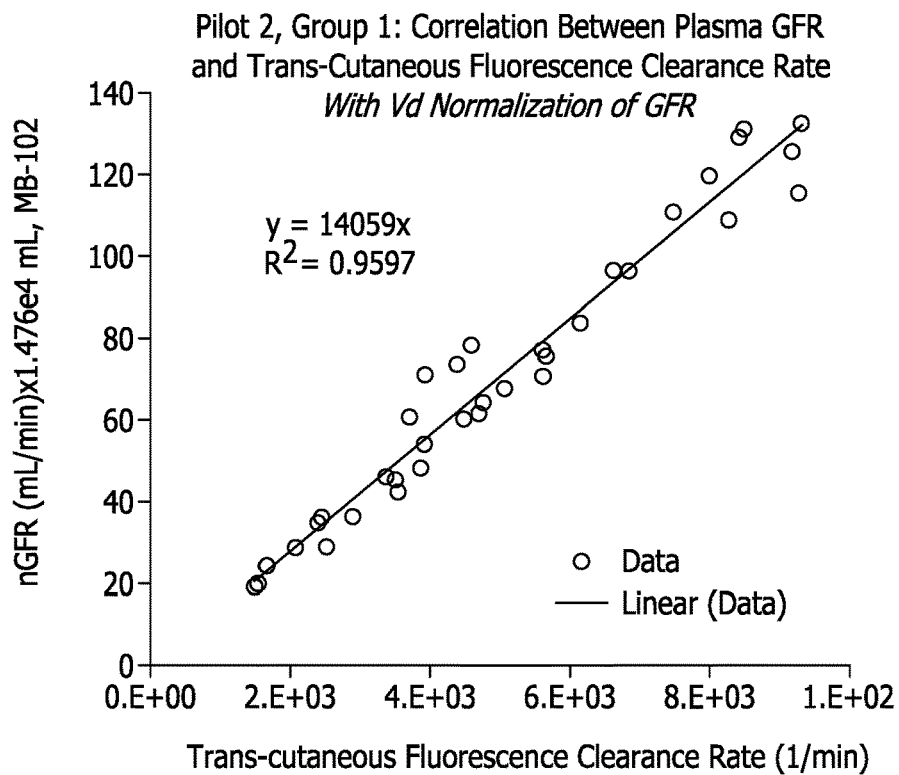

FIG. 24 is a graph correlating the plasma-determined GFR to the trans-cutaneous fluorescence clearance rate: Outlier Exclusion Method 2 (Hybrid offset method; GFR determination by MB-102 with $V_d$ normalization method 2).

Figure 25:
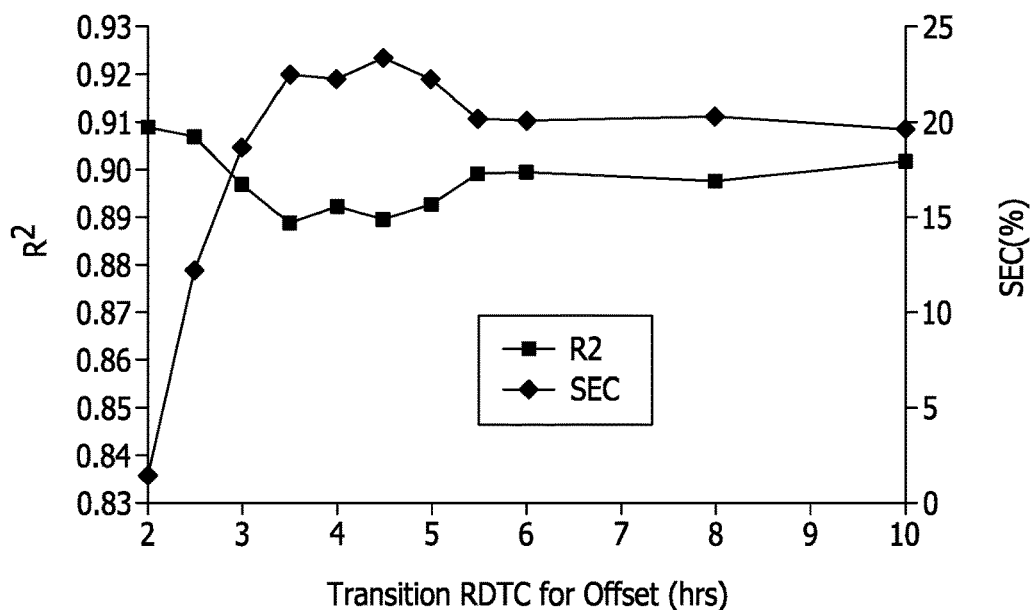

FIG. 25 is a graph summarizing the optimization of the RDTC transition for determining the offset method used in fitting the RDTC.

Figure 26:
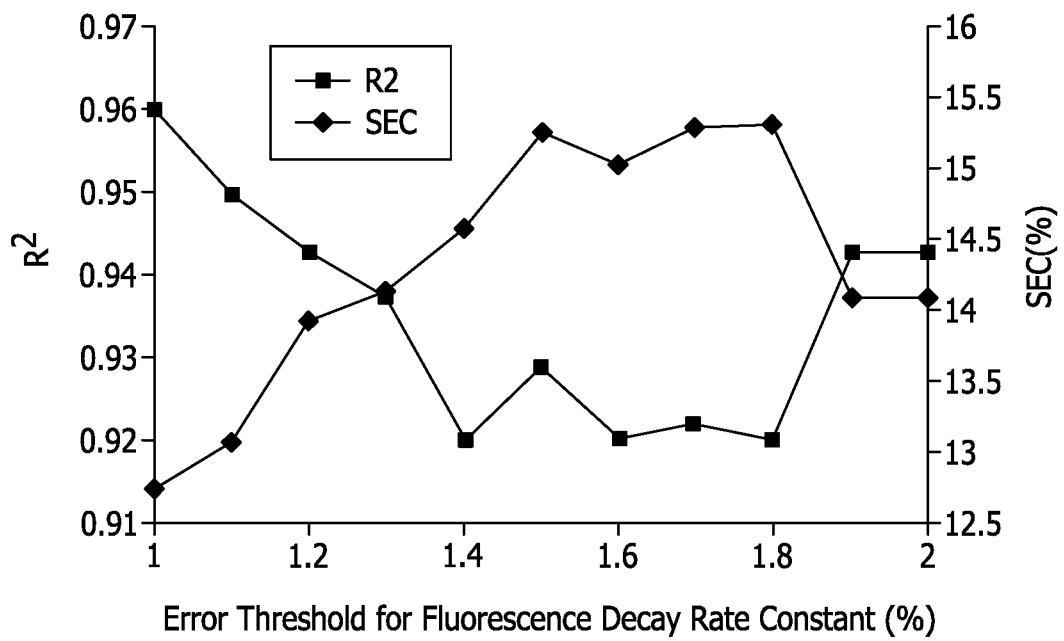

FIG. 26 is a graph summarizing the optimization of the Outlier Error Threshold for the Fluorescence Decay Rate Constant.

Figure 27:
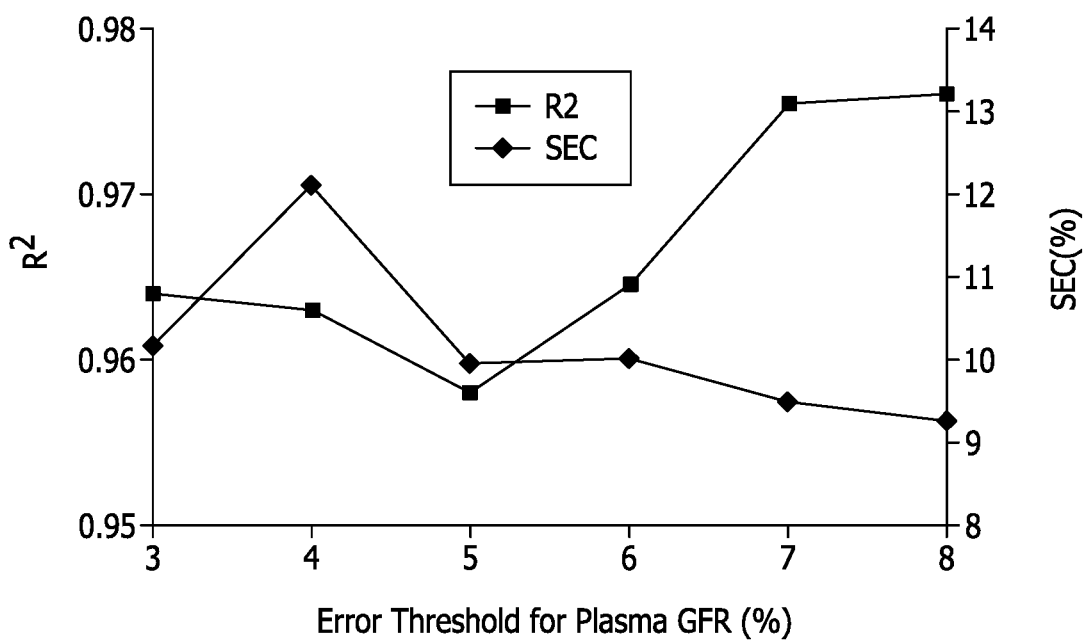

FIG. 27 is a graph summarizing optimization of the Outlier Error Threshold for plasma-determined GFR.

Figure 28:
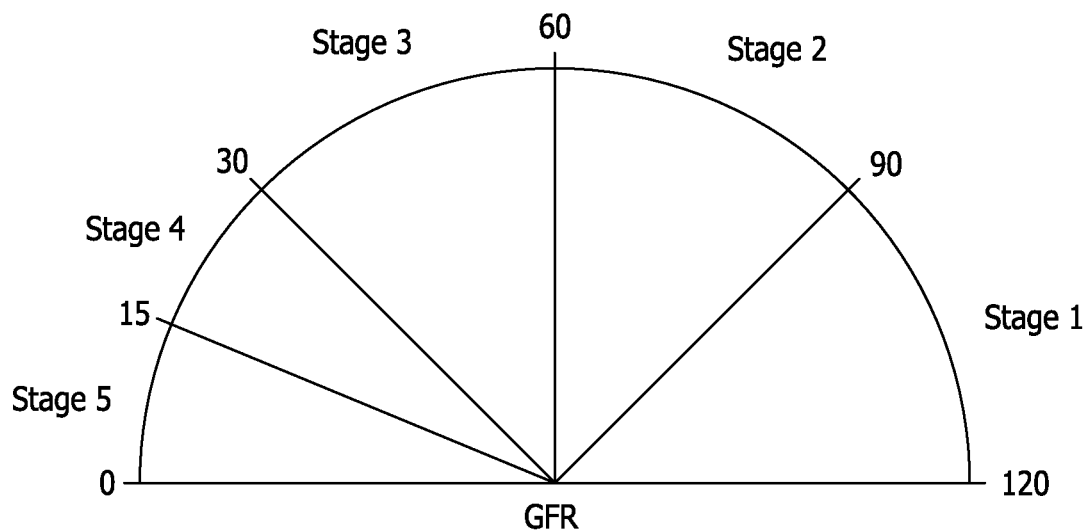

FIG. 28 is a graphical depiction of the 5 stages of chronic kidney disease by GFR.

Figure 29A:
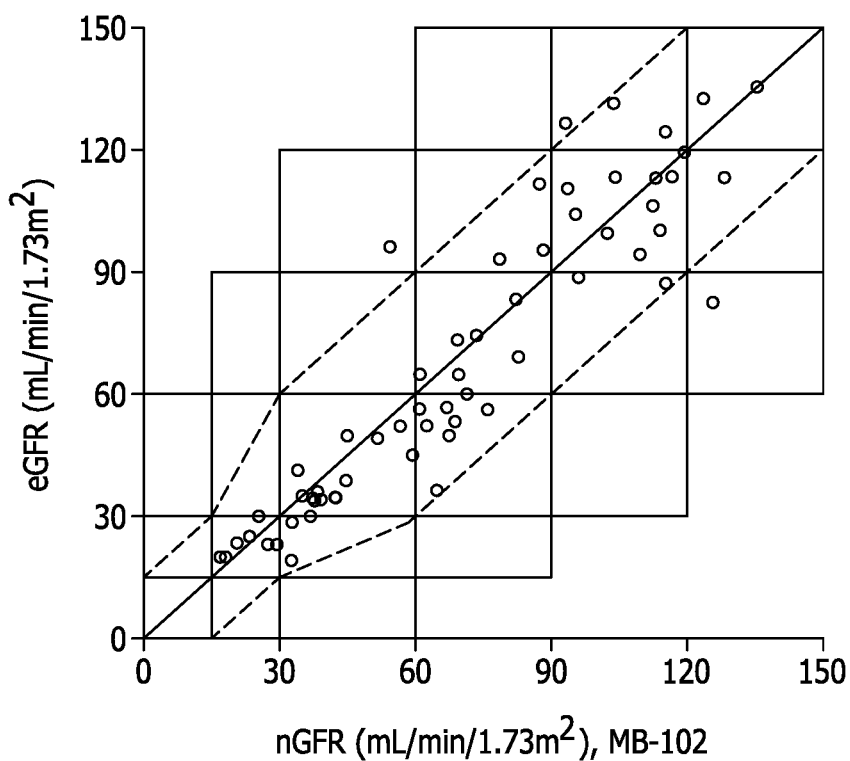

FIG. 29a is a graph of eGFR vs. plasma PK-determined GFR, normalized for subject body surface area (nGFR). Superimposed on the graph is an error grid, indicating diagnosis accuracy, by number of CKD stages. Measurements falling within a grid with only green sides would be correctly diagnosed by eGFR. Measurements falling within a grid with both green and yellow sides would be incorrectly diagnosed by eGFR by one CKD stage. Measurements falling within a grid with both yellow and red sides would be incorrectly diagnosed by eGFR by two CKD stages.

Figure 29B:
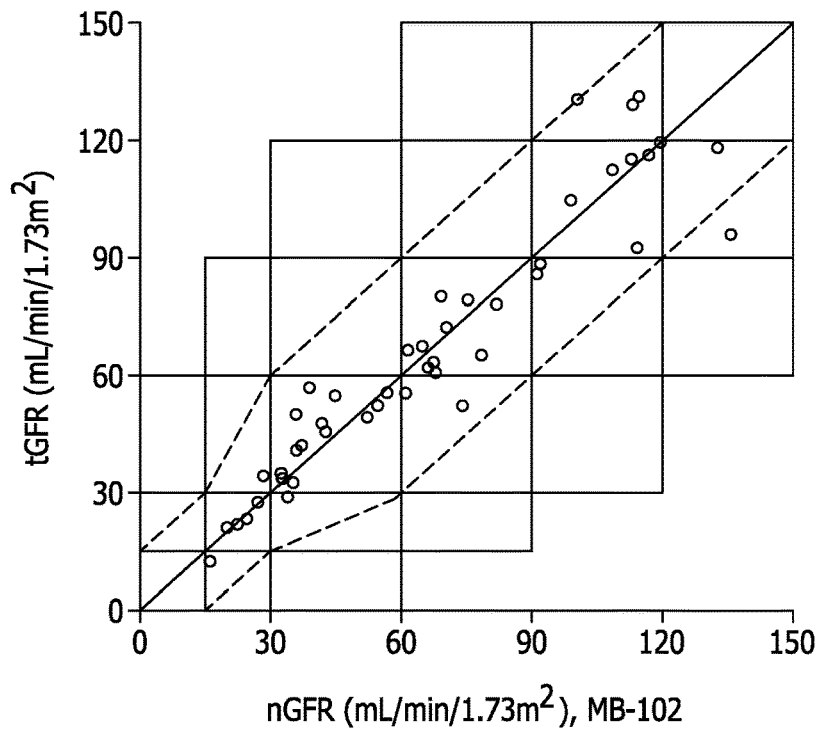

FIG. 29b is a graph of transdermally determined GFR (tGFR) vs. plasma PK-determined GFR, normalized for subject body surface area (nGFR). Superimposed on the graph is an error grid, indicating diagnosis accuracy, by number of CKD stages. Measurements falling within a grid with only green sides would be correctly diagnosed by tGFR. Measurements falling within a grid with both green and yellow sides would be incorrectly diagnosed by tGFR by one CKD stage. Measurements falling within a grid with both yellow and red sides would be incorrectly diagnosed by tGFR by two CKD stages.

Figure 29C:
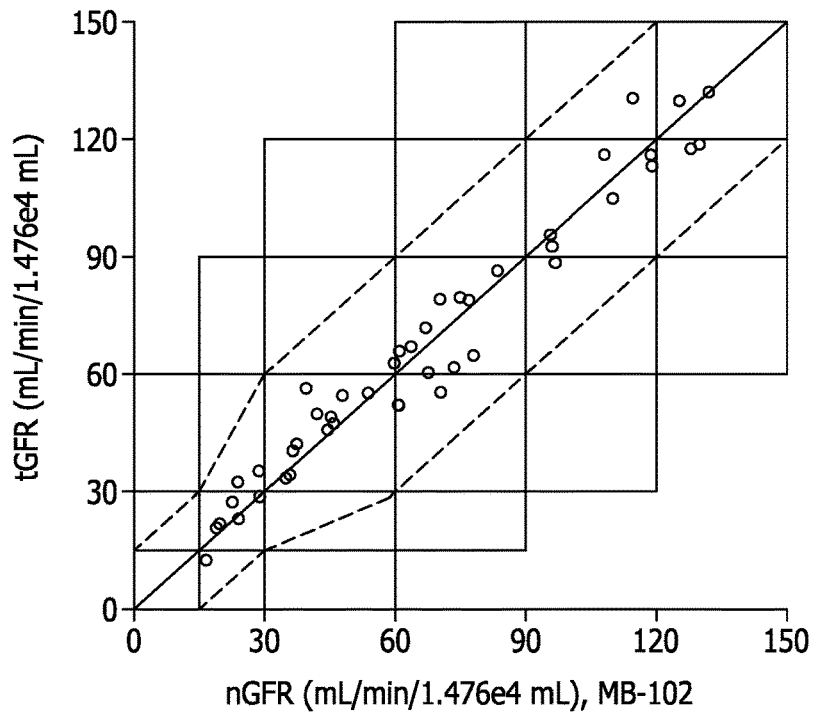

FIG. 29c is a graph of transdermally determined GFR (tGFR) vs. plasma PK-determined GFR, normalized for the volume of distribution of the tracer agent within the subject (nGFR). Superimposed on the graph is an error grid, indicating diagnosis accuracy, by number of CKD stages. Measurements falling within a grid with only green sides would be correctly diagnosed by tGFR. Measurements falling within a grid with both green and yellow sides would be incorrectly diagnosed by tGFR by one CKD stage. Measurements falling within a grid with both yellow and red sides would be incorrectly diagnosed by tGFR by two CKD stages.

Figure 30:
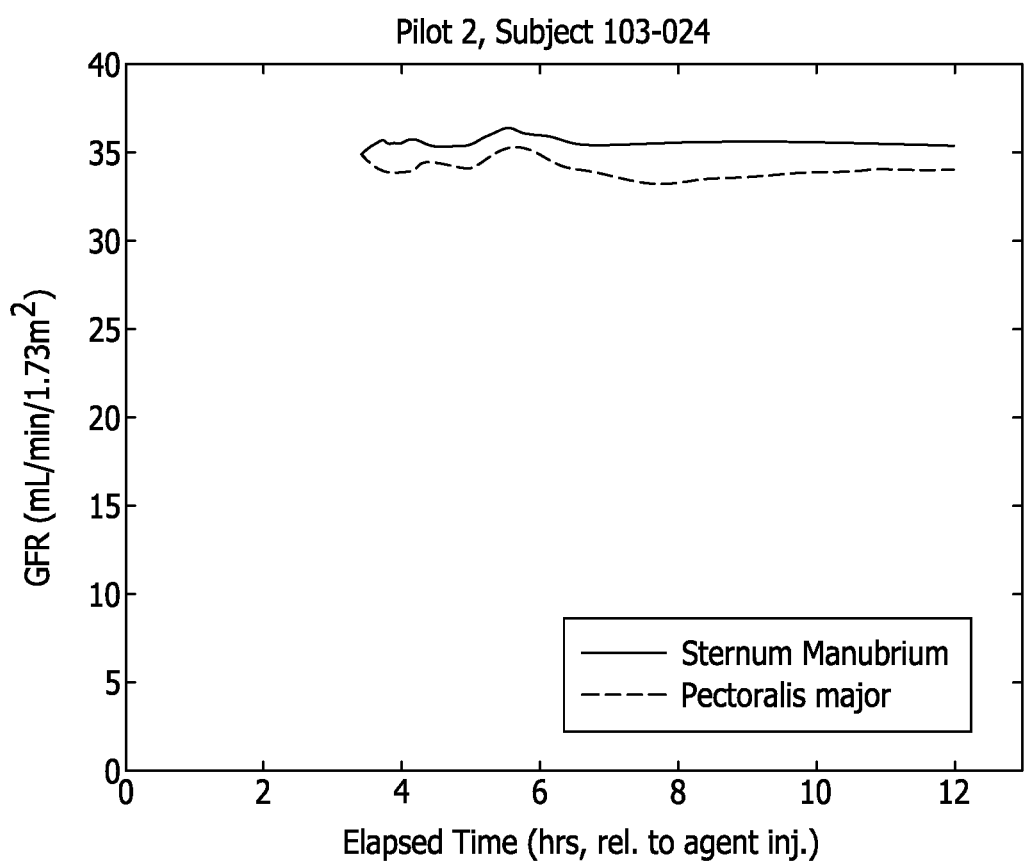

FIG. 30 is a graph of transdermally-measured GFR automatically determined at two body sites in real-time.

DETAILED DESCRIPTION OF THE INVENTION

All references herein to the "pyrazine", "pyrazine derivative", "pyrazine molecule", "pyrazine compound" or "pyrazine analog" apply to all compounds of Formula I. Additionally each reference to the pyrazine includes all pharmaceutically acceptable salts thereof unless specifically stated otherwise. Salt forms may be charged or uncharged, and may be protonated to form the appropriate cation or deprotonated to form the appropriate anion. All aspects and embodiments disclosed herein are applicable to compounds of Formula I, and specific examples are only illustrative and non-limiting to the scope of the disclosure.

In one aspect, disclosed herein is a pyrazine derivative of Formula I, or a pharmaceutically acceptable salt thereof,

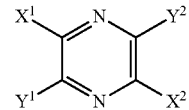

Formula I wherein each of $X^1$ and $X^2$ is independently —$CO_2R^1$, —$CONR^1R^2$, —CO(AA) or —CONH(PS); each of $Y^1$ and $Y^2$ is independently selected from the group consisting of —$NR^1R^2$ and

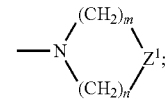

$Z^1$ is a single bond, —$CR^1R^2$—, —O—, —$NR^1$—, —$NCOR^1$—, —S—, —SO—, or —$SO_2$—; each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; AA is a peptide chain comprising one or more amino acids selected from the group consisting of natural and unnatural amino acids, linked together by peptide or amide bonds and each instance of AA may be the same or different than each other instance; PS is a sulfated or non-sulfated polysaccharide chain comprising one or more monosaccharide units connected by glycosidic linkages; and 'a' is a number from 0 to 10, 'c' is a number from 1 to 100, and each of 'm' and 'n' are independently a number from 1 to 3. In another aspect, 'a' is a number from 1 to 10. In still yet another aspect, 'a' is 1, 2, 3, 4, 5, 6, 7, 8, 9 or 10.

In some aspects, at least one of $X^1$ and $X^2$ is —CO(PS) or —CO(AA). In yet another aspect, both $X^1$ and $X^2$ are —CO(AA).

(AA) is a peptide chain comprising one or more natural or unnatural amino acids linked together by peptide or amide bonds. The peptide chain (AA) may be a single amino acid, a homopolypeptide chain or a heteropolypeptide chain, and may be any appropriate length. In some embodiments, the natural or unnatural amino acid is an α-amino acid. In yet another aspect, the α-amino acid is a D-α-amino acid or an L-α-amino acid. In a polypeptide chain comprising two or more amino acids, each amino acid is selected independently of the other(s) in all aspects, including, but not limited to, the structure of the side chain and the stereochemistry. For example, in some embodiments, the peptide chain may include 1 to 100 amino acid(s), 1 to 90 amino acid(s), 1 to 80 amino acid(s), 1 to 70 amino acid(s), 1 to 60 amino acid(s), 1 to 50 amino acid(s), 1 to 40 amino acid(s), 1 to 30 amino acid(s), 1 to 20 amino acid(s), or even 1 to 10 amino acid(s). In some embodiments, the peptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the amino acid is selected from the group consisting of D-alanine, D-arginine D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tryptophan, D-tyrosine, and D-valine. In some embodiments, the α-amino acids of the peptide chain (AA) are selected from the group consisting of arginine, asparagine, aspartic acid, glutamic acid, glutamine, histidine, homoserine, lysine, and serine. In some embodiments, the α-amino acids of the peptide chain (AA) are selected from the group consisting of aspartic acid, glutamic acid, homoserine and serine. In some embodiments, the peptide chain (AA) refers to a single amino (e.g., D-aspartic acid or D-serine).

In some embodiments, (AA) is a single amino acid selected from the group consisting of the 21 essential amino acids. In other aspects, AA is selected from the group consisting of D-arginine, D-asparagine, D-aspartic acid, D-glutamic acid, D-glutamine, D-histidine, D-homoserine, D-lysine, and D-serine. Preferably, AA is D-aspartic acid, glycine, D-serine, or D-tyrosine. Most preferably, AA is D-serine.

In some embodiments, (AA) is a β-amino acid. Examples of β-amino acids include, but are not limited to, β-phenylalanine, β-alanine, 3-amino-3-(3-bromophenyl)propionic acid, 3-aminobutanoic acid, cis-2-amino-3-cyclopentene-1-carboxylic acid, trans-2-amino-3-cyclopentene-1-carboxylic acid, 3-aminoisobutyric acid, 3-amino-2-phenylpropionic acid, 3-amino-4-(4-biphenylyl)butyric acid, cis-3-amino-cyclohexanecarboxylic acid, trans-3-amino-cyclohexanecarboxylic acid, 3 amino-cyclopentanecarboxylic acid, 3-amino-2-hydroxy-4-phenylbutyric acid, 2-(aminomethyl) phenylacetic acid, 3-amino-2-methylpropionic acid, 3-amino-4-(2-naphthyl)butyric acid, 3-amino-5-phenylpentanoic acid, 3-amino-2-phenylpropionic acid, 4-bromo-β-Phe-OH, 4-chloro-β-Homophe-OH, 4-chloro-β-Phe-OH, 2-cyano-β-Homophe-OH, 2-cyano-β-Homophe-OH, 4-cyano-β-Homophe-OH, 3-cyano-β-Phe-OH, 4-cyano-β-Phe-OH, 3,4-dimethoxy-β-Phe-OH, γ,γ-diphenyβ-Homoala-OH, 4-fluoro-β-Phe-OH, β-Gln-OH, β-Homoala-OH, β-Homoarg-OH, β-Homogln-OH, β-Homoglu-OH, β-Homohyp-OH, β-Homoleu-OH, β-Homolys-OH, β-Homomet-OH, β2-homophenylalanine, β-Homophe-OH, β3-Homopro-OH, β-Homoser-OH, β-Homothr-OH, β-Homotrp-OH, β-Homotrp-OMe, β-Homotyr-OH, β-Leu-OH, β-Leu-OH, β-Lys(Z)—OH, 3-methoxy-β-Phe-OH, 3-methoxy-β-Phe-OH, 4-methoxy-β-Phe-OH, 4-methy-β-Homophe-OH, 2-methyl-β-Phe-OH, 3-methyl-β-Phe-OH, 4-methyl-β-Phe-OH, β-Phe-OH, 4-(4-pyridyl)-β-Homoala-OH, 2-(trifluoromethyl)-β-Homophe-OH, 3-(trifluoromethyl)-β-Homophe-OH, 4-(trifluoromethyl)-β-Homophe-OH, 2-(trifluoromethyl)-β-Phe-OH, 3-(trifluoromethyl)-β-Phe-OH, 4-(trifluoromethyl)-β-Phe-OH, β-Tyr-OH, Ethyl 3-(benzylamino)propionate, β-Ala-OH, 3-(amino)-5-hexenoic acid, 3-(amino)-2-methylpropionic acid, 3-(amino)-2-methylpropionic acid, 3-(amino)-4-(2-naphthyl)butyric acid, 3,4-difluoro-β-Homophe-OH, γ,γ-diphenyl-β-Homoala-OH, 4-fluoro-β-Homophe-OH, β-Gln-OH, β-Homoala-OH, β-Homoarg-OH, β-Homogln-OH, β-Homoglu-OH, β-Homohyp-OH, β-Homoile-OH, β-Homoleu-OH, β-Homolys-OH, β-Homomet-OH, β-Homophe-OH, β3-homoproline, β-Homothr-OH, β-Homotrp-OH, β-Homotyr-OH, β-Leu-OH, 2-methyl-β-Homophe-OH, Homophe-OH, β-Phe-OH, 4-(3-pyridyl)-β-Homoala-OH, 3-(trifluoromethyl)-β-Homophe-OH, β-Glutamic acid, β-Homoalanine, β-Homoglutamic acid, β-Homoglutamine, β-Homohydroxyproline, β-Homoisoleucine, β-Homoleucine, β-Homomethionine, β-Homophenylalanine, β-Homoproline, β-Homoserine, β-Homothreonine, β-Homotryptophan, β-Homotyrosine, β-Leucine, β-Phenylalanine, Pyrrolidine-3-carboxylic acid and β-Dab-OH.

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose). In yet another aspect, the polysaccharide chain is an amino sugar where one or more of the hydroxy groups on the sugar has been replaced by an amine group. The connection to the carbonyl group can be either through the amine or a hydroxy group.

In some embodiments, for the pyrazine derivative of Formula I, at least one of either $Y^1$ or $Y^2$ is

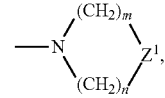

where $Z^1$ is a single bond, —$CR^1R^2$—, —O—, —$NR^1$—, —$NCOR^1$—, —S—, —SO—, or —$SO_2$—; and each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; a, c, m and n are as describe elsewhere herein.

In yet another aspect, at least one of $Y^1$ and $Y^2$ is —$NR^1R^2$, and $R^1$ to $R^2$ are as described above. In yet another aspect, both $Y^1$ and $Y^2$ are —$NR^1R^2$, and $R^1$ to $R^2$ are as described above. Alternatively, $R^1$ and $R^2$ are both independently selected from the group consisting of H, —$CH_2(CHOH)_aCH_3$, —$(CH_2)_aSO_3H$, —$(CH_2)_aNHSO_3H$, and —$(CH_2)_aPO_3H_2$. In yet another aspect, both $R^1$ and $R^2$ are hydrogen.

In any aspect of the pyrazine compound, one or more atoms may alternatively be substituted with an isotopically labelled atom of the same element. For example, a hydrogen atom may be isotopically labelled with deuterium or tritium; a carbon atom may be isotopically labelled with $^{13}C$ or $^{14}C$; a nitrogen atom may be isotopically labelled with $^{14}N$ or $^{15}N$. An isotopic label may be a stable isotope or may be an unstable isotope (i.e., radioactive). The pyrazine molecule may contain one or more isotopic labels. The isotopic label may be partial or complete. For example, a pyrazine molecule may be labeled with 50% deuterium thereby giving the molecule a signature that can be readily monitored by mass spectroscopy or other technique. As another example, the pyrazine molecule may be labeled with tritium thereby giving the molecule a radioactive signature that can be monitored both in vivo and ex vivo using techniques known in the art.

Pharmaceutically acceptable salts are known in the art. In any aspect herein, the pyrazine may be in the form of a pharmaceutically acceptable salt. By way of example and not limitation, pharmaceutically acceptable salts include those as described by Berge, et al. in *J. Pharm. Sci.*, 66(1), 1 (1977), which is incorporated by reference in its entirety for its teachings thereof. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, disuccinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, trometamine, aluminum, calcium, lithium, magnesium, potassium, sodium zinc, barium and bismuth. Any functional group in the pyrazine derivative capable of forming a salt may optionally form one using methods known in the art. By way of example and not limitation, amine hydrochloride salts may be formed by the addition of hydrochloric acid to the pyrazine. Phosphate salts may be formed by the addition of a phosphate buffer to the pyrazine. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

In yet another aspect, disclosed herein is a method for measuring the renal glomerular filtration rate (GFR) in a patient in need thereof. The method comprises administering to a patient a pyrazine compound, or a pharmaceutically acceptable salt thereof, measuring the transdermal fluorescence in said patient over a period of time, and determining the GFR in said patient. The period of time used to determine a single measurement of GFR is referred to herein as the Measurement Time Window. In many situations it will be clinical useful to have a real-time assessment of GFR over time. Therefore, in some aspects of the disclosure, multiple sequential assessments of GFR are provided. In some aspects, the multiple sequential GFR estimates are provided after a single administration of the tracer agent. The total length of time over which GFR measurements are provided after a single injection will be referred to herein as the Single Injection Reporting Period. In some aspects, there is temporal overlap between the Measurement Time Windows. In such cases, the time interval at which GFR is reported (the Reporting Time Interval) is not necessarily the same as the Measurement Time Window. For example, in one embodiment, adjacent Measurement Time Windows overlap by 50%, and the Reporting Time Interval is half of the Measurement Time Window. In some aspects, the Measurement Time Windows have variable length. In a preferred embodiment, if temporally adjacent Measurement Time Windows are of differing length, then the overlap time period is selected to be 50% of the lesser of the two Measurement Time Windows. In some aspects, the GFR of a patient is determined using the system disclosed elsewhere herein.

In yet another aspect, the Measurement Time Window is automatically adjusted according to a metric related to the signal quality (hereafter referred to as a Quality Metric). The Quality Metric may be based on estimates of the fluorescence signal-to-noise ratio (SNR), signal-to-background ratio (SBR), good-of-fit metrics, correlation coefficient, or any combination thereof. In one aspect, a line is fitted to the log of the fluorescence intensity vs. time over the Measurement Time Window (or equivalently, a single exponential is fit to the fluorescence intensify vs. time). The difference between the fitted line and data ("Fitting Residual") is used to estimate the "Noise". In one aspect, the Noise is the root mean square (RMS) of the Fitting Residual. In another aspect, the Noise is the median absolute deviation (MAD) of the Fitting Residual. The "Signal" may be defined as the amplitude of the single exponential derived from the fit. In another aspect, the Signal is chosen as the difference between the fitted fluorescence at the beginning and end of the Measurement Time Window. In another aspect, the pre-injection fluorescence signal level is used to determine a "Background", and the SBR is computed by dividing the Background into the Signal level. When using either the SNR or SBR as the Quality Metric, a minimum threshold may be defined and only if the Quality Metric exceeds this threshold will the fit be considered valid for the purpose of determining GFR. In another aspect, the estimated error of the time or rate constant determined by the fit to fluorescence vs time is used as the Quality Metric. In this case, the fit may be considered valid only if the computed Quality Metric is below a predetermined threshold value. In some other aspects, the fitted time or rate constant is defined as the Signal and the estimated error from the fit is defined as the Noise, and this version of SNR is used as the Quality Metric. In another aspect, a correlation coefficient is used as the Quality Metric. Any of various methods known in the art for computing the correlation coefficient may be employed, such as Pearson's correlation coefficient, or the concordance correlation coefficient. In yet another aspect, a combination of different Quality Metrics are combined into a single metric, or the fitted result is only considered valid for the purpose of determining GFR if all of the selected Quality Metrics are passed.

In another aspect, a minimum Measurement Time Window is defined, and a Quality Metric is used to determine whether to report the GFR, or to extend the length of the Measurement Time Window. In one such embodiment, the length of the Measurement Time Window is automatically increased until the Quality Metric reaches a threshold, at which point the GFR is reported. In another aspect, preliminary fits are used to the time or rate constant, or predicted GFR, and are used to set the Measurement Time Window to a predetermined length. In one embodiment, the minimum Measurement time is set to 60 minutes, at which point a fit is performed and a preliminary estimate of GFR is made. If the preliminary estimate of GFR is equal to above 75 mL/min/1.73 m$^2$, then the result is reported to the user, and the Measurement Time Window is kept at 60 minutes. However, if the preliminary estimated of GFR is below 75 mL/min/1.73 m$^2$, then the result is not reported to the user, and the Measurement Time Window is increased to 120 minutes.

In another aspect, the remaining Single Injection Reporting Period is estimated and provided to the user periodically. The basis for estimating the remaining Single Injection Reporting Period may be the SNR, SBR, or estimated fitting error, such as the methods described above for determining a Quality Metric, but the Quality Metric used to determine the Measurement Time Window and the Quality Metric used to determine the remaining Single Injection Reporting Period may be the same or different. In some aspects, in addition to the Quality Metric, a fitted fluorescence decay time or rate constant is used to estimate the remaining Single Injection Reporting Period. In one embodiment, the fitted fluorescence decay time constant and the SNR are combined to predict the remaining Single Injection Reporting Period. The SNR is scaled to range between minimum and maximum values of 0 and 1, and is multiplied with the fluorescence decay time constant. The product is then scaled to predict the Single Injection Reporting Period. The scaling factor is a calibration factor that is determined through analysis of data collected previously on human patients, animals, in vitro studies, simulations, or any combination thereof.

In yet another aspect, filtering and/or outlier rejection are applied to the fluorescence data before fitting within the Measurement Time Window. Examples of appropriate filters include: a boxcar average, an infinite response function filter, a median filter, a trimmed mean filter. Examples of outlier rejection methods include all of the above Quality Metrics described above, but applied to a subset of the Measurement Tine Window.

In some aspects, the Quality Metric is computed from the measured emission energy of the tracer agent as a function of time over a measurement time window. The Quality Metric may be used to determine whether or not to report the computed GFR. In other aspects, the Quality Metric is used to decide whether to expand the measurement time window. For example, the measurement time window may be automatically expanded until the quality metric passes a predetermined threshold, at which time the GFR is reported.

GFR normalized to patient body size is determined by fitting the measured emission energy of the tracer agent as a function of time over a measurement time window to a decay parameter. In some aspects, this decay parameter is the rate constant (or its inverse, referred to as a time constant) from a single exponential fit. In some aspects the offset of the fitted function is fixed at zero; in other aspects the offset is a variable term in the fit; in yet other aspects, whether the offset is fixed or allowed to vary depends on a preliminary assessment of the decay parameter. The measurement time window is chosen to begin after the tracer agent has equilibrated into the body, during the period when the decay of the emission intensity is due to renal clearance of the tracer agent. The fitted rate constant is multiplied by a calibration slope to determine the GFR normalized to patient body size. The calibration slope is determined through analysis of data collected previously on human patients, animals, in vitro studies, simulations or any combination thereof.

Because the physical size of a patient can affect the assessment of the functioning of the kidneys, in some aspects, a body-size metric is used to normalize the GFR calculation to further improve the measurement. In some aspects, the body-size metric used for normalizing the GFR is body surface area (BSA). In other aspects, the body-size metric is the volume of distribution ($V_d$) of the tracer agent.

The methods and system disclosed herein also permit the real-time monitoring of GFR in a patient. Additionally, multiple GFR measurements or determinations can be done with a single administration of a tracer agent. In some aspects, a single GFR measurement is determined after administration of the tracer agent. In other aspects, multiple GFR measurements are determined after administration of the tracer agent, providing a real-time GFR trend. In some such aspects, an estimate is provided of the time remaining during which the remaining concentration of tracer agent will be sufficient to continue determining GFR.

In yet another aspect, disclosed herein is a method for measuring the renal glomerular filtration rate (GFR) in a patient in need thereof. The method comprises administering to a patient a pyrazine compound, or a pharmaceutically acceptable salt thereof, measuring the transdermal fluorescence in said patient over a Measurement Time Window, and determining the GFR in said patient. In some aspects, the GFR of a patient is determined using the system disclosed elsewhere herein.

In yet another aspect, disclosed herein is a method for determining the GFR in a patient in need thereof. The method comprises administering to said patient a compound of Formula I, or a pharmaceutically acceptable salt thereof, or a pharmaceutically acceptable formulation thereof, measuring the concentration of the compound of Formula I in said patient over a Measurement Time Window, and determining the GFR in said patient.

In some aspects and still in reference to the above mentioned method, measuring the concentration of the pyrazine includes monitoring the transdermal fluorescence in the patient. In yet another aspect, measuring the concentration of the pyrazine includes taking aliquots of blood from the patient and measuring the concentration of the pyrazine by HPLC or other methods as are known it the art. For example, a pyrazine may incorporate a radioisotope that can be quantified. In still yet another aspect, measuring the concentration of the pyrazine may including collecting the urine of the patient over a period of time to determine the rate in which the kidneys eliminate the compound from the body of the patient.

In still yet another aspect and still in reference to the above mentioned method, the concentration of the pyrazine in the patient is monitored by transdermal fluorescence. This may include contacting a medical device with the skin of the patient wherein said medical device is configured to cause a fluorescent reaction in the compound of Formula I, and detecting said reaction. The medical device may contact the skin of the patient in any suitable location. Specific locations known to be suitable are the sternum, lower sternum, pectoralis major, occipital triangle, forehead, chin, upper hip, and lower hip. Other locations on a patient may be used as determined by convenience, medical device design, and/or medical necessity. In some aspects, this method uses the system disclosed elsewhere herein.

In one aspect of the above-mentioned method, a display is used to prompt the user to attach the sensor at one or more particular body sites. In one such embodiment, a touch-screen interface is used, and the user is instructed to touch a rendition of the body site location at which the sensor was attached, in order to move to a next step in the measurement setup process. This has the benefit of discouraging placement of the sensor on body sites that are not appropriate or optimal for the GFR determination.

In another aspect, the next step is setting the light source output levels and the detector gain levels. In one such aspect, the detector gain levels and light source levels are both initially set to a low state and then the light source levels are sequentially increased until a targeted signal level is achieved. In one embodiment, the light source is the excitation source for the fluorescent GFR agent, and the source drive current is increased until either a targeted fluorescence signal is achieved or a predefined maximum current is reached. In the case that the maximum source current is reached without attaining the desired fluorescence signal level, the detector gain is then sequentially increased until either the targeted fluorescence signal is achieved, or the maximum detector gain setting is reached.

In some aspects, measurement of the diffuse reflectance of the skin is made in addition to measurement of fluorescence of the skin and GFR agent. In such aspects, the diffuse reflectance signal may be used to determine the optimum source output and detector gain levels. In yet further aspects, diffuse reflectance measurements are made within the wavelength bands for excitation and emission of the fluorescent GFR agent. In such aspects, setting of the LED source levels and detector gains may be performed by using the diffuse reflectance instead of the fluorescence signal levels to guide the settings. In one such aspect, the target levels or the diffuse reflectance signals are between 15% and 35% of the signal level at which detector or amplifier saturation effects are observed. This provides head-room for signal fluctuations that may be associated with patient movement or other physiological variation. The described procedures for optimizing the light source output and/or detection gains have the benefit that they provide a means of compensating for physiological variations across different patients, or across different body sites on the same patient. In one aspect, a primary factor that is compensated is the melanin content of the skin. Other physiological factors that may require compensation include blood content, water content, and scattering within the tissue volume that is optically interrogated by the sensor. In another aspect, if the desired signal targets are not attained, the user is prevented from proceeding with the measurement. In this manner, the reporting of inaccurate results is prevented.

Once the desired signal levels have been successfully achieved, in another aspect, a baseline signal is recorded. In one such aspect, the stability of the baseline is assessed, such as by fitting a slope to the signal over time, and the baseline is not accepted as valid unless the slope over time is below a pre-determined threshold. In some aspects, a display instructs the user not to proceed with administration of the tracer agent until a stable baseline has been achieved. In this manner, measurement is prevented if the sensor has not been properly positioned or attached. In addition, the user may be prevented from proceeding with a measurement if the tracer agent from a prior injection has not cleared out of the body yet to a desired degree.

Once a stable baseline is acquired, in another aspect of the above-mentioned method, the tracer agent is injected into the vascular space of the patient. The tracer agent administration is automatically detected as a rapid increase in the transdermal fluorescence of the patient as measured by the one or more sensors. A predetermined threshold for the rate of change, absolute signal change, or relative signal change may be employed for this purpose. The automatic agent detection may be reported to the user on a display device, such as a touch-screen monitor. In another aspect, once the tracer agent is detected, a further threshold is used to determine if sufficient tracer agent is present to initiate a GFR measurement. In one such aspect, measurements of fluorescence ($F_{meas}$) and diffuse reflectance (DR) are combined in a manner which reduces the influence of physiological variation on the combined result (herein referred to as the Intrinsic Fluorescence or IF), so that, for example, the influence of skin color on the measurement is compensated for. The sufficiency of the tracer agent is then assessed by comparing the IF to a pre-determined threshold. In some aspects the IF is determined by using a formula of the form:

$$IF = \frac{F_{meas}}{DR_{ex}^{k,ex} DR_{em}^{kem} DR_{em,filtered}^{kem,filtered}} \qquad \text{Equation (1)}$$

where the subscripts on the DR terms refer to measurements collected within the tracer agent excitation (ex) and emission (em) wavelength bands, with both filtered and un-filtered detectors, and the superscripts on the DR terms are calibration coefficients that may be determined through analysis of data collected previously on human patients, animals, in vitro studies, simulations, or any combination thereof. In this manner, if insufficient tracer agent has been administered for an accurate GFR assessment, the medical professional administering the measurement may be provided the opportunity to administer additional tracer agent, or to discontinue the measurement.

Once the tracer agent has been administered, in another aspect, the equilibration of the tracer agent into the extra-cellular space is monitored. In one aspect, the Measurement Time Window does not start until it has been determined that equilibration is sufficiently complete. A fit to an exponential function may be used to assess equilibration progress. For example, the change in fluorescence intensity over time may be fit to a single exponential function, and only once the fitted time constant is stable, is equilibration deemed to be complete. In one such aspect, a running estimate of when the first GFR determination will become available is provided to the user. In another aspect, the user is prevented from proceeding to the measurement phase until and unless sufficient equilibration has been achieved. In one such aspect, the equilibration time is compared to a predetermined threshold, and if the equilibration time exceeds the threshold, the user is prevented from proceeding with GFR determination. In this manner, if the sensor is located in a site that is in poor exchange with the circulatory system, the assessment of GFR is prevented.

In some aspects, the Reporting Time Interval, Measurement Time Window, and/or Single Injection Reporting Period are based on the specific medical assessment being performed and may vary accordingly. For example, for patients with chronic kidney failure, a single GFR determination may be sufficient. However, for patients with or at risk of acute kidney failure, a real-time assessment or GFR trend provides great potential benefit. In some aspects said Reporting Time Interval will be approximately 15 minutes. In other aspects said Reporting Time Interval will be approximately 30 minutes, approximately one hour, approximately two hours, approximately three hours, approximately five hours, approximately eight hours, approximately 10 hours, approximately 12 hours, approximately 18 hours, approximately 24 hours, approximately 36 hours, approximately 48 hours, approximately 72 hours, approximately 96 hours, or approximately 168 hours. In some aspects the Reporting Time Interval will be between 15 minutes and 168 hours. In some aspects the Single Injection Reporting Period will be based on the clearance half-life of the pyrazine compound. Said clearance half-life can be either previously determined in said patient, estimated based on the medical condition of said patient, or determined transdermally using the methods described herein. In some aspects said Single Injection Reporting Period is one clearance half-life, two clearance half-lives, three clearance half-lives, four clearance half-lives, five clearance half-lives, six clearance half-lives, eight clearance half-lives, or ten clearance half-lives. The maximum Single Injection Reporting Period is such that the pyrazine is no longer detectable in the blood stream of said patient. "Undetectable" as used herein means that the concentration of the pyrazine is no longer detectable by the method used to make the determination. In some instances, when the detection level of the instrument makes this an extremely long time period (e.g., over one week), "undetectable" means that the concentration level has dropped below 0.39% (i.e., eight clearance half-lives). In yet another aspect, the Reporting Time Interval is between approximately 1 and 168 hours and all one hour increments in between.

Likewise, the Measurement Time Window may vary according to the specific medical needs of the patient and may vary accordingly. In some aspects it will be approximately 15 minutes. In other aspects said Measurement Time Window will be approximately 30 minutes, approximately one hour, approximately two hours, approximately three hours, approximately five hours, approximately eight hours, approximately 10 hours, approximately 12 hours, approximately 18 hours, approximately 24 hours, approximately 36 hours, approximately 48 hours, approximately 72 hours, approximately 96 hours, or approximately 168 hours. In some aspects the Measurement Time Window will be between 15 minutes and 168 hours. There may be one or a plurality of Measurement Time Windows during each Single Injection Reporting Period. In some aspects, the Single Injection Reporting Period is divided into multiple Measurement Time Windows where each Measurement Time Window is the same. In yet another aspect, the Single Injection Reporting Period is divided into multiple Measurement Time Windows where each Measurement Time Windows is selected independently of the others and may be the same or different than the other Measurement Time Windows.

The methods and system disclosed herein have the benefit of automatically adjusting for skin melanin content, such that the GFR determination is accurate across a wide range of skin types and levels of pigmentation. The Fitzpatrick scale is a numerical classification scheme for human skin color. It is widely recognized as a useful tool for dermatological research into human skin pigmentation. Scores range from type I (very fair skin with minimal pigmentation) to type VI (deeply pigmented and dark brown). The system and methods disclosed herein are suitable for use with all six categories of skin pigmentation on the Fitzpatrick scale. Specifically, the systems and methods disclosed herein are suitable for use with skin pigmentation of type I, type II, type III, type IV, type V and type VI.

In yet another aspect, the pyrazine is combined with at least one pharmaceutically acceptable excipient. Said pharmaceutically acceptable excipients are selected from the group consisting of solvents, pH adjusting agents, buffering agents, antioxidants, tonicity modifying agents, osmotic adjusting agents, preservatives, antibacterial agents, stabilizing agents, viscosity adjusting agents, surfactants and combinations thereof.

Pharmaceutically acceptable solvents may be aqueous or non-aqueous solutions, suspensions, emulsions, or appropriate combinations thereof. Non-limiting examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media.

By way of example and not limitation, pharmaceutically acceptable buffers include acetate, benzoate, carbonate, citrate, dihydrogen phosphate, gluconate, glutamate, glycinate, hydrogen phosphate, lactate, phosphate, tartrate, Tris.HCl, or combinations thereof having a pH between 4 and 9, preferably between 5 and 8, most preferably between 6 and 8, very most preferably between 7.0 and 7.5. In yet another aspect, the pH is between 6.7 and 7.7. Other buffers, as are known in the art, may be selected based on the specific salt form of the pyrazine derivative prepared or the specific medical application. A preferred buffer is phosphate buffered saline at physiological pH (approximately 7.2).

Examples of the tonicity modifying agent are glycerol, sorbitol, sucrose, or, preferably, sodium chloride and/or mannitol. Examples of the viscosity adjusting agent include bentonite, calcium magnesium silicate and the like. Examples of the diluent include ethanol, methanol and the like. Examples of the antimicrobial include benzalkonium chloride, benzethonium chloride, ethylparaben, methylparaben and the like. Examples of osmotic adjusting agents include aminoethanol, calcium chloride, choline, dextrose, diethanolamine, lactated Ringer's solution, meglumine, potassium chloride, Ringer's solution, sodium bicarbonate, sodium chloride, sodium lactate, TRIS, or combinations thereof. These examples are for illustration only and are not intended to be exhaustive or limiting.

Also disclosed herein is a method of assessing the renal function in a patient in need thereof, said method comprises administering a compound of Formula I, or a pharmaceutically acceptable salt thereof, or a pharmaceutically acceptable formulation thereof, to a patient, exposing said patient to electromagnetic radiation thereby causing spectral energy to emanate from said compound of Formula I, detecting the spectral energy emanated from the compound, and assessing the renal function of the patient based on the detected spectral energy.

In some aspects, the compound of Formula I is not metabolized by the patient; instead it is entirely eliminated by renal excretion without being metabolized (e.g., no oxidation, glucuronidation or other conjugation). In some aspects, at least 95% of the compound of Formula I is not metabolized by the patient prior to renal excretion. In some aspects, at least 96% of the compound of Formula I is not metabolized by the patient prior to renal excretion. In some aspects, at least 97% of the compound of Formula I is not metabolized by the patient prior to renal excretion. In some aspects, at least 98% of the compound of Formula I is not metabolized by the patient prior to renal excretion. In some aspects, at least 99% of the compound of Formula I is not metabolized by the patient prior to renal excretion. In some embodiments, said compound is entirely eliminated by said patient in less than a predetermined period of time. In some aspects, assessing the renal function in a patient may also include determining the GFR in the patient.

The pyrazine can be administered by any suitable method. The method will be based on the medical needs of the patient and selected by the medical professional administering the pyrazine or conducting the procedure. Examples of administration methods include, but are not limited to, transdermal, oral, parenteral, subcutaneous, enteral or intravenous administration. Preferably the pyrazine compound will be administered using intravenous or transdermal methods. In some embodiments, the pyrazine is administered via a single bolus intravenous injection. In yet another embodiment, the pyrazine is administered by multiple bolus intravenous injections. As used herein, transcutaneous and transdermal both refer to administration through the skin of a patient and are used interchangeably.

As used herein, "enteral administration" refers to any method of administration that delivers a medicament directly or indirectly to the patient using the gastrointestinal tract. Examples of enteral administration include, but are not limited to, oral, sublingual, buccal and rectal. As used herein, "parenteral administration" refers to any method of administration that delivers a medicament directly or indirectly to the patient by injection or infusion. Examples or parenteral administration include, but are not limited to, intravenous, intraarterial, intradermal, transdermal, subcutaneous and intramuscular.

Also disclosed herein is a stable, parenteral composition comprising a pyrazine derivative of Formula I and a pharmaceutically acceptable buffering agent. The composition has a tonicity suitable for administration to a patient via parenteral administration. The tonicity of the parenteral composition may be adjusted using a tonicity adjusting agent as described elsewhere herein. The composition has a pH suitable for administration to a patient in need thereof and may be adjusted using a buffer or other pH adjusting agent as described elsewhere herein. The composition has an osmolarity suitable for administration to a patient in need thereof, and the osmolarity of the composition may be adjusted using an osmolarity adjusting agent as described elsewhere herein. The composition is packaged in a sealed container and subjected to terminal sterilization to reduce or eliminate the microbiological burden of the formulation. The composition is stable against degradation and other adverse chemical reactions, and possesses a pharmaceutically-acceptable shelf-life.

"Stable", as used herein, means remaining in a state or condition that is suitable for administration to a patient. Formulations according to the present disclosure are found to be stable when maintained at room temperature for at least 12 months, and are generally stable at room temperature for 12 to 24 months.

A "sterile" composition, as used herein, means a composition that has been brought to a state of sterility and has not been subsequently exposed to microbiological contamination, i.e. the container holding the sterile composition has not been compromised. Sterile compositions are generally prepared by pharmaceutical manufacturers in accordance with current Good Manufacturing Practice ("cGMP") regulations of the U.S. Food and Drug Administration. In some aspects, the composition is packaged in a heat sterilized container. The container may be any container suitable for use in a medical setting, examples include, but are not limited to, a vial, an ampule, a bag, a bottle and a syringe.

In some embodiments, the composition can take the form of a sterile, ready-to-use formulation for parenteral administration. This avoids the inconvenience of diluting a concentrated parenteral formulation into infusion diluents prior to infusion or injection, as well as reducing the risk of microbiological contamination during aseptic handling and any potential calculation or dilution error. Alternatively, the formulation may be a solid formulation that is diluted prior to administration to the patient.

The aqueous, sterile pharmaceutical composition disclosed herein is suitable for parenteral administration to a patient in need thereof. For example, the composition may be administered in the form of a bolus injection or intravenous infusion. Suitable routes for parenteral administration include intravenous, subcutaneous, intradermal, intramuscular, intraarticular, and intrathecal. The ready-to-use formulation disclosed herein is preferably administered by bolus injection. In some embodiments, the composition is suitable for transdermal delivery into the epidermis or dermis of a patient. Transdermal delivery methods and devices are known in the art and use a variety of methods to deliver the pharmaceutical composition to the patient.

The aqueous, sterile pharmaceutical composition is formulated in combination with one or more pharmaceutically acceptable excipients as discussed elsewhere herein. The aqueous, sterile pharmaceutical composition is formulated such that it is suitable for administration to a patient in need thereof. The tonicity, osmolarity, viscosity and other parameters may be adjusted using agents and methods as described elsewhere herein.

In yet another aspect, disclosed herein is an aqueous, sterile pharmaceutical composition for parental administration. The composition comprises from about 0.1 to 50 mg/mL of a pyrazine compound of Formula I. It also comprises from about 0.01 to 2 M buffering agent as disclosed elsewhere herein. It also comprises from about 0-500 mg/mL of an osmotic-adjusting agent and from about 0-500 mg/mL of a tonicity-adjusting agent. The aqueous, sterile pharmaceutical composition may also optionally include one or more additional pharmaceutically acceptable excipients. Examples of pharmaceutically acceptable excipients may be selected from the group consisting of solvents, pH adjusting agents, buffering agents, antioxidants, tonicity modifying agents, osmolarity adjusting agents, preservatives, antibacterial agents, stabilizing agents, viscosity adjusting agents, surfactants and combinations thereof. Specific examples of excipients are disclosed elsewhere herein.

The pyrazine compound used in the aqueous, sterile pharmaceutical composition is any compound disclosed herein. Specific examples include, but are not limited to, all of the compounds prepared in the Examples. One preferred example is (2R,2'R)-2,2'-((3,6-diaminopyrazine-2,5-dicarbonyl)bis(azanediyl))bis (3-hydroxy-propanoic acid) which is the molecule illustrated in Example 12 (also identified as MB-102 or 3,6-Diamino-$N^2$,$N^5$-bis (D-serine)-pyrazine-2,5-dicarboxamide).

The pH of the aqueous, sterile pharmaceutical composition is suitable for administration to a patient. In some aspects the pH is between 4 and 9, preferably between 5 and 8, most preferably between 6 and 8, very most preferably between 7.0 and 7.5. In yet another aspect, the pH is between 6.7 and 7.7. Still more preferably, the pH is approximately 7.2 in phosphate buffered saline.

In some aspects, the pyrazine is administered to a patient suspected or known to have at least one medical issue with their kidneys, and the methods disclosed herein are used to determine the level of renal impairment or deficiency present in said patient. In some aspects, said patient has an estimated GFR (eGFR) or previously determined GFR of less than 110, less than 90, less than 60, less than 30, or less than 15. The eGFR of a patient is determined using standard medical techniques, and such methods are known in the art. In some aspects a patient will not have or be suspected to have medical issues with their kidneys. The GFR monitoring may be done as part of a general or routine health assessment of a patient or as a precautionary assessment.

As is known in the art, the rate in which a patient eliminates waste from their blood stream (i.e., clearance half-life) is dependent on the health and proper functioning of their renal system. "Entirely eliminated" as used in this context means that the level of they pyrazine in the blood stream has dropped below 0.39% (i.e., eight half-lives). The clearance half-life will depend on the GFR of the patient and slows greatly as the functioning of the renal system degrades due to illness, age or other physiological factors. In a patient with no known risk factors associated with CKD, having a normal GFR and/or a normal eGFR, the Single Injection Reporting Period is 24 hours. In some aspects, the Single Injection Reporting Period for a patient with a GFR or eGFR below 110 is 24 hours. For a patient with a GFR or eGFR below 90, the Single Injection Reporting Period is 24 hours. For a patient with a GFR or eGFR below 60, the Single Injection Reporting Period is 48 hours. For a patient with a GFR or eGFR below 30, the Single Injection Reporting Period is 48 hours. In some aspects, the Single Injection Reporting Period for a patient with a GFR or eGFR below 110 is equal to eight clearance half-lives. For a patient with a GFR or eGFR below 90, the Single Injection Reporting Period is equal to eight clearance half-lives. For a patient with a GFR or eGFR below 60, the Single Injection Reporting Period is equal to eight clearance half-lives. For a patient with a GFR or eGFR below 30, the Single Injection Reporting Period is equal to eight clearance half-lives.

Because an increase of protein concentration in the urine of a patient may suggest some manner of kidney impairment or deficiency, the methods disclosed herein are suitable for patients whose urinalysis shows an increase in protein levels. In some aspects, the patient has an increased level of protein in their urine as determined by standard medical tests (e.g., a dipstick test). By way of example and not limitation, the urinalysis of a patient may show an increase in albumin, an increase in creatinine, an increase in blood urea nitrogen (i.e., the BUN test), or any combination thereof.

Still referring to the above-mentioned method, the pyrazine derivative is exposed to electromagnetic radiation such as, but not limited to, visible, ultraviolet and/or infrared light. This exposure of the pyrazine to electromagnetic radiation may occur at any appropriate time but preferably occurs while the pyrazine derivative is located inside the body of the patient. Due to this exposure of the pyrazine to electromagnetic radiation, the pyrazine emanates spectral energy (e.g., visible, ultraviolet and/or infrared light) that may be detected by appropriate detection equipment. The spectral energy emanated from the pyrazine derivative tends to exhibit a wavelength range greater than a wavelength range absorbed. By way of example but not limitation, if an embodiment of the pyrazine derivative absorbs light of about 440 nm, the pyrazine derivative may emit light of about 560 nm.

Detection of the pyrazine (or more specifically, the spectral energy emanating therefrom) may be achieved through optical fluorescence, absorbance or light scattering techniques. In some aspects, the spectral energy is fluorescence. In some embodiments, detection of the emanated spectral energy may be characterized as a collection of the emanated spectral energy and the generation of an electrical signal indicative of the collected spectral energy. The mechanism(s) utilized to detect the spectral energy from the pyrazine derivative present in the body of a patient may be designed to detect only selected wavelengths (or wavelength ranges) and/or may include one or more appropriate spectral filters. Various catheters, endoscopes, ear clips, hand bands, head bands, surface coils, finger probes and other medical devices may be utilized to expose the pyrazine derivative to electromagnetic radiation and/or to detect the spectral energy emanating therefrom. The device that exposes the pyrazine to electromagnetic radiation and detects the spectral energy emanated therefrom may be the same or different. That is, one or two devices may be used. The detection of spectral energy may be accomplished at one or more times intermittently or may be substantially continuous.

Renal function, or GFR, of the patient is determined based on the detected spectral energy. This is achieved by using data indicative of the detected spectral energy and generating an intensity/time profile indicative of a clearance of the pyrazine derivative from the body of the patient. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) in order to assess renal function. Alternatively, the patient's clearance profile can be compared to one or more previously measured clearance profiles from the same patient to determine if the kidney function of said patient has changed over time. In some aspects, renal function assessment is done using the system disclosed elsewhere herein.

Physiological function can be assessed by: (1) comparing differences in manners in which normal and impaired cells or organs eliminate the pyrazine derivative from the bloodstream; (2) measuring a rate of elimination or accumulation of the pyrazine in the organs or tissues of a patient; and/or (3) obtaining tomographic images of organs or tissues having the pyrazine associated therewith. For example, blood pool clearance may be measured non-invasively from surface capillaries such as those in an ear lobe or a finger, or it can be measured invasively using an appropriate instrument such as an endovascular catheter. Transdermal fluorescence can also be monitored non-invasively on the body of said patient. Many locations on the epidermis of a patient may be suitable for non-invasively monitoring the transdermal fluorescence. The site on the patient is preferably one where vasculature to tissue equilibrium occurs relatively quickly. Examples of suitable sites on a patient include, but are not limited to, the sternum, the lower sternum, pectoralis major, the occipital triangle, the forehead, the chin, the upper hip, and the lower hip. Accumulation of a pyrazine derivative within cells of interest can be assessed in a similar fashion.

A modified pulmonary artery catheter may also be utilized to, inter alia, make the desired measurements of spectral energy emanating from the pyrazine derivative. The ability for a pulmonary catheter to detect spectral energy emanating from said pyrazine is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, a modified pulmonary artery catheter incorporates a wavelength-specific optical sensor into a tip of a standard pulmonary artery catheter. This wavelength-specific optical sensor is utilized to monitor renal function-specific elimination of a designed optically detectable chemical entity such as the pyrazine derivatives disclosed herein. Thus, real-time renal function can be monitored by the disappearance/clearance of an optically detected compound.

In some aspects, the pyrazine compound is administered to a patient wherein said patient has been previously diagnosed with at least Stage 1 CKD. In other aspects, said patient has been previously diagnosed with Stage 2 CKD, Stage 3 CKD, Stage 4 CKD or Stage 5 CKD. In yet another aspect, the patient has not yet been diagnosed with CKD but has one or more risk factors associated with CKD. In yet another aspect, the patient has no known risk factors for CKD.

Administration of the pyrazine compound is done by any suitable method based on the medical test being performed and the medical needs of the patient. Suitable methods are disclosed elsewhere herein. Preferably, the pyrazine is administered by either transdermal or intravenous administration.

Also disclosed herein is a system for determining the GFR or assessing the renal function in a patient in need thereof. The system comprises a computing device, a display device communicatively coupled to said computing device, a power supply that is operatively coupled to said computing device and maintains electrical isolation of the system from external power sources, one or more sensor heads operatively coupled to said computing device, and at least one tracer agent configured to emit light when exposed to electromagnetic radiation. The computing device is configured to operate and control the sensor heads, record one or more light measurements sent from said sensor heads, and calculate the GFR of said patient based on said light measurements.

In some aspects, the one or more sensor heads comprise at least one source of electromagnetic radiation, generate and deliver electromagnetic radiation to the skin of said patient, detect and measure electromagnetic radiation emitted by said tracer agent, and transmit said measurement of electromagnetic radiation emitted by said tracer agent to said computing device. In a system with more than one sensor head, each sensor head may be the same or different and the electromagnetic radiation emitted therefrom may be the same or different. In some aspects the sensor heads are configured to attach to the skin of said patient. By way of example and not limitation, in a system with two sensor heads, one sensor head may emit and monitor one wavelength of electromagnetic radiation while the second sensor head may emit and monitor a different wavelength. This would enable the data to be compared to increase the accuracy of the GFR determination and the information available to the medical professional administering the assessment. In yet another nonlimiting example, in a system with two sensor heads, the two sensor heads are used to separate the local equilibration kinetics from the terminal phase kinetics. This enables a medical professional to determine when equilibration is complete and reduces artifacts due to local movement of the sensors.

In some aspects, the tracer agent is configured to be administered to said patient via intravenous or transdermal administration, be eliminated by only glomerular filtration in the kidneys of said patient, and emit light that is detectable by said sensor heads when exposed to electromagnetic radiation. In some aspects, the tracer agent is a pyrazine compound of Formula I as disclosed elsewhere herein. Preferably the tracer agent is a compound prepared in one of the Examples. Most preferably, the tracer agent is (2R,2'R)-2,2'-((3,6-diaminopyrazine-2,5-dicarbonyl)bis(azanediyl)) bis (3-hydroxypropanoic acid) (also called MB-102 or 3,6-diamino-$N^2$,$N^5$-bis(D-serine)-pyrazine-2,5-dicarboxamide). In some aspects, the tracer agent is the pyrazine derivative in a formulation suitable for administration to a patient in need thereof. Such formulations are described elsewhere herein.

The system for determining the GFR or assessing the renal function in a patient may be configured to carry out the methods disclosed herein on a patient in need thereof. The computing device in the system may be any standard computer having all of the capabilities implied therewith, specifically including, but not limited to, a permanent memory, a processor capable of complex mathematical calculations, a keyboard and/or a mouse for interacting with the computer, and a display communicatively coupled to the computing device. As such, the permanent memory of the computing device may store any information, programs and data necessary to carry out the functions of the system for determining the GFR or assessing the renal function in a patient. Such information, programs, and data may be standards and/or controls which may be used to compare transdermal fluorescence values collected by the one or more sensor heads to known values. In some aspects, the computing device may save results from a previous assessment or GFR determination in a patient so that results obtained at a later date may be compared. This would permit a medical professional to monitor the health of the kidneys of a patient over time. In some aspects, the computing device is a laptop computer. In some aspects, the display device includes a touch screen.

Additionally, the computing device is configured to calculate the time constant for renal decay over a predetermined period of time. In one aspect, the transdermal fluorescence data in a patient is collected over a predetermined period of time, and a graph is prepared of time (x-axis) versus fluorescence (y-axis). The rate of decay may be curved or linear and a time constant for the rate of decay is calculated. In one aspect, the rate of decay is linear for a semilog(y) plot. The time constant is compared to known values thereby determining the GFR in the patient. In some aspects, the rate of decay corresponds to standard first order kinetics. In yet another aspect, the rate of decay may exhibit a multi-compartment pharmacokinetic model. FIGS. 3A to 3D illustrate two-compartment pharmacokinetics by which standard pharmacokinetic software is able to determine the time constant for renal decay.

GFR determination is done using linear regression, outlier exclusion, calculation of the correlation coefficient ($R^2$) and standard error of calibration and more fully described in the Examples.

This written description uses examples to disclose the invention, including the best mode, and also to enable any person skilled in the art to practice the invention, including making and using any devices or systems and performing any incorporated methods. Any aspect or embodiment disclosed herein may be used in combination with any other aspect or embodiment as would be understood by a person skilled in the art. Other examples are intended to be within the scope of the claims if they have structural elements that do not differ from the literal language of the claims, or if they include equivalent structural elements with insubstantial differences from the literal languages of the claims.

Example 1

Preparation of 3,6-diamino-$N^2,N^2,N^5,N^5$-tetrakis(2-methoxyethyl)pyrazine-2,5-dicarboxamide

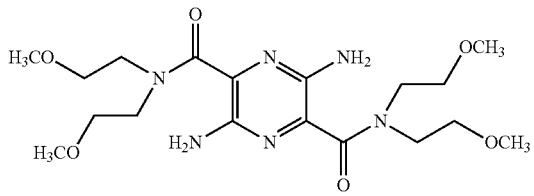 [SMILES: COCCN(CCOC)C(=O)c1nc(N)c(C(=O)N(CCOC)CCOC)nc1N]

A mixture of 3,6-diaminopyrazine-2,5-dicarboxylic acid (200 mg, 1.01 mmol), bis-2-(methoxyethyl)amine (372 µL, 335.5 mg, 2.52 mmol), HOBt.H$_2$O (459 mg, 3.00 mmol), and EDC.HCl (575 mg, 3.00 mmol) were stirred together in DMF (20 mL) for 1 h at room temperature. The mixture was concentrated to dryness and the residue was partitioned with EtOAc and water. The layers were separated and the EtOAc solution was washed with saturated NaHCO$_3$ and brine. The solution was dried over anhydrous Na$_2$SO$_4$, filtered and concentrated. Purification by radial flash chromatography (SiO$_2$, 10/1 CHCl$_3$-MeOH) afforded 228.7 mg (53% yield) of Example 1 as an orange foam: $^1$H NMR (300 MHz, CDCl$_3$), δ 4.92 (s, 4H), 3.76 (apparent t, J=5.4 Hz, 4H), 3.70 (apparent t, J=5.6 Hz, 4H), 3.64 (apparent t, J=5.4 Hz, 4H), 3.565 (apparent t, J=5.4 Hz), 3.67 (s, 6H), 3.28 (s, 6H). $^{13}$C NMR (75 MHz, CDCl$_3$) δ 167.6 (s), 145.6 (s), 131.0 (s), 72.0 (t), 70.8 (t), 59.2 (q), 49.7 (t), 47.1 (t). LCMS (5-95% gradient acetonitrile in 0.1% TFA over 10 min), single peak retention time=3.14 min on 30 mm column, (M+H)$^+$=429. UV/vis (100 µM in PBS) $\lambda_{abs}$=394 nm. Fluorescence (100 nm) $\lambda_{ex}$=394 nm $\lambda_{em}$=550 nm.

Example 2

3,6-diamino-$N^2,N^5$-bis(2,3-dihydroxypropyl)pyrazine-2,5-dicarboxamide

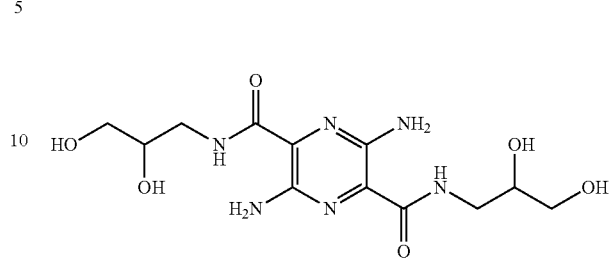

Step 1. Synthesis of 3,6-diamino-$N^2,N^5$-bis((2,2-dimethyl-1,3-dioxolan-4-yl)methyl)pyrazine-2,5-dicarboxamide

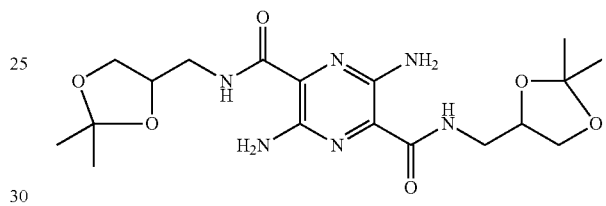

A mixture of 3,6-diaminopyrazine-2,5-dicarboxylic acid (350 mg, 1.77 mmol), racemic (2,2-dimethyl-1,3-dioxolan-4-yl)methanamine (933 µL, 944 mg, 7.20 mmol), HOBt.H$_2$O (812 mg, 5.3 mmol), and EDC.HCl (1.02 g, 5.32 mmol) were stirred together in DMF (20 mL) for 16 h at room temperature. The mixture was concentrated to dryness and the residue was partitioned with EtOAc and water. The layers were separated and the EtOAc solution was washed with saturated NaHCO$_3$ and brine. The solution was dried over anhydrous Na$_2$SO$_4$, filtered and concentrated to afford 665 mg (88% yield) of the bis-amide diastereomeric pair as a yellow solid: $^1$NMR (300 MHz, CDCl$_3$) δ 8.38 (t, J=5.8 Hz, 2H), 6.55 (s, 4H), 4.21 (quintet, J=5.8 Hz, 2H), 3.98 (dd, J=8.4 Hz, 6.3 Hz, 2H), 3.65 (dd, J=8.4 Hz, J=5.8 Hz, 2H), 3.39 (apparent quartet—diastereotopic mixture, J=5.9 Hz, 4H), 1.35 (s, 6H), 1.26 (s, 6H). $^{13}$C NMR (75 MHz, CDCl$_3$) δ 165.7 (s), 146.8 (s), 126.8 (s), 109.2 (s), 74.8 (d), 67.2 (t), 42.2, 41.1 (t—diastereotopic pair), 27.6 (q), 26.1 (q).

Step 2

The product from Step 1 was dissolved in THF (100 mL) and treated with 1.0 N HCl (2 mL). After hydrolysis was complete, the mixture was treated with K$_2$CO$_3$ (1 g) and stirred for 1 h and filtered through a plug of C18 with using methanol. The filtrate was concentrated to dryness and the residue was triturated with MeOH (50 mL). The solids were filtered and discarded and the residue was treated with ether (50 mL). The precipitate was collected by filtration and dried at high vacuum. This material was purified by radial flash chromatography to afford 221 mg (36% yield) of Example 2 as an orange solid: $^1$NMR (300 MHz, DMSO-d$_6$) δ 8.00 (bm, 6H), 5.39 (bs, 2H), 4.88 (bs, 2H), 3.63-3.71 (complex m, 2H), 3.40 (dd, J=11.1, 5.10 Hz, 2H), 3.28 (dd, J=11.1, 6.60 Hz, 2H), 2.92 (dd, J=12.6, 3.3 Hz, 2H), 2.65 (dd, J=12.6, 8.4 Hz, 2H). LCMS (5-95% gradient acetonitrile in 0.1% TFA over 10 min), single peak retention time=4.13 min on 30 mm column, (M+H)$^+$=345. UV/vis (100 μM in H$_2$O) $\lambda_{abs}$=432 nm. Fluorescence $\lambda_{ex}$=432 nm, $\lambda_{em}$=558 nm.

Example 3

(2S,2'S)-2,2'-((3,6-diaminopyrazine-2,5-dicarbonyl)bis(azanediyl))bis(3-hydroxypropanoic acid)

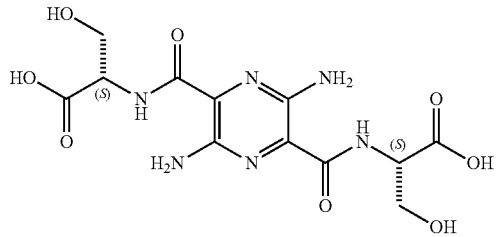

Step 1. Synthesis of dimethyl 2,2'-((3,6-diaminopyrazine-2,5-dicarbonyl)bis(azanediyl))(2S,2'S)-bis(3-(benzyloxy)propanoate)

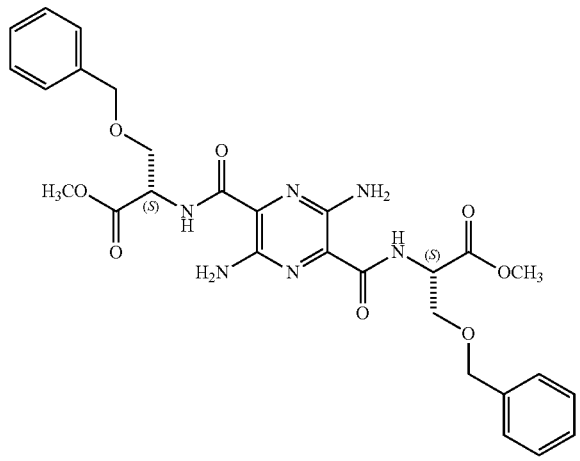

A mixture of sodium 3,6-diaminopyrazine-2,5-dicarboxylate (300 mg, 1.24 mmol), L-Ser(OBn)-OMe.HCl salt (647 mg, 2.64 mmol), HOBt.H$_2$O (570 mg, 3.72 mmol) and EDC.HCl (690 mg, 3.60 mmol) in DMF (25 mL) was treated with TEA (2 mL). The resulting mixture was stirred for 16 h and concentrated. Work up as in Example 1 afforded 370 mg (51% yield) of the bisamide as a bright yellow powder: $^1$NMR (300 MHz, CDCl$_3$): δ 8.47 (d, J=8.74 Hz, 2H), 7.25-7.37 (complex m, 10H), 5.98 (bs, 4H), 4.85 (dt, J=8.7, 3.3 Hz, 2H), 4.56 (ABq, J=12.6, Hz, Δv=11.9 Hz, 4H), 3.99 (one half of an ABq of d, J=8.7, 3.3, Δv obscured, 2H), 3.76-3.80 (one half of an ABq—obscured, 2H), 3.78 (s, 6H). $^{13}$C NMR (75 MHz, CDCl$_3$) δ 170.5 (s), 165.1 (s), 146.8 (s), 138.7 (s) 128.6 (d), 128.1 (d), 127.8 (d), 126.9 (s), 73.5 (t), 69.8 (t), 53.0 (q), 52.9 (q). LCMS (5-95% gradient acetonitrile in 0.1% TFA over 10 min), single peak retention time=4.93 min on 30 mm column, (M+H)+=581.

Step 2. Synthesis of (2S,2'S)-2,2'-((3,6-diaminopyrazine-2,5-dicarbonyl)-bis(azanediyl))bis(3-(benzyloxy)propanoic Acid

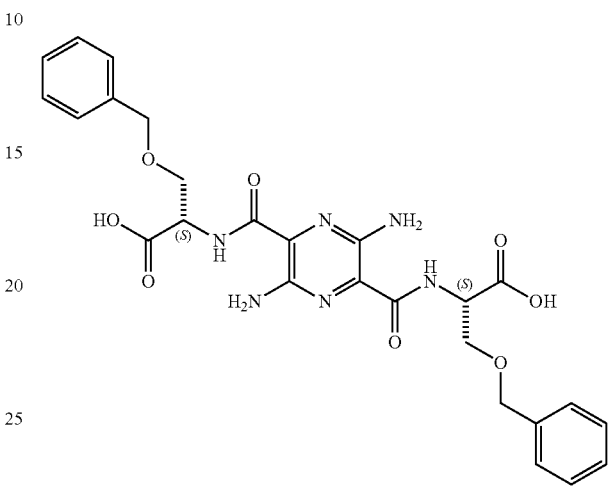

The product from step 1 (370 mg, 0.64 mmol) in THF (10 mL) was treated with 1.0 N sodium hydroxide (2.5 mL). After stirring at room temperature for 30 min, the reaction was judged complete by TLC. The pH was adjusted to approximately 2 by the addition of 1.0 N HCl and the resulting solution was extracted (3×) with EtOAc. The layers were combined, dried over sodium sulfate, filtered and concentrated to afford 353 mg (100% yield) of the diacid as an orange foam: LCMS (5-95% gradient acetonitrile in 0.1% TFA over 10 min), retention time=4.41 min on 30 mm column, (M+H)$^+$=553.

Step 3

To the product from step 2 (353 mg, 0.64 mmol) in methanol (20 mL) was added 5% Pd/C (300 mg) and ammonium formate (600 mg). The resulting reaction was heated at reflux for 2 h. The reaction was cooled to room temperature, filtered through a plug of celite and concentrated. The residue was recrystallized from methanol-ether to provide 191 mg (80% yield) of Example 3 as a yellow foam: $^1$NMR (300 MHz, DMSO-d$_6$) δ 8.48 (d, J=6.9 Hz, 2H), 6.72 (bs, 4H), 3.95 (apparent quartet, J=5.1 Hz, 2H), 3.60 (apparent ABq of doublets; down-field group centered at 3.71, J=9.9, 5.1 Hz, 2H; up-field group centered at 3.48, J=9.9, 6.3 Hz, 2H). $^{13}$C NMR (75 MHz, CDCl$_3$) δ 172.9 (s), 164.9 (s), 147.0 (s), 127.0 (s), 62.9 (d), 55.7 (t). LCMS (5-95% gradient acetonitrile in 0.1% TFA over 10 min), single peak retention time=1.45 min on 30 mm column, (M+H)$^+$=373. UV/vis (100 μM in PBS) $\lambda_{abs}$=434 nm. Fluorescence $\lambda_{ex}$=449 nm, $\lambda_{em}$=559 nm.

Example 4

3,6-bis(bis(2-methoxyethyl)amino)-$N^2,N^2,N^5,N^5$-tetrakis(2-methoxyethyl) pyrazine-2,5-dicarboxamide bis(TFA) Salt

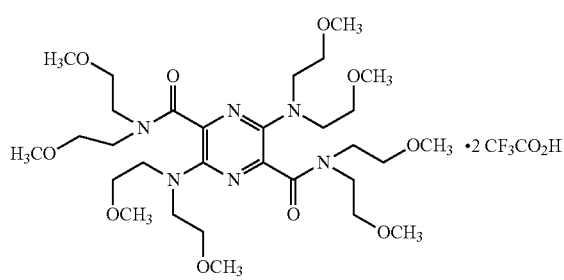 [SMILES: COCCN(CCOC)C(=O)c1nc(N(CCOC)CCOC)c(C(=O)N(CCOC)CCOC)nc1N(CCOC)CCOC]

Step 1. Synthesis of 3,6-dibromopyrazine-2,5-dicarboxylic Acid

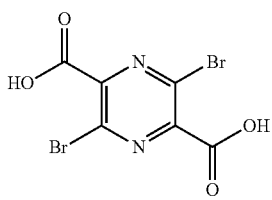 [SMILES: O=C(O)c1nc(Br)c(C(=O)O)nc1Br]

3,6-Diaminopyrazine-2,5-dicarboxylic acid (499 mg, 2.52 mmol) was dissolved in 48% hydrobromic acid (10 mL) and cooled to 0° C. in an ice-salt bath. To this stirred mixture was added a solution of sodium nitrite (695 mg, 10.1 mmol) in water (10 mL) dropwise so that the temperature remains below 5° C. The resulting mixture was stirred for 3 h at 5-15° C., during which time the red mixture became a yellow solution. The yellow solution was poured into a solution of cupric bromide (2.23 g, 10.1 mmol) in water (100 mL) and the resulting mixture was stirred at room temperature. After an additional 3 h, the aqueous mixture was extracted with EtOAc (3×). The combined extracts were dried ($Na_2SO_4$), filtered and concentrated to afford 440 mg (54% yield) 3,6-dibromopyrazine-2,5-dicarboxylic acid as a pale yellow solid: $^{13}C$ NMR (75 MHz, $CDCl_3$) δ 164.3 (s), 148.8 (s), 134.9 (s). HPLC (5-95% gradient acetonitrile in 0.1% TFA over 10 min), single peak retention time=2.95 min on 250 mm column.

Step 2. Synthesis of 3-(Bis(2-methoxyethyl)amino)-6-bromo-$N^2,N^2,N^5,N^5$-tetrakis(2-methoxyethyl) pyrazine-2,5-dicarboxamide

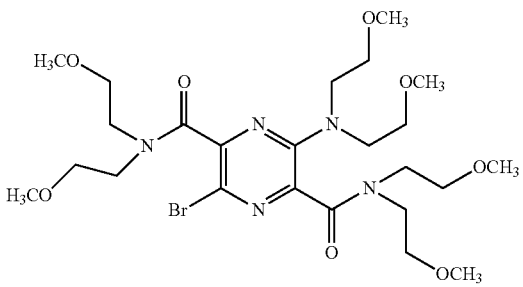 [SMILES: COCCN(CCOC)C(=O)c1nc(N(CCOC)CCOC)c(C(=O)N(CCOC)CCOC)nc1Br]

The product from step 1 (440 mg, 1.36 mmol) was dissolved in DMF (25 mL), treated with $HOBt.H_2O$ (624 mg, 4.08 mmol), and EDC.HCl (786 mg, 4.10 mmol) and stirred for 30 min at room temperature. Bis(2-methoxylethyl)amine (620 mL, 559 mg, 4.20 mmol) was added and the resulting mixture was stirred at room temperature for 16 h and concentrated. The residue was partitioned with water and EtOAc. The EtOAc layer was separated and the aqueous was extracted again with EtOAc. The combined organic layers were washed with 0.5 N HCl, saturated sodium bicarbonate, and brine. The organic layer was dried ($Na_2SO_4$), filtered and concentrated to afford 214 mg of 3-(bis(2-methoxyethyl)amino)-6-bromo-$N^2,N^2,N^5,N^5$-tetrakis(2-methoxyethyl)pyrazine-2,5-dicarboxamide (26% yield) as a brown oil: LCMS (5-95% gradient acetonitrile in 0.1% TFA over 10 min), single peak retention time=3.85 min on 30 mm column, $(M+H)^+=608$.

Step 3

To the product from step 2 (116 mg, 0.19 mmol) was added bis(2-methoxylethyl)amine (3.0 mL, 2.71 g, 20.3 mmol) and a "spatula tip" of $Pd(PPh_3)_4$. The resulting mixture was heated to 140° C. for 2 h. The reaction was cooled and concentrated. The residue was purified by flash chromatography ($SiO_2$, 10/1 $CHCl_3$-MeOH). The resulting material was purified again by reverse phase medium pressure chromatography (C18, 10-50% manual gradient acetonitrile in 0.1% TFA) to afford 12 mg (10% yield) of Example 4 as an orange-brown film: LCMS (15-95% gradient acetonitrile in 0.1% TFA over 10 min), single peak retention time=3.85 min on 250 mm column, $(M+H)^+=661$. UV/vis (100 μM in PBS) $\lambda_{abs}=434$ nm. Fluorescence $\lambda_{ex}=449$ nm, $\lambda_{em}=559$ nm.

Example 5

3,6-diamino-$N^2,N^5$-bis(2-aminoethyl)pyrazine-2,5-dicarboxamide bis(TFA) Salt

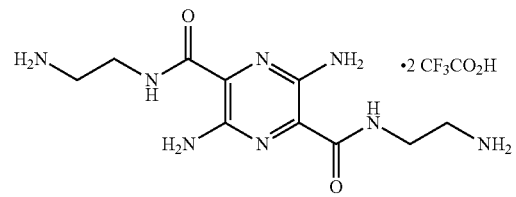 [SMILES: NCCNC(=O)c1nc(N)c(C(=O)NCCN)nc1N]

Step 1. Synthesis of 3,6-diamino-N²,N⁵-bis[2-(tert-butoxycarbonyl)-aminoethyl]pyrazine-2,5-dicarboxamide

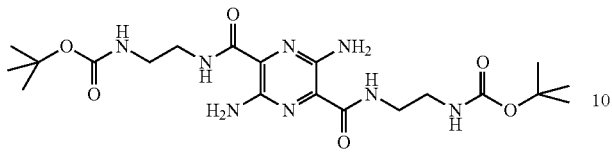

A mixture of sodium 3,6-diaminopyrazine-2,5-dicarboxylate (500 mg, 2.07 mmol), tert-butyl 2-aminoethylcarbamate (673 mg, 4.20 mmol), HOBt.H₂O (836 mg, 5.46 mmol) and EDC.HCl (1.05 g, 5.48 mmol) in DMF (25 mL) was stirred for 16 h and concentrated. Work up as in Example 1 afforded 770 mg (76% yield) of the bisamide as an orange foam: ¹NMR (300 MHz, DMSO-d₆) major conformer, δ 8.44 (t, J=5.7 Hz, 2H), 6.90 (t, J=5.7 Hz, 2H), 6.48 (bs, 4H), 2.93-3.16 (complex m, 8H), 1.37 (s, 9H), 1.36 (s, 9H). ¹³C NMR (75 MHz, DMSO-d₆), conformational isomers δ 165.1 (s), 155.5 (bs), 155.4 (bs), 146.0 (s), 126.2 (s), 77.7 (bs), 77.5 (bs), 45.2 (bt), 44.5 (bt), 28.2 (q).

Step 2

To the product from step 1 (770 mg, 1.60 mmol) in methylene chloride (100 mL) was added TFA (25 mL) and the reaction was stirred at room temperature for 2 h. The mixture was concentrated and the residue taken up into methanol (15 mL). Ether (200 mL) was added and the orange solid precipitate was isolated by filtration and dried at high vacuum to afford 627 mg (77% yield) of Example 5 as an orange powder: ¹NMR (300 MHz, DMSO-d₆) δ 8.70 (t, J=6 Hz, 2H), 7.86 (bs, 6H), 6.50 (bs, 4H), 3.46-3.58 (m, 4H), 3.26-3.40 (m, 4H). ¹³C NMR (75 MHz, DMSO-d₆) δ 166.4 (s), 146.8 (s), 127.0 (s), 39.4 (t), 37.4 (t). LCMS (5-95% gradient acetonitrile in 0.1% TFA over 10 min), single peak retention time=3.62 min on 30 mm column, (M+H)⁺=283. UV/vis (100 μM in PBS) $\lambda_{abs}$=435 nm. Fluorescence (100 nM) $\lambda_{ex}$=449 nm, $\lambda_{em}$=562 nm.

Example 6

3,6-Diamino-N²,N⁵-bis (D-aspartate)-pyrazine-2,5-dicarboxamide

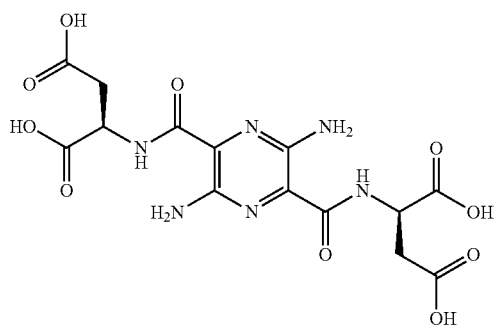 [SMILES: Nc1nc(C(=O)N[C@H](CC(=O)O)C(=O)O)c(N)nc1C(=O)N[C@H](CC(=O)O)C(=O)O]

Step 1. Synthesis of 3,6-Diamino-N²,N⁵-bis (benzyl D-O-benzyl-aspartate)-pyrazine-2,5-dicarboxamide

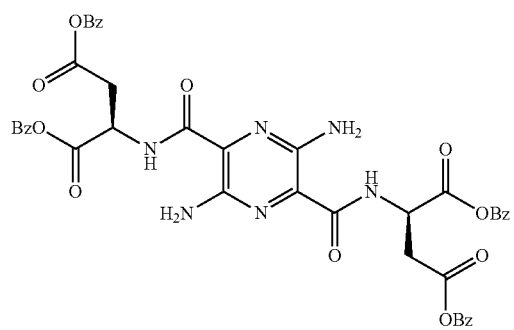

A mixture of sodium 3,6-diaminopyrazine-2,5-dicarboxylate (600 mg, 2.48 mmol), Asp(OBn)-OMe-p-TosH salt (2.43 g, 5.00 mmol), HOBt.H₂O (919 mg, 6.00 mmol) and EDC.HCl (1.14 g, 5.95 mmol) in DMF (50 mL) was treated with TEA (4 mL). The resulting mixture was stirred over night at room temperature. The reaction mixture was concentrated and the residue was partitioned with water and EtOAc. The EtOAc layer was separated and washed successively with saturated sodium bicarbonate, water and brine. The EtOAc solution was dried (Na₂SO₄), filtered and concentrated. The residue was purified by flash chromatography (SiO₂, 50/1 CHCl₃-MeOH to 10/1) to afford 1.15 g of the bis-amide (58% yield) as a yellow foam: ¹NMR (500 MHz, CDCl₃) δ 8.61 (d, J=8.4 Hz, 2H), 7.29-7.39 (m, 20H), 5.85 (bs, 4H), 5.22 (ABq, J=10.0 Hz, Δν=17.3 Hz, 4H), 5.10 (ABq, J=12.2 Hz, Δν=34.3 Hz, 4H), 5.06-5.09 (obs m, 2H), 3.11 (ABq of d, J=17.0, 5.14 Hz, Δν=77.9 Hz, 4H). ¹³C NMR (75 MHz, CDCl₃) δ 170.7 (s), 170.7 (s), 165.4 (s), 147.0 (s), 135.7 (s), 135.6 (s), 129.0 (d), 128.9 (d), 128.8 (d), 128.75 (d), 128.7 (d), 126.9 (s), 68.0 (t), 67.3 (t), 49.1 (d), 37.0 (t). LCMS (50-95% gradient acetonitrile in 0.1% TFA over 10 min), single peak retention time=5.97 min on 250 mm column, (M+H)⁺=789.

Step 2

To the product from step 1 (510 mg, 0.65 mmol) was added THF (20 mL) and water (10 mL). The stirred mixture was added 10% Pd(C) (500 mg) and ammonium formate (1 g). The resulting mixture was heated to 60° C. for 2 h and allowed to cool to room temperature. The mixture was filtered through celite and concentrated. The resulting material was purified again by reverse phase medium pressure chromatography (C18, 10-70% manual gradient acetonitrile in 0.1% TFA) to afford 137.8 mg (54% yield) of Example 6 as an orange solid: ¹NMR (300 MHz, DMSO-d₆) δ 8.62 (d, J=8.4 Hz, 2H), 6.67 (bs, 4H), 4.725 (dt, J=8.4, 5.4 Hz, 2H), 2.74-2.88 (complex m, 4H). ¹³C NMR (75 MHz, DMSO-d₆) δ 172.6 (s), 165.2 (s), 147.0 (s), 126.6 (s), 60.8 (t), 49.1 (d). LCMS (5-95% gradient acetonitrile in 0.1% TFA over 10 min), single peak retention time=4.01 min on 250 mm column, (M+H)⁺=429. UV/vis (100 μM in PBS) $\lambda_{abs}$=433 nm. Fluorescence (100 nM) $\lambda_{ex}$=449 nm, $\lambda_{em}$=558 nm.

Example 7

3,6-Diamino-N²,N⁵-bis(14-oxo-2,5,8,11-tetraoxa-15-azaheptadecan-17-yl)pyrazine-2,5-dicarboxamide

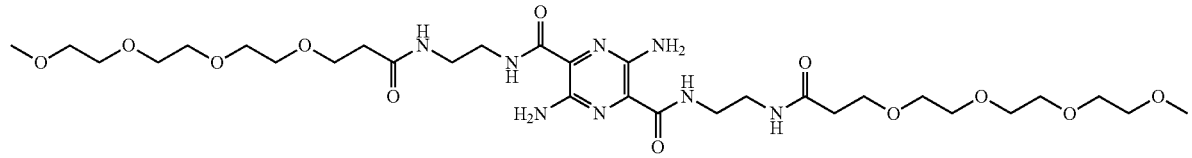

To a solution of Example 5 (77.4 mg, 0.15 mmol) in DMF (5 mL) was added TEA (151 mg, 1.49 mmol) and 2,5-dioxopyrrolidin-1-yl 2,5,8,11-tetraoxatetradecan-14-oate (113 mg, 0.34 mmol) and the reaction was stirred for 16 h at room temperature. The reaction was concentrated and the residue was purified by medium pressure revered phase chromatography (LiChroprep RP-18 Lobar (B) 25×310 mm—EMD chemicals 40-63 µm, ~70 g, 90/10 to 80/20 0.1% TFA-ACN) to afford 37.4 mg (35% yield) of example 7 as an orange film: ¹NMR (300 MHz, DMSO-d$_6$) δ 8.47 (t, J=5.7 Hz, 2H), 7.96 (t, J=5.4 Hz, 2H), 3.20-3.60 (complex m, 36H), 3.47 (s, 3 H), 3.46 (s, 3H), 2.30 (t, J=6.3 Hz, 4H). ¹³C NMR (75 MHz, DMSO-d$_6$) δ 170.2 (s), 165.1 (s), 146.0 (s), 126.2 (s), 71.2 (t), 69.7 (t), 69.6 (t), 69.5 (t), 69.4 (t), 66.7 (t), 58.0 (q), 38.2 (t), 36.2 (t). LCMS (5-95% gradient acetonitrile in 0.1% TFA over 10 min), single peak retention time=4.01 min on 250 mm column, (M+H)⁺=719, (M+Na)⁺=741. UV/vis (100 µM in PBS) λ$_{abs}$=437 nm. Fluorescence (100 nM) λ$_{ex}$=437 nm, λ$_{em}$=559 nm.

Example 8

3,6-Diamino-N²,N⁵-bis(26-oxo-2,5,8,11,14,17,20,23-octaoxa-27-azanonacosan-29-yl)pyrazine-2,5-dicarboxamide

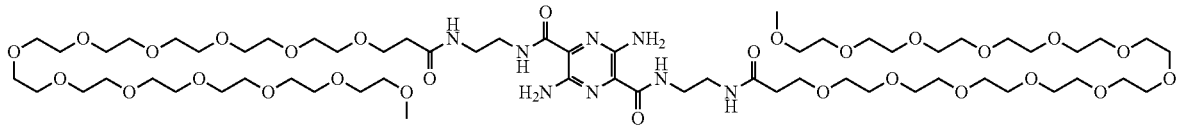

To a solution of Example 5 (50.3 mg, 0.10 mmol) in DMF (5 mL) was added TEA (109 mg, 1.08 mmol) and 2,5-dioxopyrrolidin-1-yl 2,5,8,11,14,17,20,23-octaoxahexacosan-26-oate (128 mg, 0.25 mmol) and the reaction was stirred for 16 h at room temperature. The reaction was concentrated and the residue was purified by medium pressure revered phase chromatography (LiChroprep RP-18 Lobar (B) 25×310 mm—EMD chemicals 40-63 µm, ~70 g, 90/10 to 80/20 0.1% TFA-ACN) to afford 87.9 mg (82% yield) of example 8 as an orange film: ¹NMR (300 MHz, DMSO-d$_6$) δ 8.46 (t, J=5.7 Hz, 2H), 7.96 (t, J=5.4 Hz, 2H), 3.16-3.73 (complex m, 74H), 2.28-2.32 (m, 2H). ¹³C NMR (75 MHz, DMSO-d$_6$)—multiple conformations—δ 170.1 (s), 169.9 (s) 169.8 (s), 165.1 (s), 146.0 (s), 126.2 (s). 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, (M+H)⁺=1071, (M+2H)²⁺=536. UV/vis (100 µM in PBS) λ$_{abs}$=438 nm. Fluorescence (100 nM) λ$_{ex}$=438 nm, λ$_{em}$=560 nm.

Example 9

3,6-Diamino-N²,N⁵-bis(38-oxo-2,5,8,11,14,17,20,23,26,29,32,35-dodecaoxa-39-azahentetracontan-41-yl)pyrazine-2,5-dicarboxamide

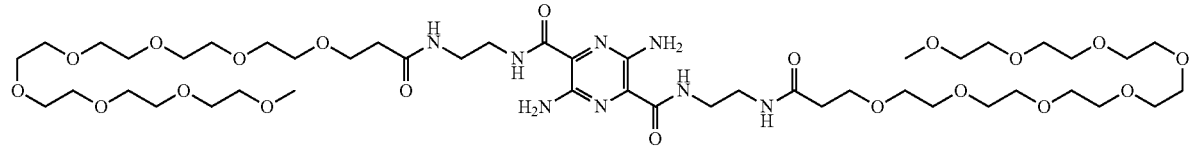 [SMILES: COCCOCCOCCOCCOCCOCCOCCOCCC(=O)NCCNC(=O)c1nc(N)c(C(=O)NCCNC(=O)CCOCCOCCOCCOCCOCCOCCOCCOC)nc1N]

To a solution of Example 5 (53.1 mg, 0.10 mmol) in DMF (5 mL) was added TEA (114 mg, 1.13 mmol) and 2,5-dioxopyrrolidin-1-yl 2,5,8,11,14,17,20,23,26, 29,32,35-dodecaoxaoctatriacontan-38-oate (144 mg, 0.21 mmol) in DMF (2.0 mL) and the resulting mixture was stirred for 16 h thereafter. The reaction was concentrated and the residue was purified by medium pressure revered phase chromatography (LiChroprep RP-18 Lobar (B) 25×310 mm—EMD chemicals 40-63 µm, ~70 g, 90/10 to 80/20 0.1% TFA-ACN) to afford 87.5 mg (61% yield) of example 9 as an orange film: ¹NMR (300 MHz, DMSO-d$_6$) δ 8.48 (t, J=5.7 Hz, 2H), 7.96 (t, J=5.4 Hz, 2H), 7.80-7.86 (m, 2H), 5.94 (bm, 2H), 3.30-3.60 (complex m, 106H), 2.26-2.33 (m, 4H). ¹³C NMR (75 MHz, DMSO-d$_6$) δ 170.2 (s), 165.1 (s), 146.0 (s), 126.2 (s), 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, $(M+2H)^{2+}=712$. UV/vis (100 μM in PBS) $\lambda_{abs}=449$ nm. Fluorescence (100 nM) $\lambda_{ex}=449$ nm, $\lambda_{em}=559$ nm.

Example 10

Bis(2-(PEG-5000)ethyl) 6-(2-(3,6-diamino-5-(2-aminoethylcarbamoyl) pyrazine-2-carboxamido)ethylamino)-6-oxohexane-1,5-diyldicarbamate

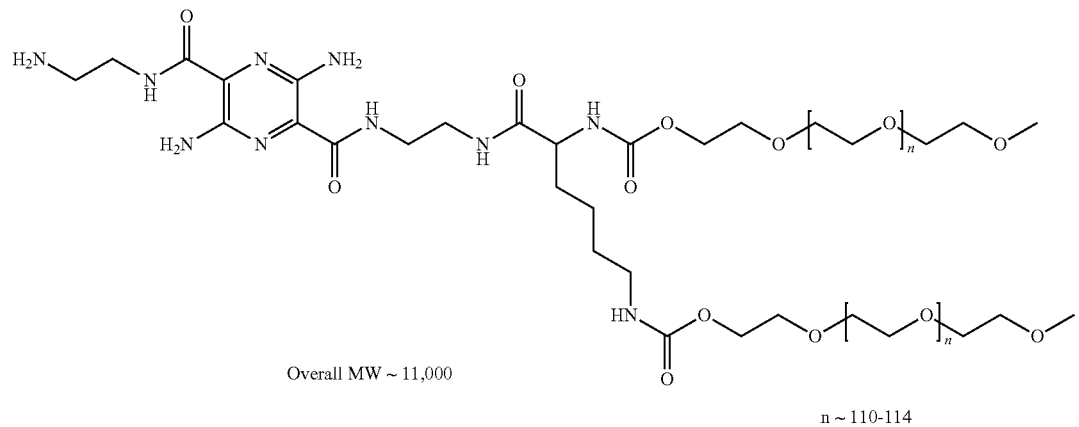

Overall MW ~ 11,000 n ~ 110-114

A solution of Example 5 (25 mg, 0.049 mmol) in DMF (30 mL) was treated with TEA (1 mL) and m-PEG2-NHS (1 g, 0.1 mmol) and the resulting mixture was stirred for 48 h at room temperature. The mixture was concentrated and the residue was partially purified by gel filtration chromatography (G-25 resin, water). The product was concentrated and further purified by reverse phase medium pressure chromatography (C18, 10-70% manual gradient acetonitrile in 0.1% TFA) to afford 137.8 mg (54% yield) of Example 10 as a tan waxy solid: Maldi MS m/z=11393.

Example 11

(R)-2-(6-(bis(2-methoxyethyl)amino)-5-cyano-3-morpholinopyrazine-2-carboxamido)succinic Acid

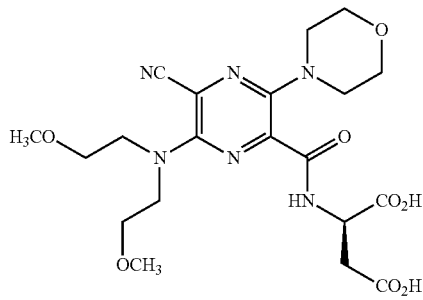 [SMILES: COCCN(CCOC)c1nc(C(=O)N[C@H](CC(=O)O)C(=O)O)c(N2CCOCC2)nc1C#N]

Step 1. Synthesis of 2-amino-5-bromo-3,6-dichloropyrazine

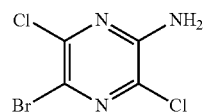

A solution of 2-amino-6-chloropyrazine (25 g, 193.1 mmol) in MeOH (500 mL) was treated with NBS (34.3 g, 193.1 mmol), portion-wise, over 1 hour. The resulting mixture was stirred for 16 hours thereafter. TLC analysis at this time shows a small amount of starting material remaining. Another 1.4 g NBS added and reaction heated to 50° C. for 2 hours. The mixture was then cooled to 38° C. and treated with NCS (25.8 g, 193.1 mmol). The reaction mixture was heated to 50° C. for 16 hours thereafter. The mixture was then cooled to room temperature and treated with water (500 mL). The precipitate was collected by filtration and dried in a vacuum desiccator to afford 45.4 g (97% yield) of 2-amino-5-bromo-3,6-dichloropyrazine as a white solid: $^{13}$C NMR (75 MHz, CDCl$_3$) δ 149.9 (s), 145.6 (s), 129.6 (s), 121.5 (s). LCMS (15-95% gradient acetonitrile in 0.1% TFA over 10 min), single peak retention time=4.51 min on 30 mm column, $(M+H)^+=244$, $(M+H+ACN)^+=285$.

Step 2. Synthesis of 5-amino-3,6-dichloropyrazine-2-carbonitrile

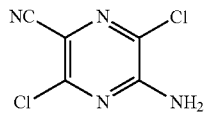

A mixture of CuCN (8.62 g, 96.3 mmol) and NaCN (4.72 g, 96.3 mmol) was heated under high vacuum to 90° C. The resulting mixture was subjected to three Argon/Vacuum cycles and placed under a final positive pressure of Argon. The mixture was allowed to cool to room temperature and DMF (150 mL) was added. The heterogeneous mixture was heated to 130° C. for 2.5 hours. To the resulting homogeneous mixture of sodium dicyanocuprate was added a solution of the product from step 1 (15.6 g, 64.2 mmol) dissolved in DMF (150 mL), dropwise, over 1 hour. The temperature was gradually raised to 150° C. and the resulting mixture was stirred at this temperature for 10 hours thereafter. The reaction was then allowed to cool to room temperature and poured into water (1 L). The resulting mixture was extracted with EtOAc (3×) and the combined extracts were filtered to remove a flocculent dark solid, washed with brine, dried ($Na_2SO_4$), filtered again and concentrated. Purification by flash column chromatography ($SiO_2$, 10/1 hexanes-EtOAc to 3/1) to afford 6.70 g (55% yield) of the nitrile product as a tan solid: $^{13}C$ NMR (75 MHz, $CDCl_3$) δ 153.9 (s), 149.1 (s), 131.7 (s), 115.4 (s), 111.0 (s). GCMS (Inj. temperature=280° C., 1.0 mL/min helium flow rate, temperature program: 100° C. (2 min hold), ramp to 300° C. @ 10° C./min (2 min hold), major peak retention time=16.556 min, m/z (EI)=188, 190.

Step 3. Synthesis of 5-amino-3-(bis(2-methoxyethyl)amino)-6-chloropyra-zine-2-carbonitrile

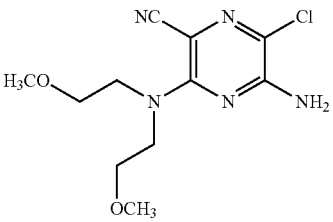 [SMILES: COCCN(CCOC)c1nc(N)c(Cl)nc1C#N]

To the product from step 2 (1.00 g, 5.29 mmol) in ACN (20 mL) was added bis(2-methoxyethyl)amine (3.0 mL, 2.71 g, 20.3 mmol) and the reaction mixture was heated to 70° C. for 16 hours thereafter. The reaction was cooled and concentrated. The residue was partitioned with EtOAc and water. The organic layer was separated and the aqueous was extracted again with EtOAc. The combined organic extracts were washed with brine, dried ($Na_2SO_4$), filtered and concentrated. Purification by flash column chromatography ($SiO_2$, 10/1 hexanes-EtOAc to 1/1) afforded 950 mg (63% yield) of the desired adduct as a yellow solid: $^1$NMR (300 MHz, $CDCl_3$) δ 7.47 (bs, 2H), 3.77 (t, J=5.7 Hz, 4H), 3.52 (t, J=5.4 Hz, 4H), 3.25 (s, 6H). $^{13}C$ NMR (75 MHz, $CDCl_3$) δ 154.7 (s), 152.0 (s), 120.9 (s), 119.5 (s), 95.8 (s), 71.0 (t), 59.1 (q), 50.0 (t). LCMS (50-95% gradient acetonitrile in 0.1% TFA over 10 min), single peak retention time=4.91 min on 250 mm column, $(M+H)^+=286$, $(M+Na)^+=308$, $(M+Na+ACN)^+=349$.

Step 4. Synthesis of 3-(bis(2-methoxyethyl)amino)-5-bromo-6-chloropyrazine-2-carbonitrile

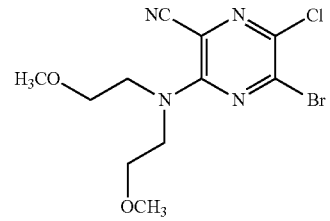 [SMILES: COCCN(CCOC)c1nc(Br)c(Cl)nc1C#N]

To the product from step 3 (1.39 g, 4.88 mmol) in 48% hydrobromic acid (20 mL) at 0° C. (ice-salt bath), was added a solution of sodium nitrite (673 mg, 9.75 mmol) in water (10 mL) dropwise over 30 min. The resulting mixture was stirred at 0-5° C. for 1 h and poured into a stirred solution of $CuBr_2$ (1.64 g, 7.34 mmol) in water (100 mL). The resulting mixture was stirred for 16 h at room temperature thereafter. The mixture was extracted with EtOAc (3×). The combined organic layers were dried ($Na_2SO_4$), filtered and concentrated. Purification by flash column chromatography ($SiO_2$, 50/1 CHCl3-MeOH) afforded 1.00 g (58% yield) of the bromide as an orange-brown solid: $^1$NMR (300 MHz, $CDCl_3$) δ 3.99 (t, J=5.4 Hz, 4H), 3.64 (t, J=5.4 Hz, 4H), 3.35 (s, 6H). $^{13}C$ NMR (75 MHz, $CDCl_3$) δ 152.8 (s), 140.8 (s), 133.4 (s), 117.2 (s), 108.3 (s), 70.4 (t), 59.1 (t), 50.5 (q). LCMS (50-95% gradient acetonitrile in 0.1% TFA over 10 min), single peak retention time=4.55 min on 250 mm column, $(M+H)^+=349, 351$.

Step 5. Synthesis of 3-(bis(2-methoxyethyl)amino)-6-chloro-5-(furan-2-yl)pyrazine-2-carbonitrile

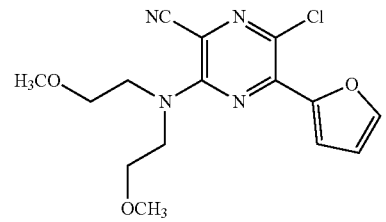 [SMILES: COCCN(CCOC)c1nc(-c2ccco2)c(Cl)nc1C#N]

A mixture of the product from step 4 (1.0 g, 2.87 mmol), 2-furanboronic acid (643 mg, 5.75 mmol), $Cs_2CO_3$ (3.31 g, 10.2 mmol), TFP (35 mol %, 236 mg, 1.02 mmol), and $Pd_2dba_3$-$CHCl_3$ (5 mol %, 10 mol % Pd, 150 mg) was subjected to 3 vacuum/Argon cycles and placed under a positive pressure of Argon. Anhydrous dioxane (50 mL) was added and the reaction mixture was heated to 75° C. for 16 h thereafter. The reaction mixture was cooled to room temperature, diluted with EtOAc (100 mL) and filtered through a medium frit. Concentration and purification of the residue by flash chromatography ($SiO_2$, 50/1 $CHCl_3$-MeOH) afforded the 757 mg of the furan adduct (78% yield) as a tan powder: LCMS (5-95% gradient acetonitrile in 0.1% TFA over 10 min), single peak retention time=6.41 min on 250 mm column, $(M+H)^+=337$.

Step 6. Synthesis of 6-(bis(2-methoxyethyl)amino)-3-chloro-5-cyanopyrazine-2-carboxylic Acid

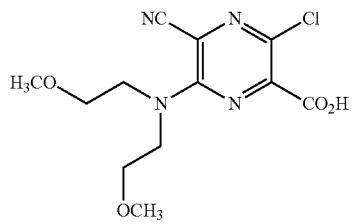 [SMILES: COCCN(CCOC)c1nc(C(=O)O)c(Cl)nc1C#N]

To a well stirred mixture of ACN (11 mL), CCl4 (7 mL), and water (11 mL) were added sodium periodate (1.07 g, 5.00 mmol) and RuO$_2$.H$_2$O (13.3 mg, 0.10 mmol), sequentially. The resulting mixture was stirred vigorously at room temperature for 30 min and treated with sodium bicarbonate (2.10 g, 25.0 mmol) followed by water (5 mL). Vigorous stirring for another 15 minutes was followed by the addition of a solution of the product from Step 5 (276 mg, 0.82 mmol) dissolved in ACN (1 mL). The green mixture was stirred at room temperature for 5.5 h. The mixture was transferred to a separatory funnel and extracted with EtOAc. The aqueous layer was adjusted to pH-3.5 and extracted again with EtOAc (2×). The combined extracts were washed with 20% sodium bisulfite and brine and dried (Na$_2$SO$_4$). Filtration and concentration afforded 140 mg (54% yield) of carboxylic acid as a pale yellow solid: LCMS (5-95% gradient acetonitrile in 0.1% TFA over 10 min), single peak retention time=5.05 min on 250 mm column, (M+H)$^+$=315.

Step 7. Synthesis of (R)-dibenzyl 2-(6-(bis(2-methoxyethyl)amino)-3-chloro-5-cyanopyrazine-2-carboxamido)succinate

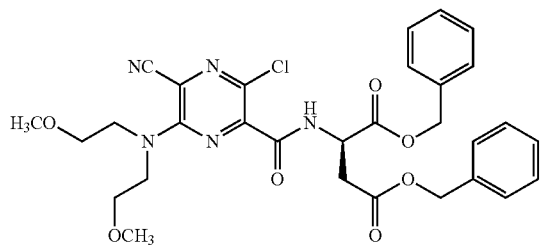 [SMILES: COCCN(CCOC)c1nc(C(=O)N[C@H](CC(=O)OCc2ccccc2)C(=O)OCc2ccccc2)c(Cl)nc1C#N]

A mixture of the product from step 6 (140 mg, 0.45 mmol), EDC.HCl (128 mg, 0.67 mmol) and HOBt.H$_2$O (102 mg, 0.67 mmol) in anhydrous DMF (25 mL) was stirred together at room temperature for 30 min. To this stirred mixture was added (R)-dibenzyl 2-aminosuccinate p-TsOH salt (213 mg, 0.44 mmol) followed by TEA (1 mL). The resulting mixture was stirred for 16 h thereafter. The reaction mixture was concentrated and partitioned with EtOAc and saturated sodium bicarbonate solution. The EtOAc layer was separated and washed with saturated sodium bicarbonate and brine, dried (Na$_2$SO$_4$), filtered and concentrated to afford 240 mg (88% yield) of the pyrazine amide as an orange foam: LCMS (15-95% gradient acetonitrile in 0.1% TFA over 10 min), single peak retention time=8.76 min on 250 mm column, (M+H)$^+$=610, (M+Na)$^+$=632.

Step 8. (R)-dibenzyl 2-(6-(bis(2-methoxyethyl)amino)-5-cyano-3-morpholinopyrazine-2-carboxamido)succinate

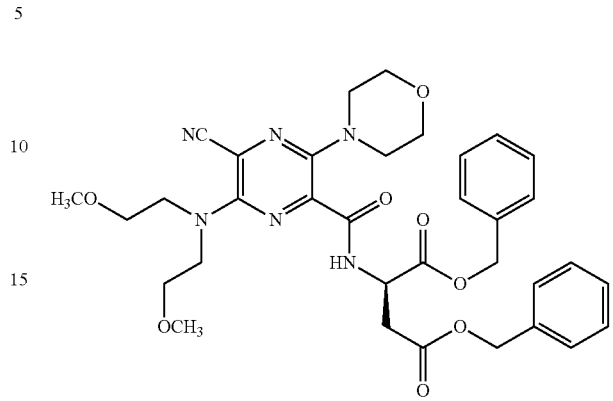

To the product from step 7 (240 mg, 0.39 mmol) was added morpholine (5 mL). The reaction mixture was heated to 70° C. for 2 h. The mixture was cooled and concentrated. The residue was partitioned with EtOAc and water. The EtOAc layer was separated and washed with saturated sodium bicarbonate and brine. The EtOAc layer was dried (Na$_2$SO$_4$), filtered and concentrated. Purification by flash column chromatography (SiO$_2$, 3:1 to 1:1 hexanes-EtOAc) afforded 199 mg (75% yield) of the morpholine adduct as an orange foam: LCMS (15-95% gradient acetonitrile in 0.1% TFA over 10 min), single peak retention time=8.76 min on 250 mm column, (M+H)$^+$=661, (M+Na)$^+$=683.

Step 9. Synthesis of Example 11

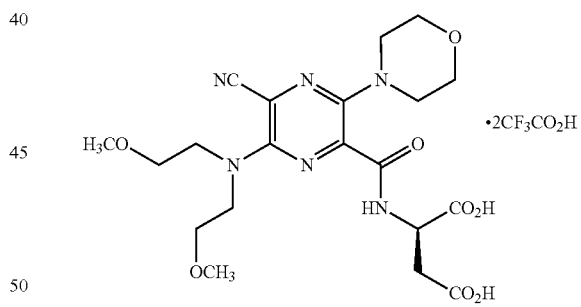

The dibenzyl ester (115 mg, 0.17 mmol) in THF (10 mL) was added 1.0 N sodium hydroxide (4 mL). The mixture was stirred for 1 h at room temperature. The pH was adjusted to ~2 with 1.0 N HCl and the solution was concentrated. Purification of the residue by medium pressure reversed phase chromatography (LiChroprep RP-18 Lobar (B) 25×310 mm—EMD chemicals 40-63 μm, ~70 g, 90/10 to 50/50 0.1% TFA-ACN) afforded 32 mg (27% yield) of example 11 as an orange solid: LCMS (15-95% gradient acetonitrile in 0.1% TFA over 10 min), single peak retention time=4.47 min on 250 mm column, (M+H)$^+$=481. UV/vis (100 μM in PBS) $\lambda_{abs}$=438 nm. Fluorescence (100 nM) $\lambda_{ex}$=449 nm, $\lambda_{em}$=570 nm.

Example 12

(2R,2'R)-2,2'-(3,6-diaminopyrazine-2,5-dicarbonyl) bis(azanediyl))bis(3-hydroxypropanoic acid) ("D-Serine Isomer" or "MB-102")

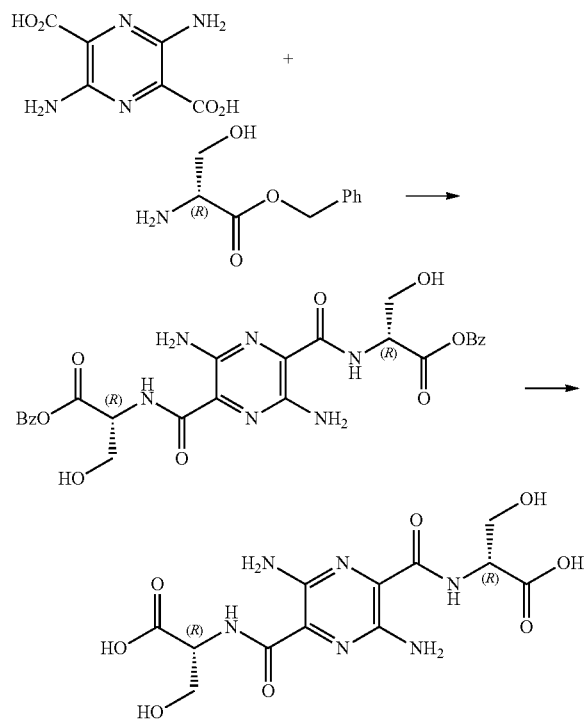

Step 1: Formation of dibenzyl 2,2'-((3,6-diaminopyrazine-2,5-dicarbonyl) bis(azanediyl))(2R,2'R)-bis (3-hydroxypropanoate A 500 mL round-bottom flask equipped with a Claisen adapter and an addition funnel was charged with D-serine benzyl ester hydrochloride (24.33 g, 105.0 mmol), and anhydrous DMF (300 mL) was added by cannula. The solution was cooled in an ice-bath and stirred for 15 min under $N_2$ atmosphere. DIPEA (19.16 mL, 110.0 mmol) was added dropwise via addition funnel over a 30 min period, and after a further 30 min, the cooling bath was removed and the diacid (9.91 g, 50.0 mmol) was added in one portion. The brick-red suspension was stirred for 30 min and HOBt.$H_2O$ (17.61 g, 115.0 mmol) was added in one portion. After 15 min, the reaction flask was cooled in an ice-bath, and EDC.HCl (22.05 g, 115.0 mmol) was added in portions over 15 minutes. The resulting suspension was slowly allowed to warm to room temperature and stirred overnight (ca. 17 h) under $N_2$.

The dark solution was concentrated to a syrupy residue under high vacuum (bath temp 60° C.) that was partitioned between EtOAc and milli-Q $H_2O$ (400 mL each). The layers were separated, and the aqueous layer was extracted with EtOAc (3×200 mL). The combined EtOAc extracts were successively washed with 0.50 M $KHSO_4$, saturated $NaHCO_3$, $H_2O$, and brine (250 mL each). Removal of the solvent under reduced pressure gave 23.7 g of an orange solid. The crude product was purified by flash chromatography over silica gel using a $CHCl_3$:MeOH gradient to give the bisamide (19.6 g, 71%) as an orange solid: $R_f$ 0.45 [$CHCl_3$:MeOH (9:1, v/v)]. $^1$H NMR (DMSO-$d_6$) δ 8.56 (d, J=8.0 Hz, 2H, exchangeable with $D_2O$), 7.40-7.33 (m, 10H), 6.76 (s, 4H, exchangeable with $D_2O$), 5.37 (t, J=5.5 Hz, 2H), 5.20 (m, 4H), 4.66-4.63 (dt, J=8.0, 4.0 Hz, 2H), 3.97-3.93 (m, 2H), 3.81-3.77 (m, 2H). $^{13}$C NMR (DMSO-$d_6$) δ 170.1, 164.9, 146.4, 135.8, 128.4, 128.0, 127.6, 125.9, 66.2, 61.1, 54.4. RP-LC/MS (ESI) m/z 553.3 (M+H)+ (tR=4.44 min, 5-95% B/6 min). Anal. Calcd for $C_{26}H_{28}N_6O_8$: C, 56.52; H, 5.11; N, 15.21. Found: C, 56.39; H, 5.11; N, 14.99.

Step 2. Formation of (2R,2'R)-2,2'-((3,6-diaminopyrazine-2,5-dicarbonyl)bis(azanediyl))bis(3-hydroxypropanoic acid)

The bisamide (7.74 g, 14.0 mmol) was hydrogenated in the presence of 10% Pd/C (0.774 g) in EtOH:$H_2O$ (560 mL; 3:1, v/v). The reaction mixture was purged with argon and stirred under hydrogen atmosphere (slow bubbling) at room temperature for 5.5 h. The reaction mixture was again purged with Ar, and the catalyst was removed by filtration over Celite. The bed was washed with EtOH:H2O (400 mL; 1:1, v/v), and the combined filtrates were concentrated in vacuo. The product was dried under high vacuum. The residue was triturated with $CH_3CN$ to give the D-serine isomer (4.89 g, 94%) as an orange powder. $^1$H NMR (DMSO-$d_6$) δ 8.46 (d, J=8.3 Hz, 2H, exchangeable with $D_2O$), 6.78 (br s, 4H, exchangeable with $D_2O$), 4.48-4.45 (dt, J=8.1, 3.9 Hz, 2H), 3.88 (dd, J=11.1, 3.9 Hz, 2H), 3.74 (dd, J=11.1, 3.7 Hz, 2H). $^{13}$C NMR (DMSO-$d_6$) δ 171.6, 164.7, 146.4, 125.9, 61.2, 54.3. RP-LC/MS (ESI) m/z 373.2 (M+H)+(tR=2.86 min, 5_95% B/6 min). Anal. Calcd for $C_{12}H_{16}N_6O_8$: C, 38.71; H, 4.33; N, 22.57. Found: C, 38.44; H, 4.51: N, 22.33.

Example 13

(2R,2'R)-2,2'-(3,6-diaminopyrazine-2,5-dicarbonyl) bis(azanediyl)) dipropionic Acid ("D-Alanine Isomer")

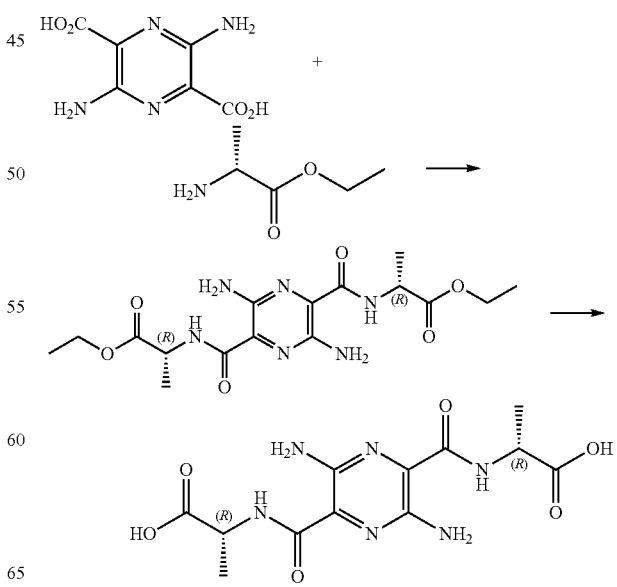

Step 1. Formation of diethyl 2,2'-((3,6-diaminopy-razine-2,5-dicarbonyl) bis(azanediyl))(2R,2'R)-dipropionate Under an inert atmosphere, a flame dried round-bottom flask (100 mL) equipped with a magnetic stir bar was charged with 3,6-diaminopyrazine-2,5-dicarboxylic acid (1.0 g), D-alanine ethyl ester hydrochloride (1.86 g), EDC.HCl (2.70 g), HOBt.H$_2$O (2.65 g), and Et$_3$N (2.0 mL) in DMF (anhydrous, 80 mL). Volatiles were removed under reduced pressure at 50° C. to generate a dark semi-solid. After cooling, acetonitrile (~100 mL) was added and solution allowed to stand for about an hour. A red precipitate was isolated by centrifugation, washed with EtOAc and dried. Total weight 1.30 gm of diester (3.06 mmol, 60.6% isolated yield). This material (1.3 g) was taken forward without further purification.

Step 2. Formation of (2R,2'R)-2,2'-((3,6-diaminopy-razine-2,5-dicarbonyl) bis(azanediyl)) dipropionic Acid The diester from Step 1 (1.0 g) and LiOH (4 equivs.) in THF/water were combined and stirred at ambient temperature for several hours. HPLC indicated complete hydrolysis. The pH was made acidic by addition of TFA, and the reaction mixture allowed to stand overnight at ambient temperature. The diacid was obtained by purification of the reaction mixture by prep RPHPLC. Program: 99:1 A:B for 5 minutes then 5:95 A:B at 27 minutes @ 50 mL/min. Lambda UV 264 nm and fluorescence; $\lambda_x$=440 nm, $\lambda_m$=565 nm. Fractions containing desired product were combined and lyophilized (−85 C, 15 mtorr) to obtain an orange solid (0.821 g, 2.41 mmol, 95.6% isolated yield). M/z 341.13. Proton and carbon NMR were consistent with the proposed structure.

Example 14

3,3'-(3,6-diaminopyrazine-2,5-dicarbonyl)bis (azanediyl))Dipropionic acid ("β-Alanine Isomer")

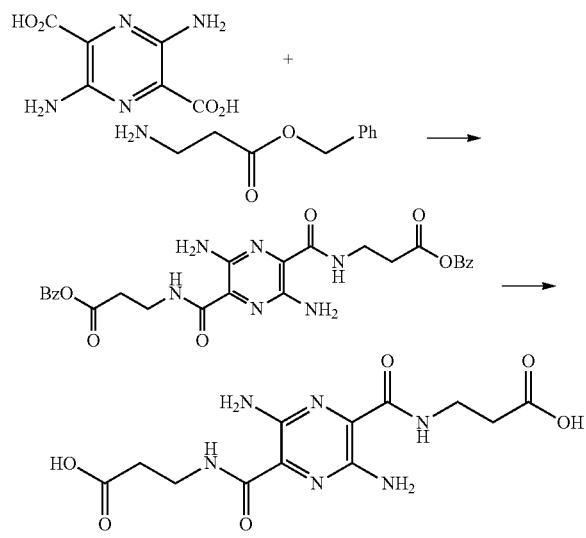

Step 1. Formation of dibenzyl 3,3'-((3,6-diaminopy-razine-2,5-dicarbonyl) bis(azanediyl))dipropionate Under an inert atmosphere, a flame dried round-bottom flask (100 mL) was charged with 3,6-diaminopyrazine-2,5-dicarboxylic acid (0.30 g), benzyl 3-aminopropanoate p-toluene sulfonate (1.08 g), EDC.HCl (0.590 g), HOBt.H$_2$O (0.582 g), and Et$_3$N (1.50 g) in DMF (anhydrous, 40). The reaction mixture was stirred overnight at ambient temperature and concentrated in vacuo to about 10 mL. The remaining DMF was removed by toluene azeotrope. The reaction mixture was partitioned between EtOAc (3×125 mL) and saturated NaHCO$_3$ (3×100 mL). The organic layers were combined and washed with citric acid (10% aqueous, 100 mL) and brine (100 mL). The organic layer was removed, dried (Na$_2$SO$_4$ anhydrous) and concentrated in vacuo to give a crystalline solid, 0.58 g. TLC (silica on glass, 1:1 EtOAc:hexanes) R$_f$=0.22. The product was purified via flash chromatography over silica gel to give 0.49 g of product. Mass spectrum (ES+) 521.36 (100%), 522.42 (30%), 523.34 (approx. 6%). NMR, $^1$H (DMSO-d$_6$), 400 MHz: 2.55 (4H, m), 3.41 (4H, m) 5.01 (4H, s), 6.44 (4H, s), 7.21 (10H, m), 8.41 (2H, m); $^{13}$C (DMSO-d$_6$): 34.18, 35.33, 66.19, 126.74, 128.52, 128.92, 136.56, 146.75, 165.63, 171.90.

Step 2. Formation of 3,3'-((3,6-diaminopyrazine-2,5-dicarbonyl)bis (azanediyl))dipropionic Acid The dibenzyl ester in Step 1 (0.92 g) was combined with EtOH (abs., 75 mL) and transferred to a Fischer-Porter pressure bottle (6 oz) equipped with inlet and outlet valves, a pressure gauge (0-100 psig) and a Teflon coated magnetic stir bar. Water (25 mL) and 10% Pd on carbon (0.2 g, Degussa/Aldrich wet) were added, and the reaction vessel sealed. Following three vacuum/Ar cycles, H$_2$(g) was introduced from a lecture bottle at 10 psig to a vigorously stirred solution. After 3.5 hours, the reaction was filtered through a pad of celite and the resulting celite/catalyst bed rinsed with about 500 mL 1:1 EtOH:H$_2$O to obtain a solution that was concentrated in vacuo. 0.424 g of a solid was isolated (70.5% isolated yield). HPLC/MS gave only a single peak at 9.3 minutes. Mass spectrum (ES+) 341.32 (100%), 342.37 (30%), 344.29 (18%), 270.30 (62%). NMR, $^1$H (DMSO-d$_6$), 400 MHz: 2.54 (2H, m), 3.42 (2H, m), 6.52 (2H, s), 7.21 (4H, m), 8.38 (2H, m), 11.9 (2H, bs); $^{13}$C (DMSO-d$_6$): 34.20, 35.33, 126.77, 146.75, 165.55, 173.57.

Example 15

2,2'-(3,6-diaminopyrazine-2,5-dicarbonyl)bis (azanediyl))diacetic Acid ("Glycine Isomer")

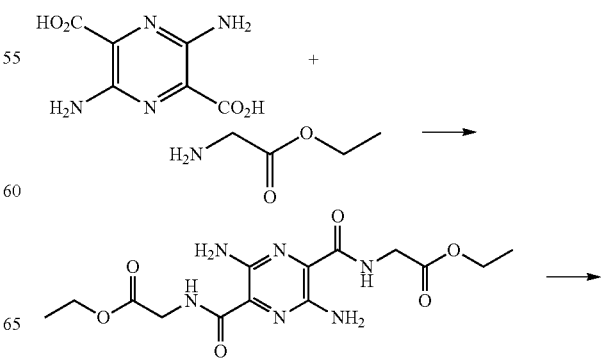

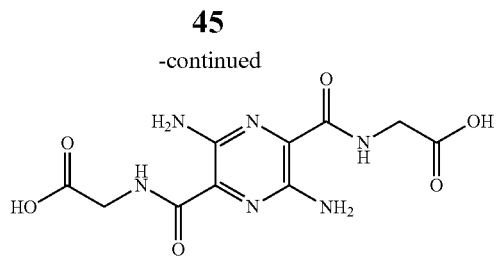

Step 1. Formation of diethyl 2,2'-((3,6-diaminopyrazine-2,5-dicarbonyl) bis(azanediyl))diacetate A round-bottom flask (300 mL) equipped with a magnetic stir bar was charged with 3,6-diaminopyrazine-2,5-dicarboxylic acid (5.0 g), ethyl glycinate hydrochloride (5.04 g), EDC.HCl (8.1 g), HOBt.H$_2$O (8.0 g), and DIPEA (5.9 g) in DMF (anhydrous, 200 mL). A dry argon atmosphere was maintained throughout the course of the reaction. The pyrazine was combined with glycinate, and DMF was added with stirring, under an inert atmosphere. To this was added base and HOBt. After about 15 minutes, EDC was added portionwise over 45 min, and the reaction stirred at ambient temperature under Ar overnight. The reaction mixture was concentrated in vacuo until a viscous, semi-solid was obtained. The semi-solid was treated with toluene (ca. 30 mL) and volatiles removed in vacuo. After cooling a solid formed. The crude product was dissolved in 500 mL EtOAc and mixed until two layers formed. The solution was washed with brine and saturated NaHCO$_3$ and the aqueous layer was removed. The water layer was washed (2× EtOAc, 150 mL), and the organic layers combined. The organic layer was washed with aqueous NaHSO$_4$, saturated brine, dried over Na$_2$SO$_4$, and concentrated to give an solid. Isolated yield: 5.46 g. HPLC analysis 96.9%. M/z 369.2. $^1$H and $^{13}$C NMR consistent with proposed structure. This product was taken forward without further purification.

Step 2. Formation of 2,2'-((3,6-diaminopyrazine-2,5-dicarbonyl) bis(azanediyl))diacetic Acid The crude product from Step 1 (700 mg) was dissolved in 40 mL THF with 10 mL water (DI). LiOH (4.2 equivalents) was added, and the mixture stirred overnight at ambient temperature under an inert atmosphere. HPLC analysis indicated complete conversion to desired diacid (M/z=313.3). The reaction mixture was centrifuged (3000 rpm for 3 minutes), and the supernatant checked by HPLC and discarded. The remaining solid was converted to the di-sodium salt by treating with NaOH (6.25 N, 2 equivalents), and the resulting solution filtered (0.22 micron). The solution was lyophilized to give a solid that was >95% pure by HPLC. The di-sodium salt was converted to diacid by adding slightly more than two equivalents of TFA followed by reverse phase preparative column. Proton and carbon NMR were consistent with proposed structure.

Example 16

(2S,2'S)-2,2'-((3,6-diaminopyrazine-2,5-dicarbonyl) bis(azanediyl)) dipropionic Acid ("L-Alanine Isomer")

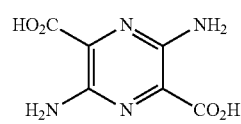

+

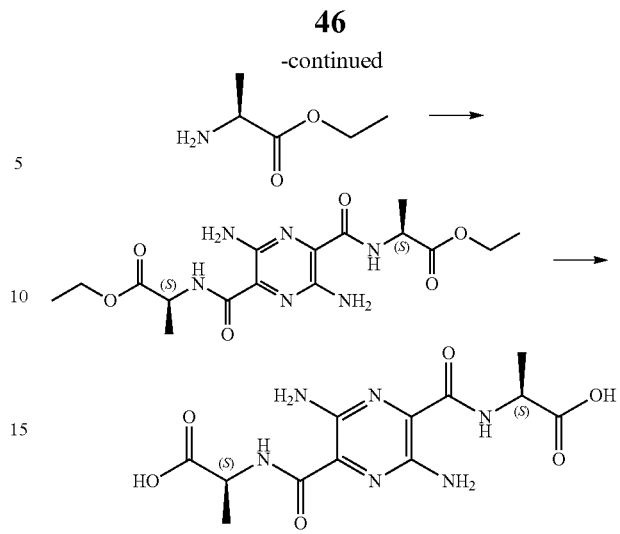

Step 1. Formation of diethyl 2,2'-((3,6-diaminopyrazine-2,5-dicarbonyl)bis (azanediyl))(2S,2'S)-dipropionate Under an inert atmosphere, a flame dried round-bottom flask (100 mL) was charged with 3,6-diaminopyrazine-2,5-dicarboxylic acid (1.0 g), ethyl L-alaninate hydrochloride (1.86 g), EDC.HCl (2.70 g), HOBt.H$_2$O (2.65 g) in DMF (anhydrous, 80 mL). Triethylamine was added (1.50 g). After 16 hours at ambient temperature, the reaction volatiles were removed in vacuo. A semi-solid was isolated. Water was added (70 mL) and the mixture allowed to stand for about an hour. During this time a precipitate formed so the mixture was centrifuged, and a solid isolated that was air dried overnight. This material was dissolved in EtOAc and washed with water, citric acid and saturated sodium bicarbonate. The organic layer dried (anhydrous sodium sulfate) and concentrated in vacuo to give a solid product (1.38 g). HPLC purity>95% purity. The crude product was used in the next step without further purification.

Step 2. Formation of (2S,2'S)-2,2'-((3,6-diaminopyrazine-2,5-dicarbonyl)bis (azanediyl)) dipropionic Acid The crude product from Step 1 (1.0 g) was dissolved in THF (30 mL), and LiOH.H$_2$O (4 equiv.) dissolved in water (10 mL) was added at ambient temperature. After an hour, the volatiles were removed in vacuo. The product was purified by preparative reverse phase HPLC and lyophilized to obtain a solid with >95% purity of desired diacid product. Proton and carbon NMR were consistent with proposed structure.

Example 17

2,2'-(3,6-diaminopyrazine-2,5-dicarbonyl)bis (azanediyl))bis(2-methylpropanoic acid) ("Dimethyl Glycine Isomer")

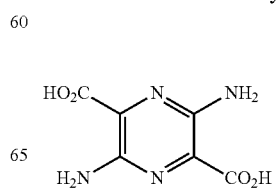

+

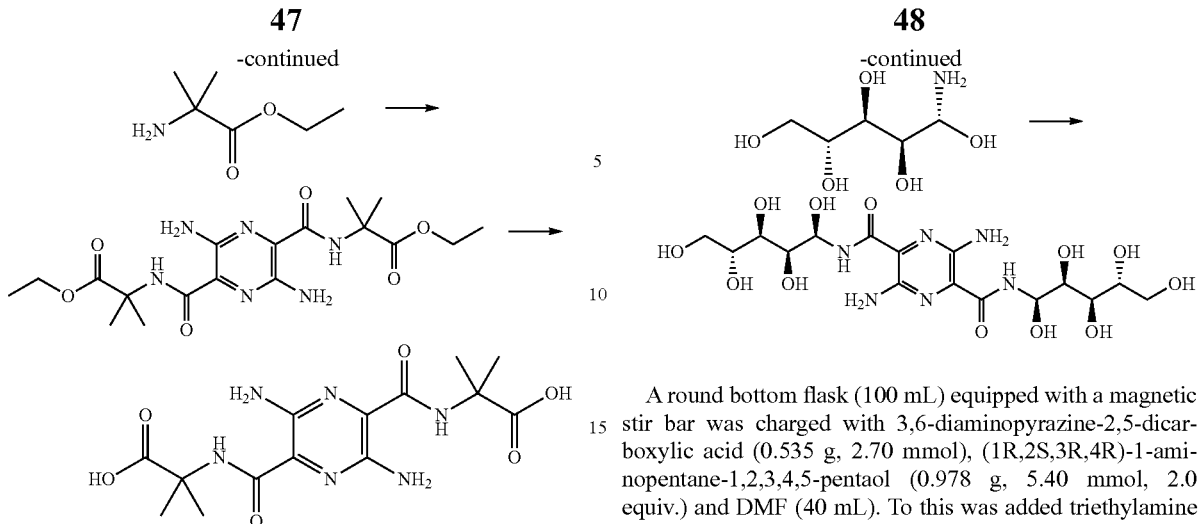

Step 1. Formation of diethyl 2,2'-((3,6-diaminopyrazine-2,5-dicarbonyl)bis (azanediyl))bis(2-methylpropanoate)

Under an inert atmosphere, a flame dried round-bottom flask (100 mL) was charged with 3,6-diaminopyrazine-2,5-dicarboxylic acid (1.0 g), ethyl gem-dimethyl 3-amino propanoic acid hydrochloride (1.86 g), EDC.HCl (2.70 g), HOBt.H$_2$O (2.65 g) in DMF (anhydrous, 80 mL). The reaction was initiated by addition of triethylamine (1.50 g) and maintained at ambient temperature for 72 hr. Volatiles were removed in vacuo. A dark viscous liquid was isolated. After cooling, it taken up in acetonitrile (about 100 mL) and allowed to stand for about an hour. A precipitate formed that was isolated by centrifugation and dried to obtain 1.30 g of the di-ethyl ester (61%) have a purity by RPHPLC>95%. This crude product was used directly in the next step.

Step 2. Formation of 2,2'-((3,6-diaminopyrazine-2, 5-dicarbonyl)bis (azanediyl))bis(2-methylpropanoic acid)

The crude product from Step 1 (1.0 g) was dissolved in THF:water (40 mL:5 mL). To this was added LiOH in water (2.5 equivalents in 0.5 mL DI water). Another two equivalents of LiOH was added to the reaction mixture and the reaction allowed to proceed overnight at ambient temperature. Upon completion the reaction mixture was acidified with TFA until pH of about 4 has been reached. The product was isolated by preparative RPHPLC. M/z 369.13. Proton and carbon NMR were consistent with proposed structure.

Example 18

3,6-diamino-N$^2$,N$^5$-bis((1R,2S,3R,4R)-1,2,3,4,5-pentahydroxypentyl) pyrazine-2,5-dicarboxamide

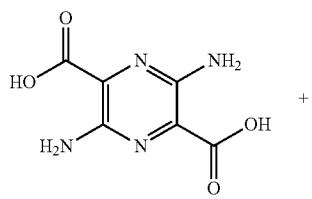

+

A round bottom flask (100 mL) equipped with a magnetic stir bar was charged with 3,6-diaminopyrazine-2,5-dicarboxylic acid (0.535 g, 2.70 mmol), (1R,2S,3R,4R)-1-aminopentane-1,2,3,4,5-pentaol (0.978 g, 5.40 mmol, 2.0 equiv.) and DMF (40 mL). To this was added triethylamine (0.546 g, 0.76 mL, 5.40 mmol, 2.0 equiv.) and PyBop (3.1 g, 5.94 mmol, 2.2 equiv.). After an hour the reaction was complete by HPLC analysis and concentrated in vacuo keeping the temperature below 40° C. The mixture was taken up in water (10 mL), passed through a Sephadex G-10 column and fractions containing a fluorescent product collected and lyophilized to obtain an impure solid. The target product, 3,6-diamino-N$^2$,N$^5$-bis((1R,2S,3R,4R)-1,2,3,4,5-pentahydroxypentyl)pyrazine-2,5-dicarboxamide, was obtained by preparative C-18 RPHPLC: 160 mg, HRMS (theoretical) M+Na=547.1970; HRMS (Observed) M+Na=547.1969.

Example 19

Protocol for Assessing Renal Function

Figure 1:
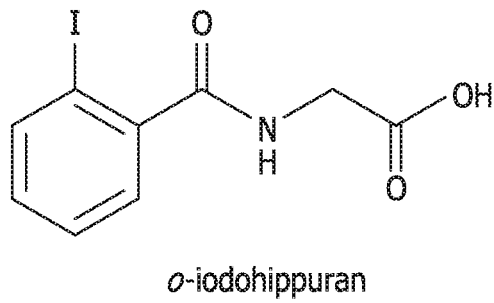
FIG. 1 illustrates several known contrast agents for renal function monitoring.
Figure 1:
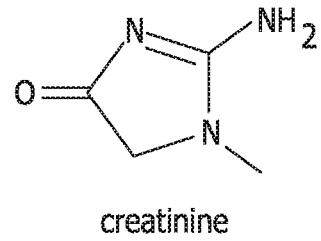
Figure 1:
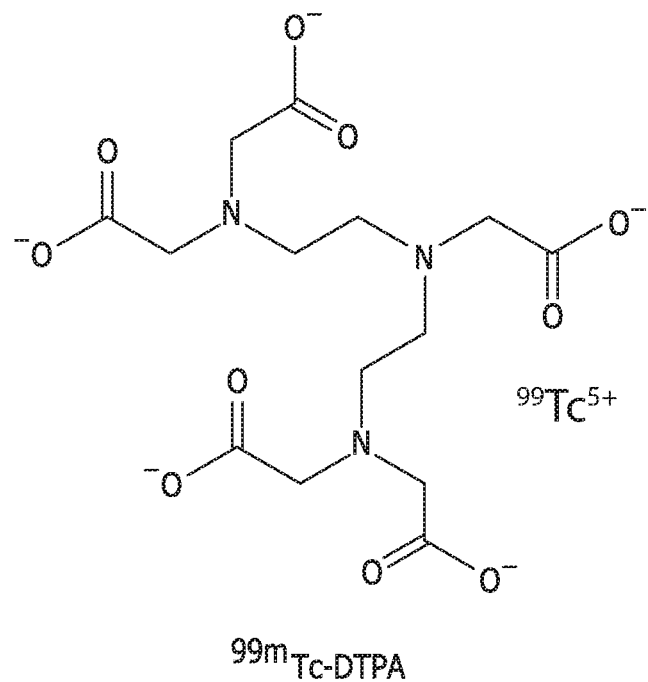
Figure 1:
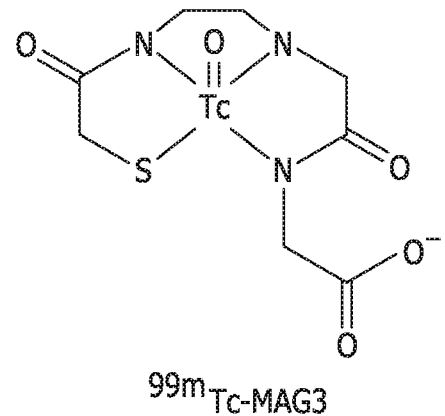
Figure 2:
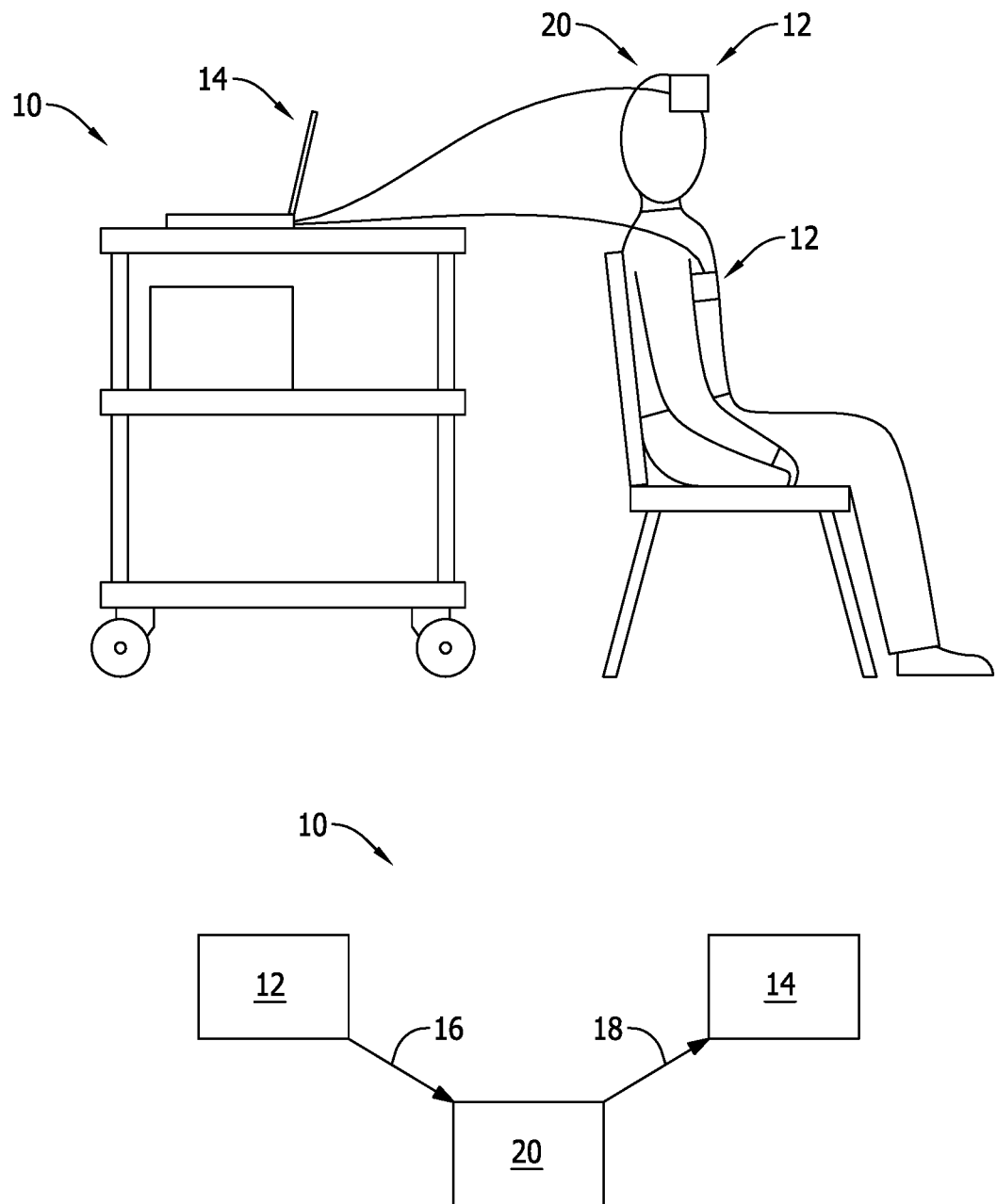
FIG. 2 is an illustration of a system for monitoring the GFR in a patient.

An example of an in vivo renal monitoring assembly 10 is shown in FIG. 2 and includes a light source 12 and a data processing system 14. The light source 12 generally includes or is interconnected with an appropriate device for exposing at least a portion of a patient's body to light therefrom. Examples of appropriate devices that may be interconnected with or be a part of the light source 12 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source may be employed in the renal monitoring assembly 10. In one aspect, the light sources are LEDs where one of the LEDs emits light near the absorbance maximum of the tracer agent while the second LED emits light near the fluorescence emission maximum of the tracer agent. For example, one LED emits light at 450 nm while the second LED emits light at 560 nm.

Still referring to FIG. 2, the data processing system 14 of the renal monitoring assembly may be any appropriate system capable of detecting spectral energy and processing data indicative of the spectral energy. For instance, the data processing system 14 may include one or more lenses (e.g., to direct and/or focus spectral energy), one or more filters (e.g., to fitter out undesired wavelengths of spectral energy), a photodiode or photomultiplier (e.g., to collect the spectral energy and convert the same into electrical signal indicative of the detected spectral energy), an amplifier (e.g., to amplify electrical signal from the photodiode or photomultiplier), and a processing unit (e.g., to process the electrical signal from the photodiode or photomultiplier). The data processing system 14 is preferably configured to manipulate collected spectral data and generate an intensity/time profile and/or a concentration/time curve indicative of renal clearance of a pyrazine derivative of the present disclosure from patient 20. Indeed, the data processing system 14 may be configured to generate appropriate renal function data by comparing differences in manners in which normal and impaired cells remove the pyrazine derivative from the bloodstream, to determine a rate or an accumulation of the pyrazine derivative in organs or tissues of the patient 20, and/or to provide tomographic images of organs or tissues having the pyrazine derivative associated therewith.

By way of example and not limitation, in one aspect the system comprises two silicon photomultipliers. The first photomultiplier includes a long pass filter while the second photomultiplier is unfiltered. This arrangement permits both the fluorescence emission and diffuse reflectance at the excitation and emission wavelengths to be measured. In one such embodiment, the fluorescence and diffuse reflectance measurement are combined into an Intrinsic Fluorescence measurement that is compensated for variations in tissue optical properties. An example formula for combining the measurements is provided in Equation 1.

In one aspect for determining renal function, an effective amount of a pyrazine derivative is administered to patients in need thereof (e.g., in the form for a pharmaceutically acceptable composition). At least a portion of the body of the patient 20 is exposed to visible and/or near infrared light from the light source 12 as indicated by arrow 16. For instance, the light from the light source 12 may be delivered via a fiber optic that is affixed to an ear of the patient 20. The patient may be exposed to the light from the light source 12 before or after administration of the pyrazine derivative to the patient 20. In some cases, it may be beneficial to generate a background or baseline reading of light being emitted from the body of the patient 20 (due to exposure to the light from the light source 12) before administering the pyrazine derivative to the patient 20. When the pyrazine derivative that is in the body of the patient 20 is exposed to the light from the light source 12, the pyrazine derivative emanates light (indicated by arrow 18) that is detected/collected by the data processing system 14. Initially, administration of the pyrazine derivative to the patient 20 generally enables an initial spectral signal indicative of the initial content of the pyrazine derivative in the patient 20. The spectral signal then tends to decay as a function of time as the pyrazine derivative is cleared from the patient 20. This decay in the spectral signal as a function of time is indicative of the patient's renal function. Additionally, if the tracer agent is injected into the vascular space of a patient, the initial kinetics reflect the equilibration of the tracer agent into the entire extracellular space of the patient. In some aspects, this equilibration is complete in less than 2 hours.

For example, in a first patient exhibiting healthy/normal renal function, the spectral signal may decay back to a baseline in a time of T. However, a spectral signal indicative of a second patient exhibiting deficient renal function may decay back to a baseline in a time of T+4 hours. The extent of renal impairment or deficiency will affect the length of time required for the signal to decay back to baseline. A greater degree of renal impairment will require a longer period of time. As such, the patient 20 may be exposed to the light from the light source 12 for any amount of time appropriate for providing the desired renal function data. Likewise, the data processing system 14 may be allowed to collect/detect spectral energy for any amount of time appropriate for providing the desired renal function data.

Additionally, GFR determination in a patient is not limited to a single determination based on a single administration of the tracer agent. The time between administration of the tracer agent and when it becomes undetectable in the patient may be subdivided into multiple smaller segments, and the GFR of the patient calculated for each smaller segment. In some aspects the time segments can overlap. By way of example and not limitation, if the entire time period before the tracer agent become undetectable is 24 hours, then the time period can be divided into four equal segments of six hours; each new time segment beginning at the end of the previous segment. In yet another aspect, the time segments may overlap. For example, each individual time segment may be four hours long, but a new time segment could begin every two hours. This would generate overlapping segments throughout the measurement. To more fully illustrate this nonlimiting example, if the tracer agent was administered at time equals 0 and became undetectable at time equals 24 hours, then the following time segments may be generated: 0-4 hours, 2-6 hours, 4-8 hours, 6-10 hours, 8-12 hours, 10-14 hours, 12-16 hours, 14-18 hours, 16-20 hours, 18-22 hours, and 20-24 hours. The GFR of the patient can be calculated in each time segment individually. This data would them be used to more fully evaluate the health of the kidneys of a patient. The time segment may be any length that permits GFR determination and may be 15 minutes, 30 minutes, 45 minutes, 1 hour, 2 hours, 3 hours, 4 hours, 5 hours, 6 hours, 8 hours, 10 hours or 12 hours. Additionally, the time segments do not have to be identical during the measurement. The length of each time segment is selected individually without regard to any other time segment.

Pharmacokinetic Study Results

In a clinical study, 60 human patients were administered MB-102 ((2R,2'R)-2,2'-((3,6-diaminopyrazine-2,5-dicarbonyl)bis(azanediyl))bis(3-hydroxypropanoic acid)) prepared in Example 12) intravenously. Blood and urine were collected in addition to the methods and techniques disclosed herein. Standard pharmacokinetic data was collected and comparison was made between the methods and techniques disclosed herein to Omnipaque® (iohexol), a known contrast agent used for GFR determination.

Shown in FIGS. 3A to 3D are data collected from the 60 human patients tested with MB-102. Plasma pharmacokinetic data was collected and analyzed using methods known in the art and compared to the data measured using the methods and techniques disclosed herein.

Figure 3A:
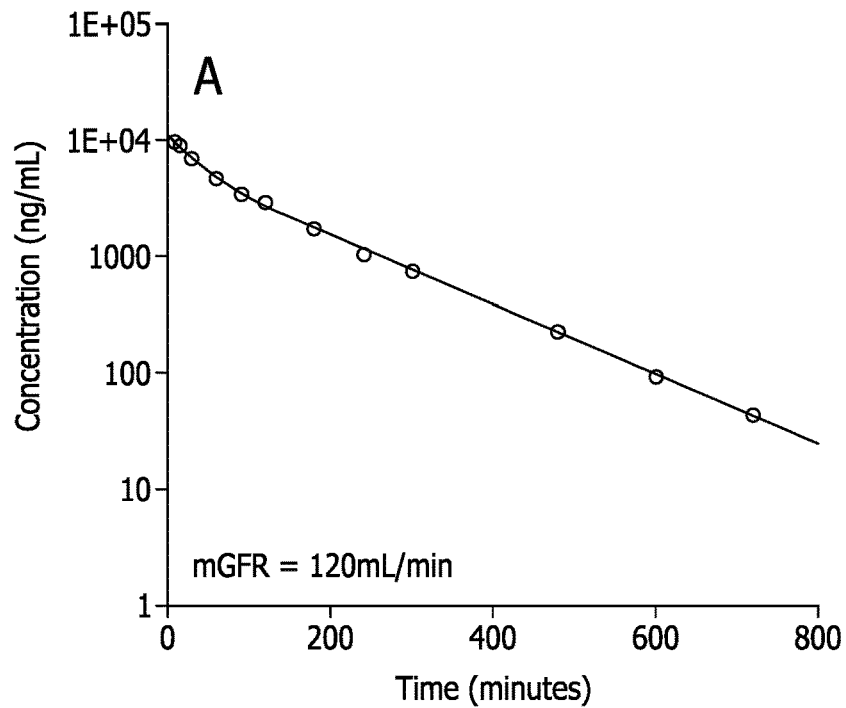
FIGS. 3A, 3B, 3C and 3D are graphs of the clearance of MB-102 illustrating a two-compartment pharmacokinetic model in four different patients having different GFR values ranging from 120 mL/min (3A) to 25 mL/min (3D).
Figure 3B:
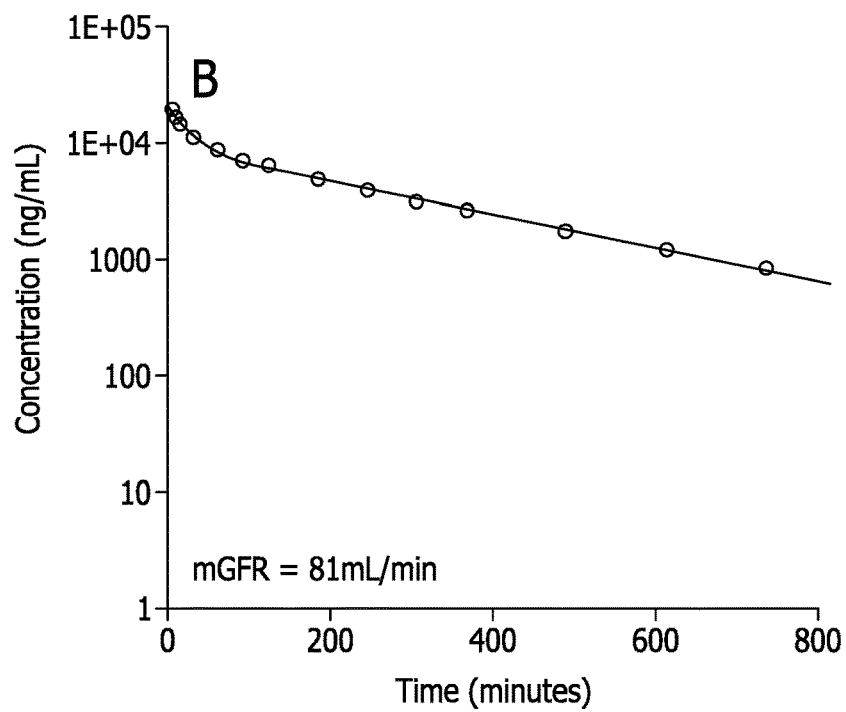
Figure 3C:
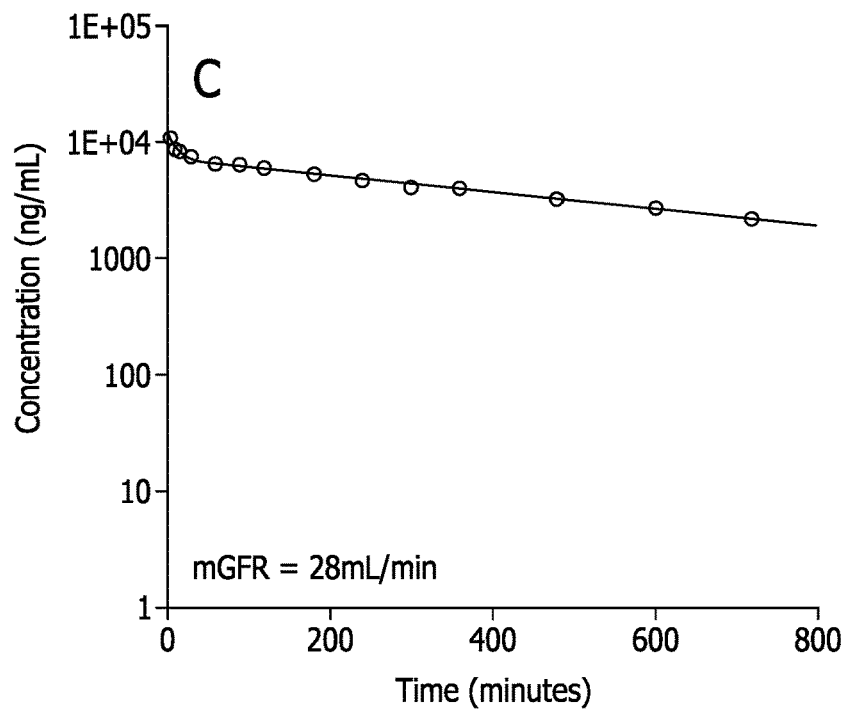
Figure 3D:
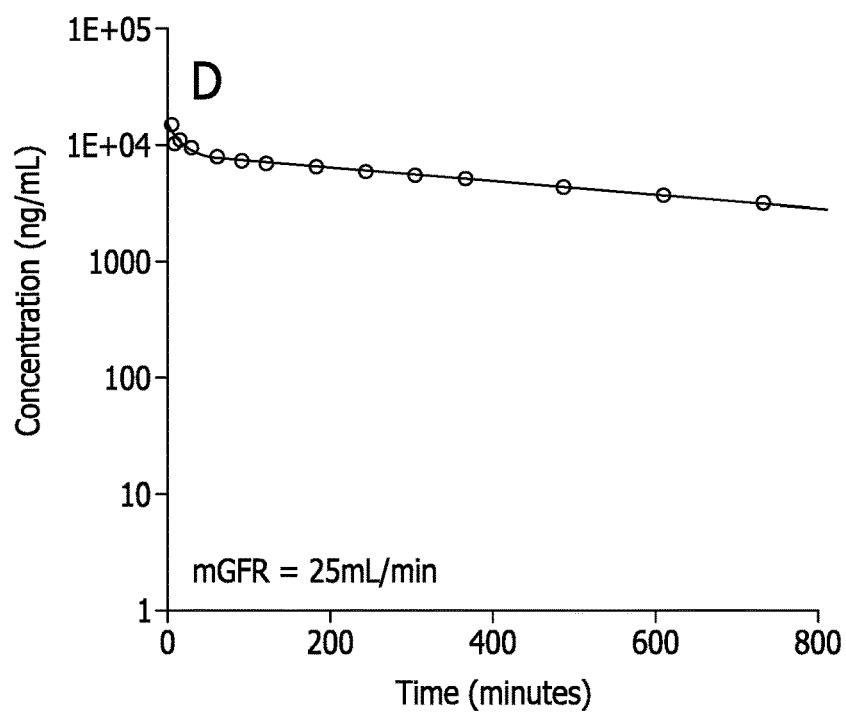

FIGS. 3A to 3D illustrate a two compartment pharmacokinetic model for the elimination of MB-102. The model is consistent for patients regardless of their GFR values. FIG. 3A is for patients having normal kidney function having a measured GFR (mGFR) of 120 mL/min. FIG. 3B is for patients having a mGFR of 81 mL/min. FIG. 3C is for patients having a mGFR of 28 mL/min. FIG. 3D is for patients having a mGFR of 25 mL/min. The first compartment in the two compartment model is the vascular to tissue equilibrium while the second compartment illustrates renal excretion only. On average, the time for equilibration is about one hour, and is subject dependent.

Figure 4:
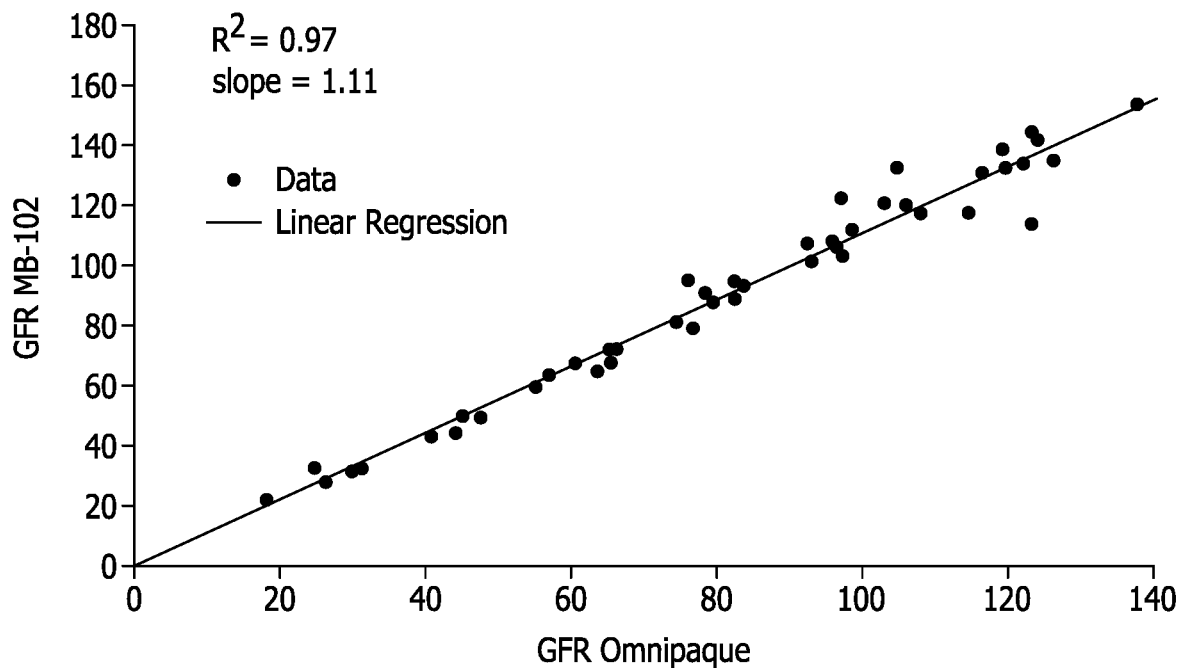
FIG. 4 is a graph comparing of the GFR determined using MB-102 compared to Omnipaque®.

Shown in FIG. 4 is comparative data for the GFR measured using Omnipaque® using traditional methods in comparison to MB-102, using the methods disclosed herein for patients having an eGFR ranging from about 20 to about 140. The data shows a correlation coefficient of 0.97. This indicates that the method for determining patient GFR used herein provides similar results compared to known methods.

Figure 5:
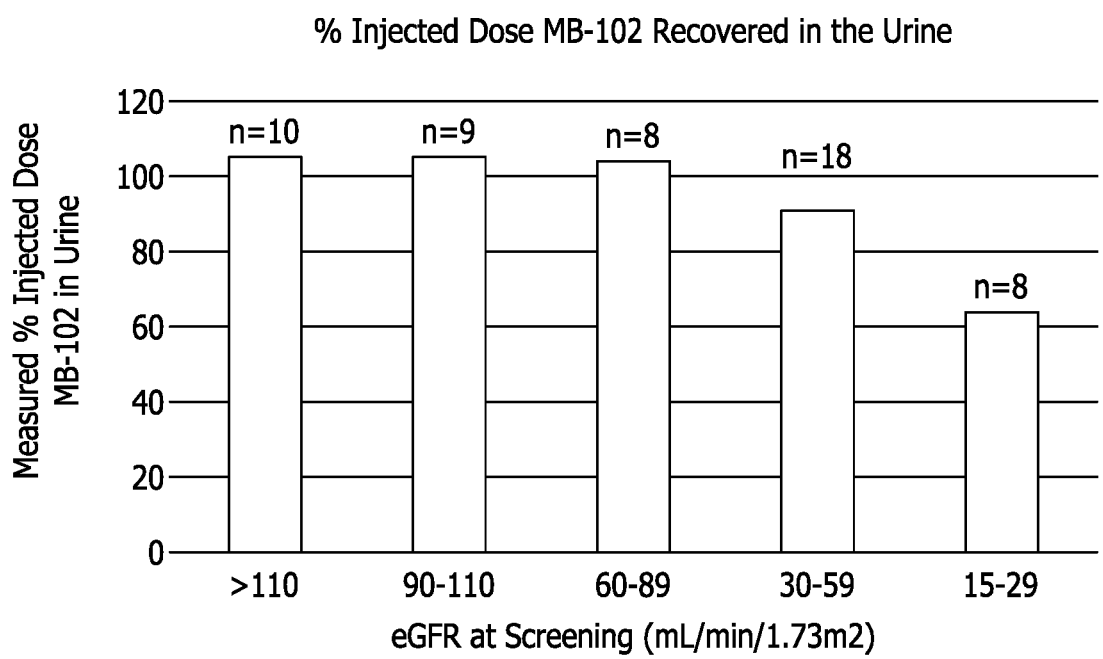
FIG. 5 is a bar graph of the percent recovery of MB-102 from the urine of human patients after 12 hours.

As part of the clinical 1 study for MB-102, urine was collected from patients for 12 hours to determine the amount recovered and degree of secondary metabolism. As shown in FIG. 5, for patients having an eGFR greater than 60, greater than 99% of MB-102 was recovered unmetabolized after 12 hours. For patients having a mGFR value below 60, MB-102 a lower percentage was recovered but it was likewise unmetabolized. For patients having normal, stage 1 and stage 2 renal function, 12 hour collection time was sufficient for greater than 99% recovery of MB-102. In view of the pharmacokinetic data and the plasma half-life determination, less than complete collection is readily understood for patients having more serious renal function impairment.

Figure 6:
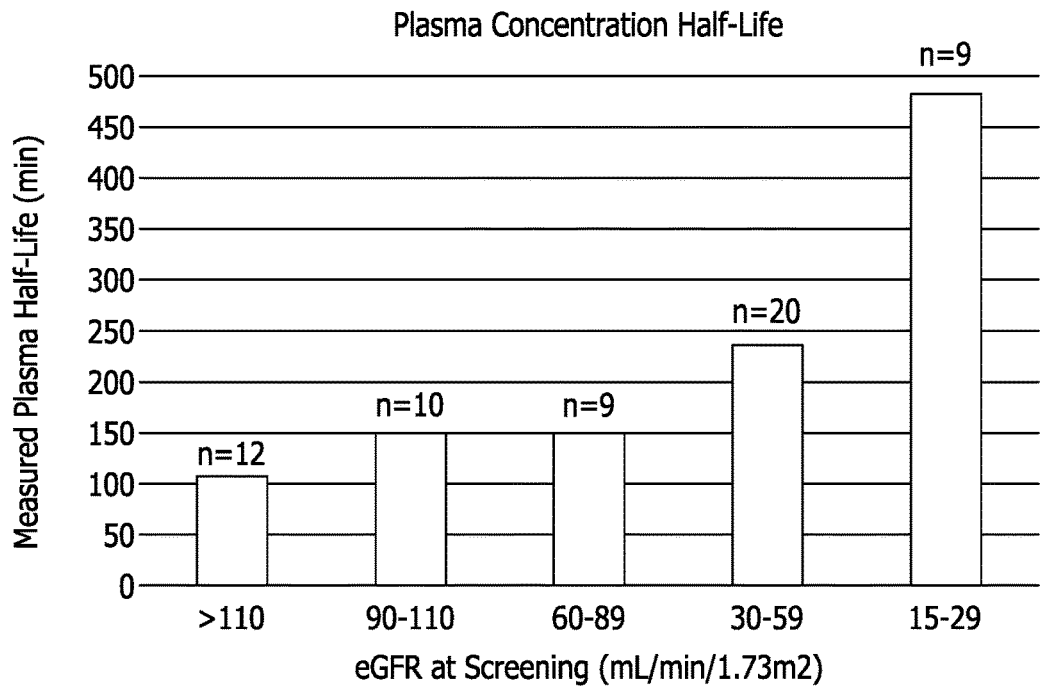
FIG. 6 is a bar graph of the plasma concentration half-life of MB-102 in human patients.

Shown in FIG. 6 is the plasma concentration half-life of MB-102 for patients having either normal kidney function, stage 1 renal impairment, stage 2 renal impairment, stage 3 renal impairment, or stage 4 renal impairment. Based on this data, it is clear that in the urine collection study above, longer than 24 hours will be required to clear all of MB-102 from a patient's bloodstream. The normal renal function group has an average plasma half-life of two hours, thus the 12 hour collection time is about 6 half-lives and is enough time to excrete most of the injected dose. The stage 2 and 3 groups have an average plasma half-life of 2.5 hours, resulting in about 5 half-lives of excretion time which is also enough to collect most of the injected dose. However, the 4 hour half-life for stage 3 and the 8 hour half-life for stage 4 does not allow all the injected dose to be collected in the 12 hour window for the clinical study.

Figure 7:
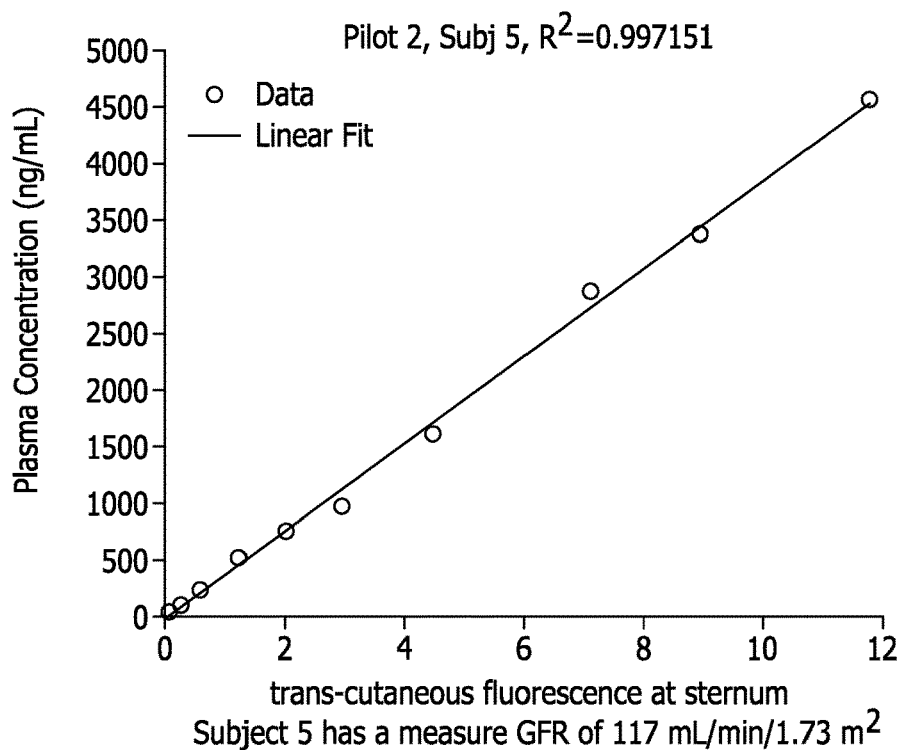
FIG. 7 is a graph showing the correlation over time between the plasma concentration of MB-102 and the transdermal fluorescence intensity, in a patient with a GFR of 117 mL/min/1.73 $m^2$.
Figure 8:
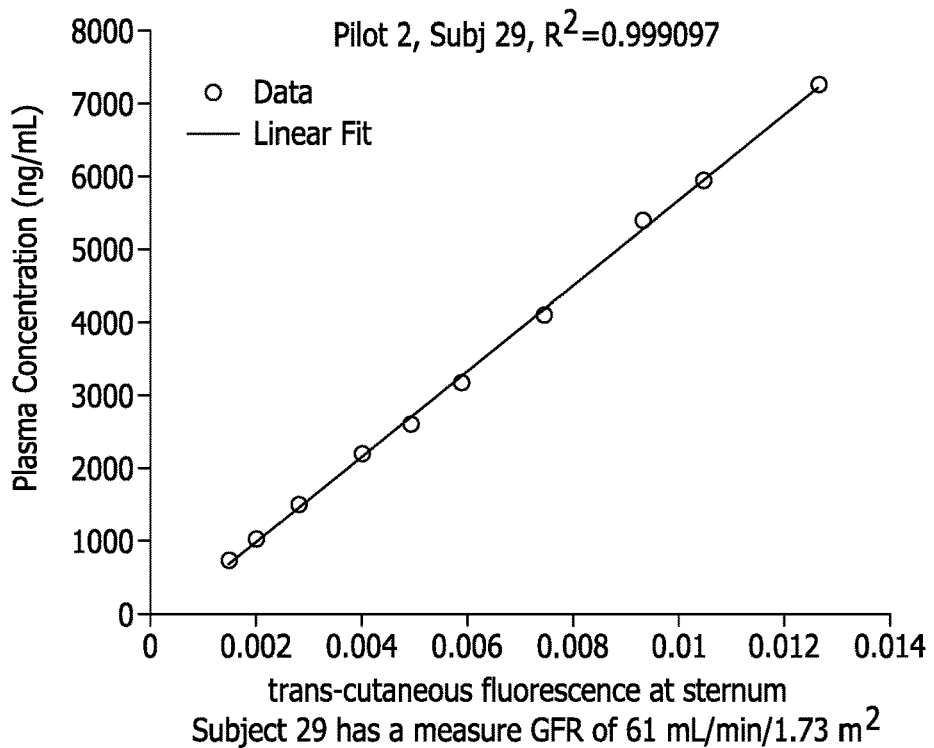
FIG. 8 is a graph showing the correlation over time between the plasma concentration of MB-102 and the trans-cutaneous fluorescence intensity, in a patient with a GFR of 61 mL/min/1.73 $m^2$.
Figure 9:
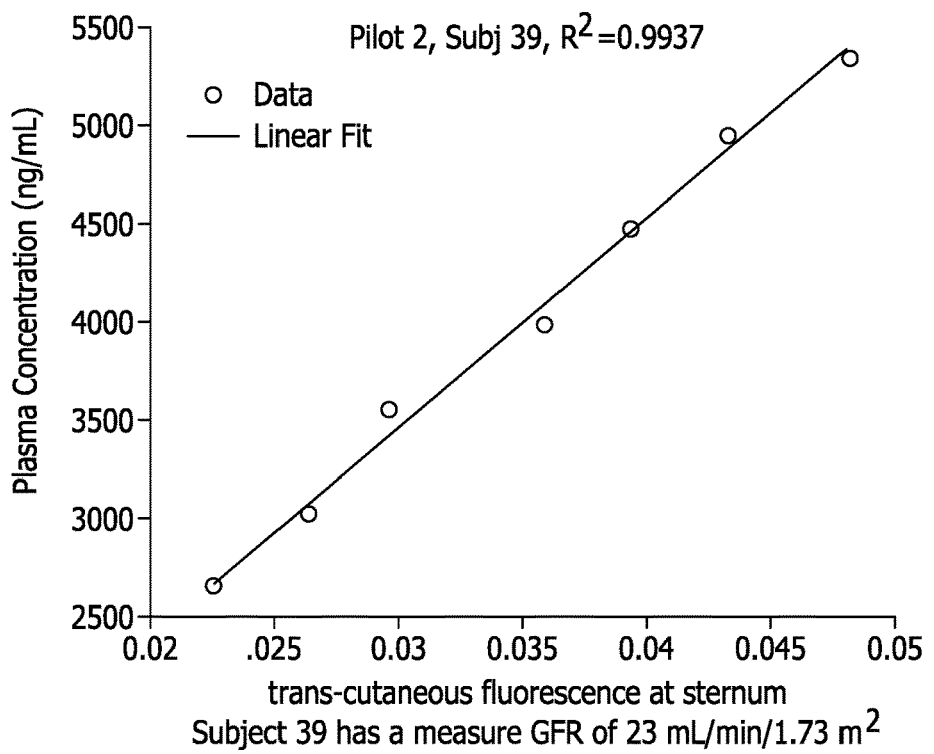
FIG. 9 is a graph showing the correlation over time between the plasma concentration of MB-102 and the trans-cutaneous fluorescence intensity in a patient with a GFR of 23 mL/min/1.73 $m^2$.

In a clinical study, the plasma pharmacokinetics was correlated as a function of time (starting 2 hours after tracer agent injection and continuing to the end of the 12 hr study period) with the transdermal fluorescence pharmacokinetics measured on the sternum of the patients. High correlations between the plasma concentrations and fluorescence intensity were observed for patients spanning a wide range of GFR values. Shown in FIGS. 7, 8 and 9 are three individual patients with GFR values between 23 mL/min/1.73 m² (stage 3b renal impairment) to 117 mL/min/1.73 m² (normal kidney function). Thus, the plasma pharmacokinetics are correlated with the transdermal fluorescence for MB-102, for patients spanning a wide GFR range.

Transdermal GFR Determination (Fits to Full Data Set)

Kinetic analysis was done using LabView, Matlab, WinNonlin and Microsoft Excel, version 2010, as follows. The transdermal fluorescence data were fit to a single exponential function between 2 hours (relative to the time of injection, ensuring that the tracer agent has equilibrated across the extracellular space) and the end of the available data (typically about 12 hours). For each subject two fits were performed: (1) with the offset fixed at zero, (2) with the offset allowed to vary. The exponential time constant determined from the fits is referred to as the renal decay time constant (RDTC).

Linear regression, outlier exclusion, and calculation of the correlation coefficient ($R^2$) and standard error of calibration (SEC) were performed in Microsoft Excel, version 2010. The inverse of the RDTC was correlated with GFR using 4 different methods of GFR determination:

Un-normalized—the GFR, as determined from the plasma PK analysis of both Iohexol and MB-102.

BSA-normalized—the height and weight were used to estimate each subject's body surface area (BSA), according to method of Mosteller (N Engl J Med, 1987; 317(17)). The GFR determined by plasma PK analysis was divided by the ratio of the computed BSA to 1.73 m² (the BSA for a "standard" sized patient).

$V_d$-normalized (Method 1)—the GFR determined by plasma PK analysis was divided by the ratio of the volume of distribution ($V_d$) (also determined from the PK analysis) to 14,760 mL, the $V_d$ for a "standard" sized patient. The $V_d$ for a standard-sized patient was determined by forcing the average nGFR across all Group 1 patients to be equal for the $V_d$ and BSA normalization methods. "nGFR" is used here to refer to generalized methods (including both BSA and $V_d$) in which GFR is normalized to body size.

$V_d$-normalized (Method 2)—a single exponential, with offset fixed at zero, was fit to the MB-102 plasma concentrations vs. time, between 2 and 12 hours (relative to the time of tracer agent injection). The inverse of the fitted time constant was multiplied by 14,760 mL (the $V_d$ for a "standard" sized patient; see above), resulting in GFR normalized by the volume of distribution.

Correlation coefficients ($R^2$) and standard errors of calibration (SEC) for plots of plasma-derived GFR vs transcutaneous renal clearance rate are summarized in Table 2 and FIGS. 12 to 18. In agreement with Rabito's previous findings (J Nucl Med, 1993; 34(2): 199-207), normalization of the GFR by BSA increases $R^2$ and decreases SEC, confirming the hypothesis that the rate of renal clearance of MB-102 provides a measure of the kidney efficiency that is independent of body size. Further, these results show that the volume of distribution ($V_d$) of the tracer agent is also effective for normalizing the GFR to a standard body size. As can be seen in the in Table 2, the BSA and the second $V_d$, body size normalization methods were equally effective when no outlier exclusion methods were applied, and the offset for the RDTC fits was fixed at zero.

TABLE 2

| GFR Compound | GFR norm. method | Offset Method | Outlier Exclusions | $R^2$ | N | SEC Absolute (mL/min) | SEC Relative (%) |
|---|---|---|---|---|---|---|---|
| Iohexol | none | Fixed at 0 | none | 0.6494 | 55 | 19.0 | 25.1% |
| Iohexol | BSA | Fixed at 0 | none | 0.7804 | 55 | 13.5 | 19.1% |
| Iohexol | $V_d$ | Fixed at 0 | none | 0.7978 | 55 | 14.3 | 21.0% |
| MB-102 | none | Fixed at 0 | none | 0.6911 | 55 | 21.0 | 24.7% |
| MB-102 | BSA | Fixed at 0 | none | 0.8242 | 55 | 13.7 | 18.0% |
| MB-102 | $V_d$ (1) | Fixed at 0 | none | 0.8016 | 55 | 15.8 | 20.1% |
| MB-102 | $V_d$ (2) | Fixed at 0 | none | 0.8211 | 55 | 14.1 | 19.3% |

RDTC Fitting Offset Method

Figure 18:
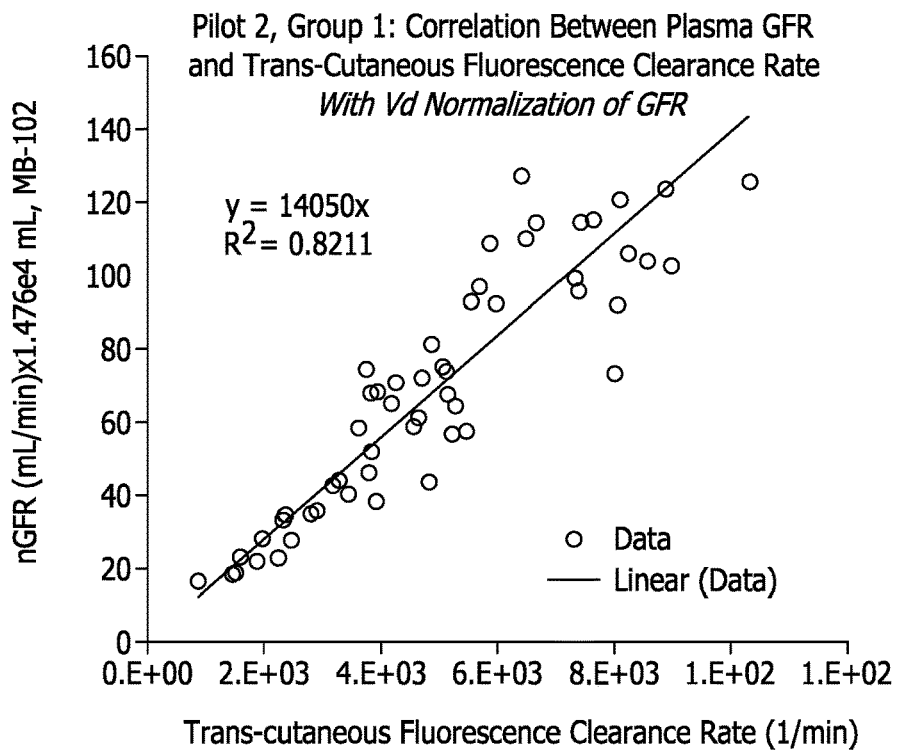
FIG. 18 is a graph correlating the plasma-determined GFR to the trans-cutaneous fluorescence clearance rate: GFR by MB-102, $V_d$—Normalized, Method 2 (No outlier exclusion; fixed offset fitting method).
Figure 19:
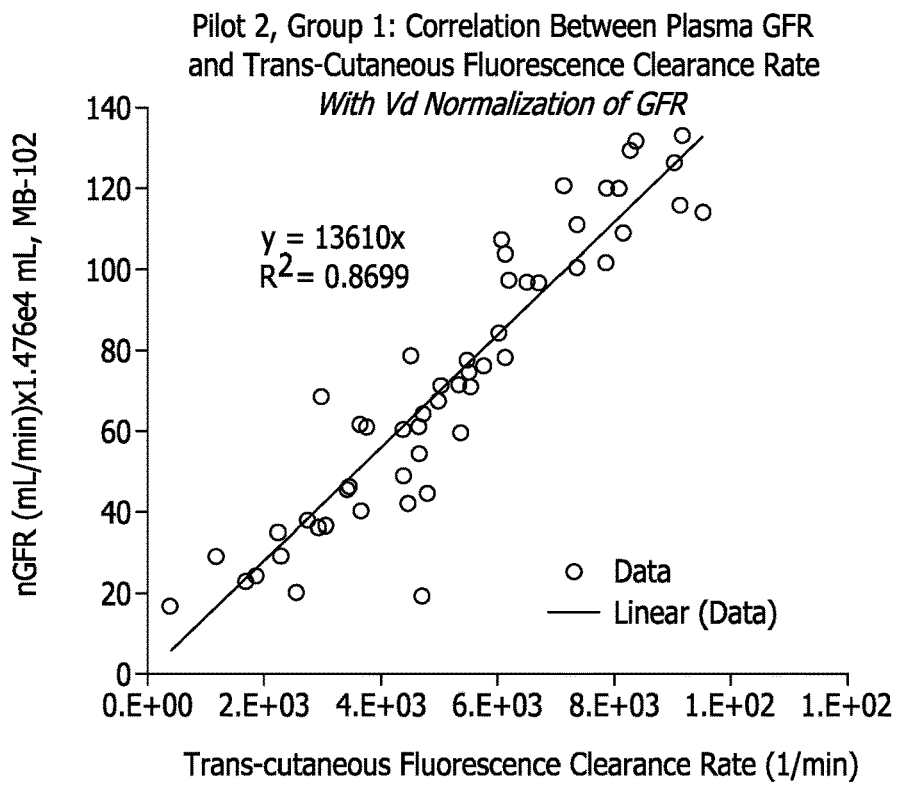
FIG. 19 is a graph correlating the plasma-determined GFR to the trans-cutaneous fluorescence clearance rate: Variable Offset Method (No outlier exclusion; GFR determination by MB-102 with $V_d$ normalization method 2).

The transdermal fluorescence kinetics were fit by two different offset methods: (1) offset fixed at zero, and (2) offset allowed to vary. FIGS. 18 and 19 show the resulting correlation plots for the fixed and variable offset methods, respectively. Note that when the offset is fixed at zero (FIG. 18), the data is clustered more tightly in the low GFR region of the correlation plot, whereas when the offset is allowed to vary (FIG. 19), the data clustering is tighter in the high GFR region.

This observation points to instability in the baseline fluorescence. In healthy subjects with a high rate constant for renal clearance, the fluorescence agent was cleared before the end of the 12 hour data collection period. In these subjects it was observed that the final plateau level of the fluorescence did not always perfectly match the initial pre-injection baseline fluorescence. Allowing the offset to vary in the fits for these healthy subjects allowed the fits to compensate for this baseline uncertainty, thereby improving the reliability of the extracted clearance rate constant. However, in many subjects with compromised kidney function, the agent was not fully cleared within the 12 hour window in which the measurements were collected. In these subjects, including a variable offset in the fits was found to increase the uncertainty in the fitted clearance rate constant. By fixing the offset at zero, the reliability of the rate constant improved.

Figure 20:
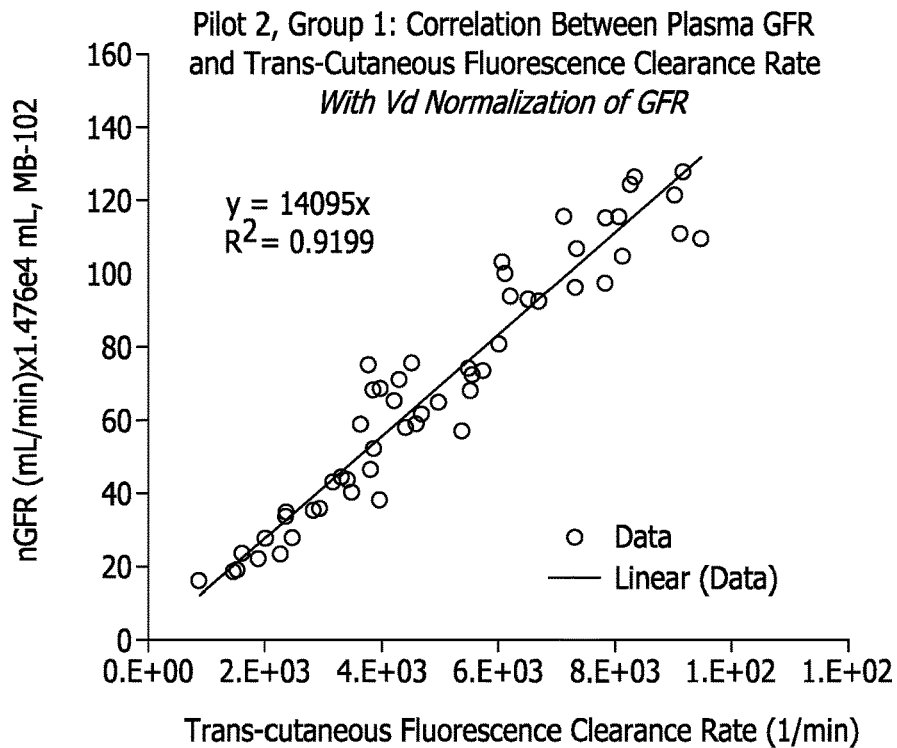
FIG. 20 is a graph correlating the plasma-determined GFR to the trans-cutaneous fluorescence clearance rate: Hybrid Offset Method (No outlier exclusion; GFR determination by MB-102 with $V_d$ normalization method 2).

Based on these observations, a hybrid offset method was developed. In the hybrid method, if a fit with the offset fixed indicates that the rate constant is high (i.e. healthy kidney function), then the offset is allowed to vary; otherwise (i.e. compromised kidney function) the offset is fixed. The optimum transition point was selected to maximize the $R^2$ and minimize the SEC, as shown in FIG. 25. The transition point shown on the x-axis is expressed as a time constant (in units of hours), which is the inverse of the clearance rate constant. As can be seen in the figure, the optimum time constant was in the range of 3.5 to 4.5 hours. A correlation plot employing the hybrid offset method (transition point: 3.5 hours) is shown in FIG. 20. A comparison of the fixed, variable, and hybrid offset methods, provided in Table 3, shows that the hybrid offset method results in substantial increase in $R^2$ and decrease in SEC compared to the other methods.

excluded because the sensor repeatedly over-heated (in all subsequent subjects the maximum allowed blue LED power level was reduced by 60%), (2) Subjects 8, 37, and 49 were excluded because the sensor came fully off of the skin and the original signal level could not be restored by re-attachment, (3) Subject 46 was excluded because the majority of the data was excluded during the pre-processing step (the probable cause was an unintended change in the LED power or detector gain after tracer agent injection).

Different metrics for further excluding subject data were tested, including: (1) correlation coefficient between the IF and fit; (2) root mean squared error (RMSE) of the IF relative to the fit; (3) the difference between the RDTC determined from a one exponential and a two exponential fit; (4) the signal-to-noise ratio, computed as the amplitude of the fitted exponential term divided by the RMSE; (5) the coefficient of variation (CV) of the rate constant, when fitted over multiple shorter time segments (e.g. 1-2 hours) within the full 12 hour data set; (6) the estimated error of the rate constant fitted to the IF; and (7) the estimated error of the GFR determined from the plasma data. None of these metrics includes a priori information about the correlation coefficient or SEC.

In one aspect, using data exclusion method (6) above, the estimated error of the rate constant fitted to the IF, divided by the rate constant (expressed as a relative error), gave the results shown in FIG. 26. By excluding subjects for which the relative error of the rate constant was greater than 1.4-1.8%, significant improvements in $R^2$ and SEC were observed. Choosing 1.75% as the cut-off metric, ten of the

TABLE 3

| GFR Compound | GFR norm. method | Offset Method | Outlier Exclusions | $R^2$ | N | SEC Absolute (mL/min) | SEC Relative (%) |
|---|---|---|---|---|---|---|---|
| MB-102 | BSA | Fixed at 0 | none | 0.8242 | 55 | 13.7 | 18.0% |
| MB-102 | BSA | Variable | none | 0.7721 | 55 | 15.7 | 38.0% |
| MB-102 | BSA | Hybrid | none | 0.8278 | 55 | 13.6 | 16.8% |
| MB-102 | $V_d(1)$ | Fixed at 0 | none | 0.8016 | 55 | 15.8 | 20.1% |
| MB-102 | $V_d(1)$ | Variable | none | 0.8554 | 55 | 13.5 | 39.3% |
| MB-102 | $V_d(1)$ | Hybrid | none | 0.9165 | 55 | 10.3 | 15.4% |
| MB-102 | $V_d(2)$ | Fixed at 0 | none | 0.8211 | 55 | 14.1 | 19.3% |
| MB-102 | $V_d(2)$ | Variable | none | 0.8699 | 55 | 12.0 | 38.1% |
| MB-102 | $V_d(2)$ | Hybrid | none | 0.9199 | 55 | 9.4 | 14.5% |

Data Exclusions

For some of the clinical subjects, the sensor did not remain fully attached to the skin over the full 12 hours of the study. Reattachment of the sensor post-injection often resulted in a significant shift in the signal level. This could be due to: (1) inhomogeneity in the skin auto-fluorescence, (2) inhomogeneity in the interstitial fluid fraction in the skin, or (3) changes in coupling efficiency of the light into and out of the skin. To address this in the future, the sensor was redesigned to have a smaller footprint and to be more adherent to the patient. In order to make use of the clinical data, some data exclusions were applied.

Figure 21:
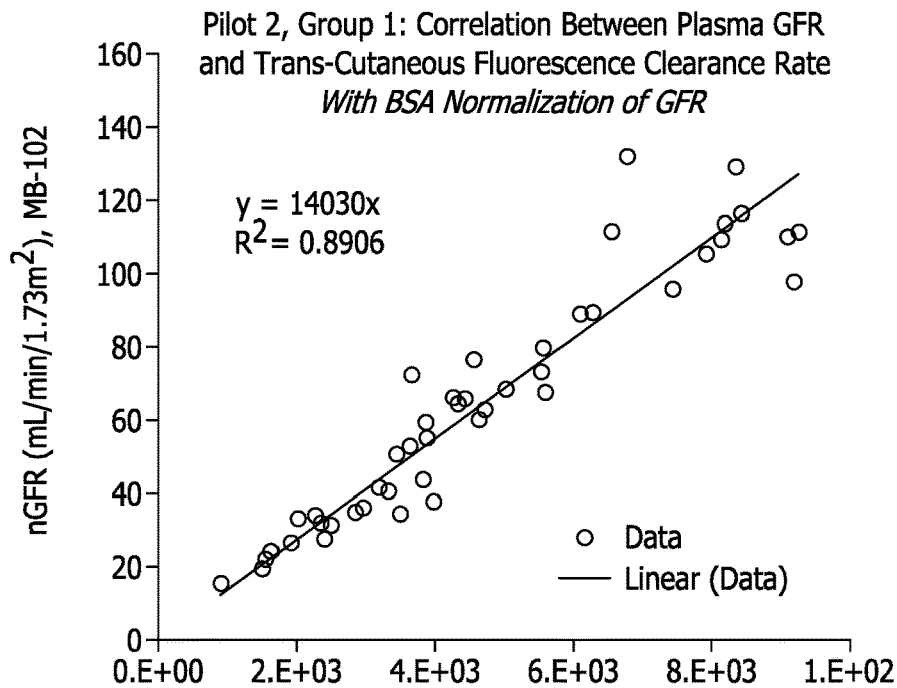
FIG. 21 is a graph correlating the plasma-determined GFR to the trans-cutaneous fluorescence clearance rate.

Five of the 60 clinical subjects were entirely excluded from the fluorescence kinetic analysis: (1) Subject 1 was 55 subjects were excluded. The resulting correlation plots are shown in FIGS. 21 and 22.

This method was further applied as an exclusion metric to test whether error in the plasma-derived GFR determinations are also contributing to the data scatter in the correlation plots. FIG. 27 shows the optimization of this metric. By selecting 5% as the cut-off for acceptability of the GFRs, a slight improvement in $R^2$ and SEC was observed. However, this necessitated the exclusion of an additional 10 subjects, reducing the remaining subjects to 35. The resulting correlation plots are shown in FIGS. 23 and 24. A numerical summary of applying the different data exclusion metrics is provided in Table 4.

TABLE 4

| GFR Compound | GFR norm. method | Offset Method | Outlier Exclusion Methods | R² | N | SEC Absolute (mL/min) | SEC Relative (%) |
|---|---|---|---|---|---|---|---|
| MB-102 | BSA | Hybrid | none | 0.8278 | 55 | 13.6 | 16.8% |
| MB-102 | BSA | Hybrid | (1) | 0.8906 | 45 | 11.0 | 15.0% |
| MB-102 | BSA | Hybrid | (2) | 0.8716 | 35 | 12.0 | 14.5% |
| MB-102 | $V_d(1)$ | Hybrid | none | 0.9165 | 55 | 10.3 | 15.4% |
| MB-102 | $V_d(1)$ | Hybrid | (1) | 0.9575 | 45 | 7.4 | 14.1% |
| MB-102 | $V_d(1)$ | Hybrid | (2) | 0.9614 | 35 | 7.0 | 10.2% |
| MB-102 | $V_d(2)$ | Hybrid | none | 0.9199 | 55 | 9.4 | 14.5% |
| MB-102 | $V_d(2)$ | Hybrid | (1) | 0.9575 | 45 | 7.0 | 13.3% |
| MB-102 | $V_d(2)$ | Hybrid | (2) | 0.9597 | 35 | 7.7 | 9.6% |

Figure 10:
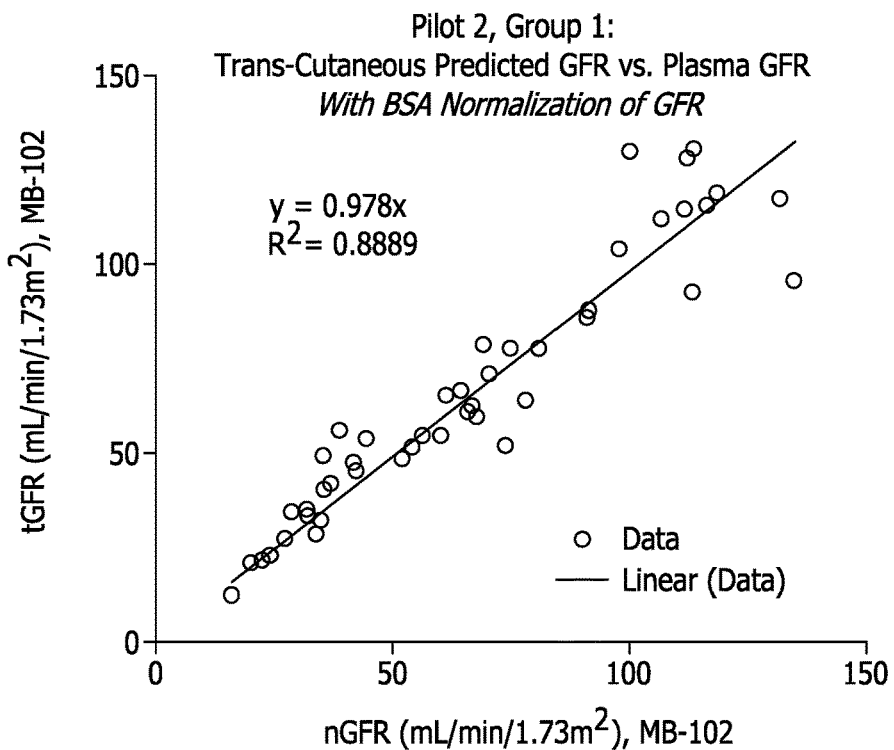
FIG. 10 is a graph correlating the transdermally predicted GFR with the plasma measured GFR determined using MB-102 and normalized to body surface area of the subject (outlier exclusion method 1; hybrid offset method).
Figure 11:
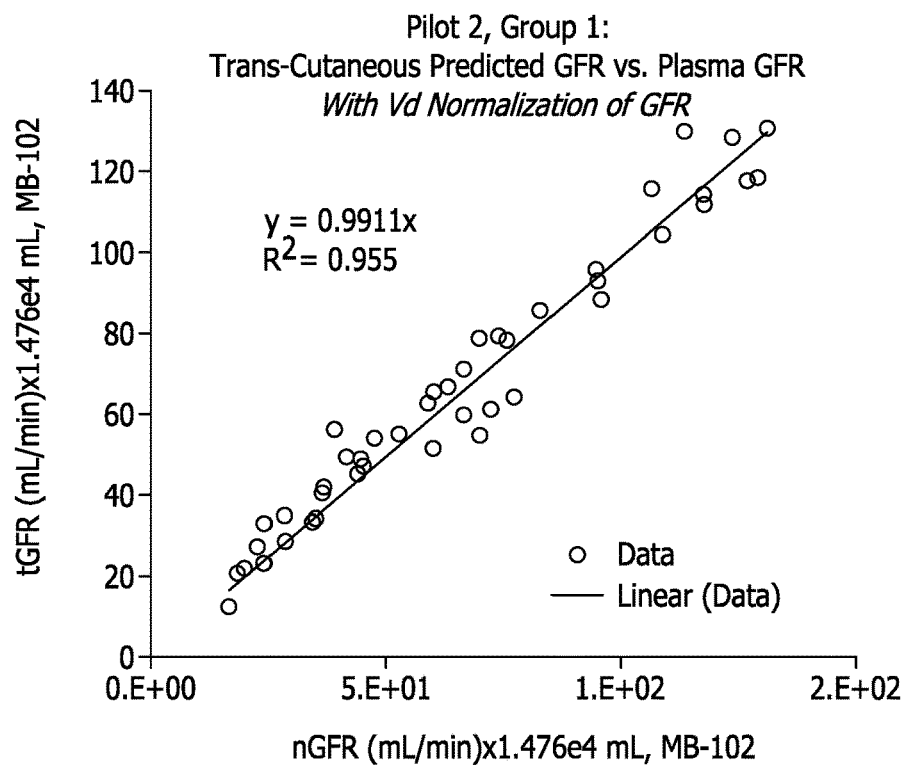
FIG. 11 is a graph correlating the transdermally predicted GFR with the plasma measured GFR determined using MB-102 and normalized to the volume of distribution of the tracer agent within the subject (outlier exclusion method 1; hybrid offset method).
Figure 12:
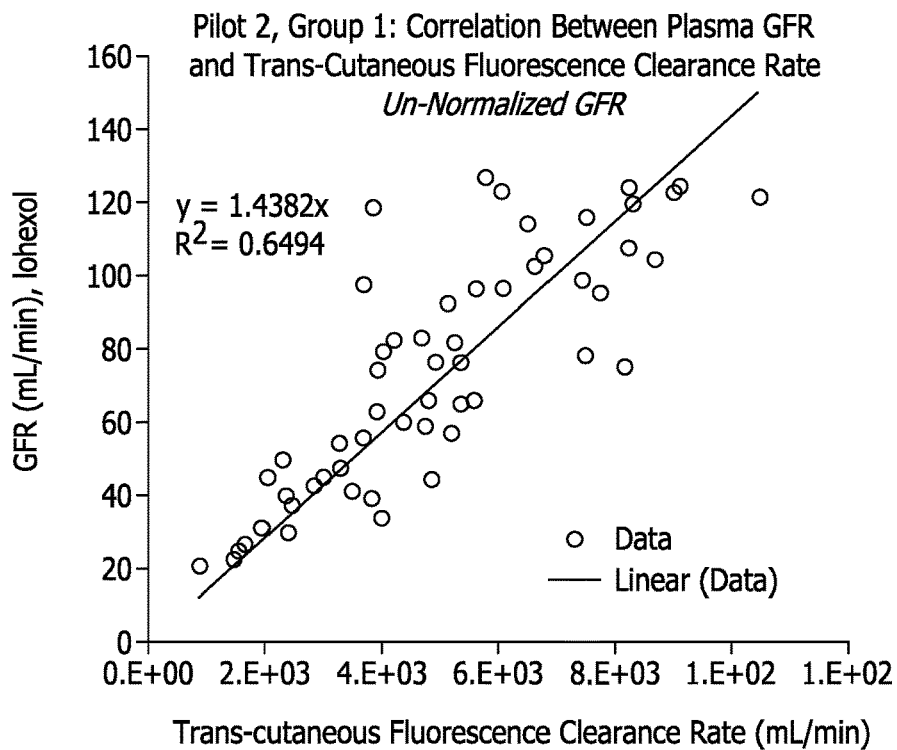
FIG. 12 is a graph correlating the plasma-determined GFR to the trans-cutaneous fluorescence clearance rate: GFR by Iohexol, Un-Normalized (No outlier exclusion; fixed offset fitting method).
Figure 13:
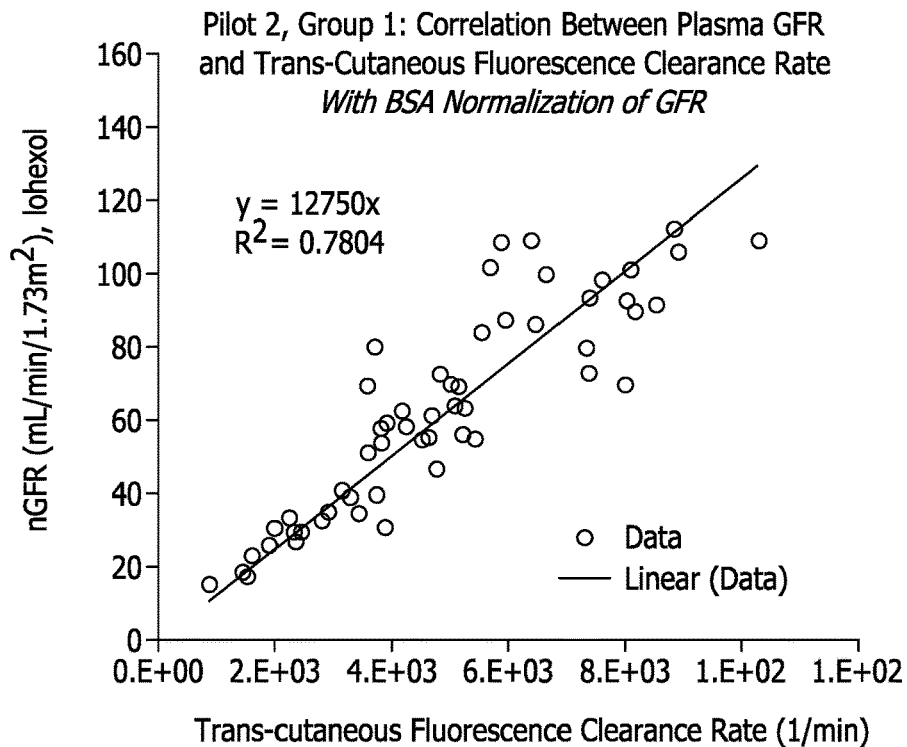
FIG. 13 is a graph correlating the plasma-determined GFR to the trans-cutaneous fluorescence clearance rate: GFR by Iohexol, BSA-Normalized (No outlier exclusion; fixed offset fitting method).
Figure 14:
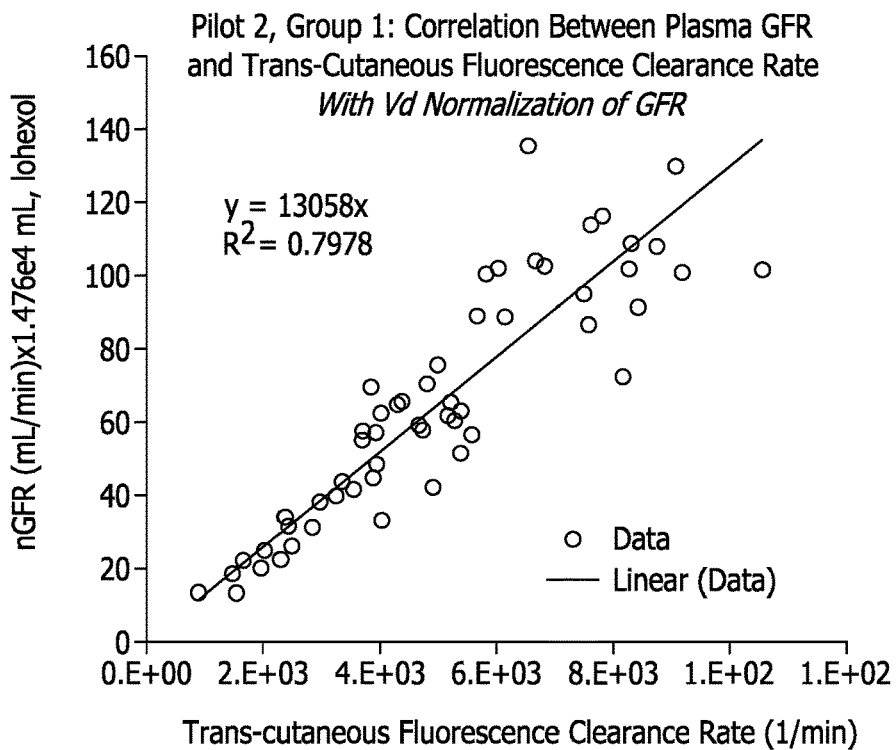
FIG. 14 is a graph correlating the plasma-determined GFR to the trans-cutaneous fluorescence clearance rate: GFR by Iohexol, $V_d$—Normalized (Method 1) (No outlier exclusion; fixed offset fitting method).
Figure 15:
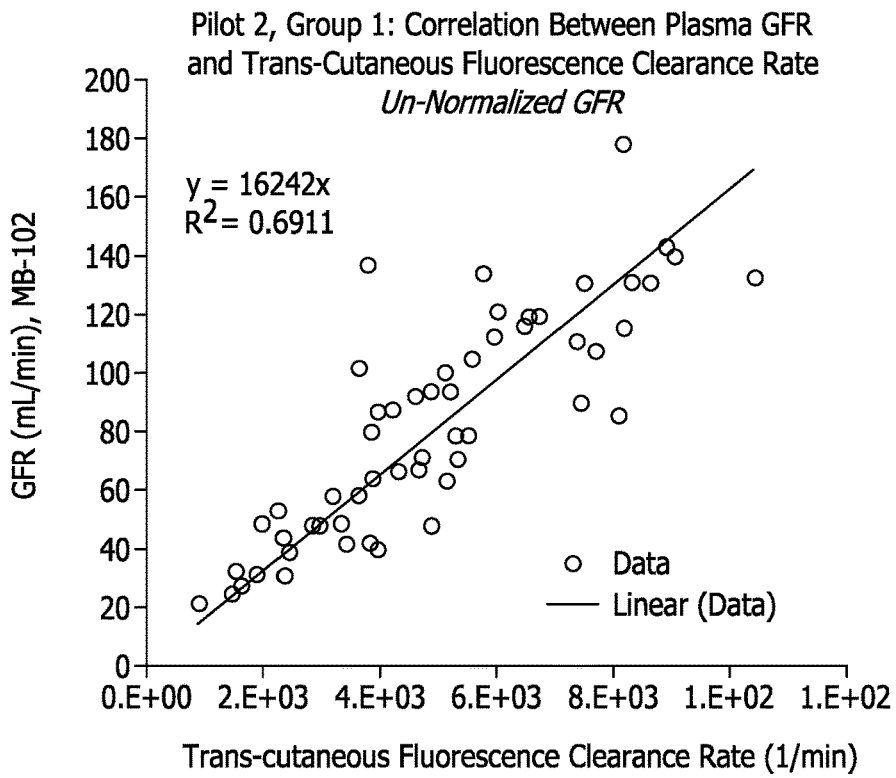
FIG. 15 is a graph correlating the plasma-determined GFR to the trans-cutaneous fluorescence clearance rate: GFR by MB-102, Un-normalized (No outlier exclusion; fixed offset fitting method).
Figure 16:
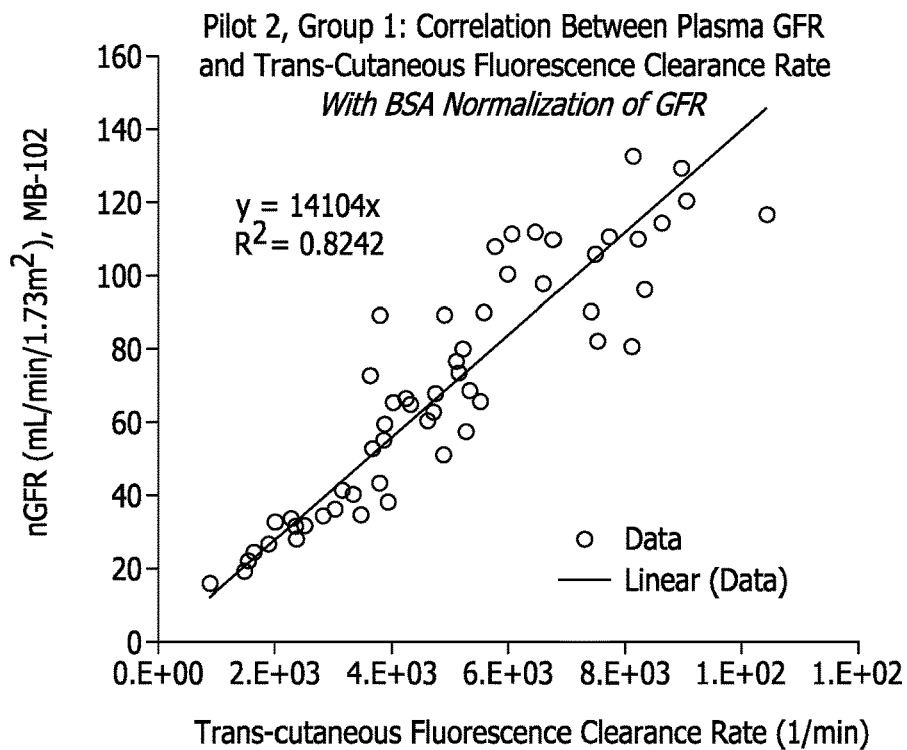
FIG. 16 is a graph correlating the plasma-determined GFR to the trans-cutaneous fluorescence clearance rate: GFR by MB-102, BSA-Normalized (No outlier exclusion; fixed offset fitting method).
Figure 17:
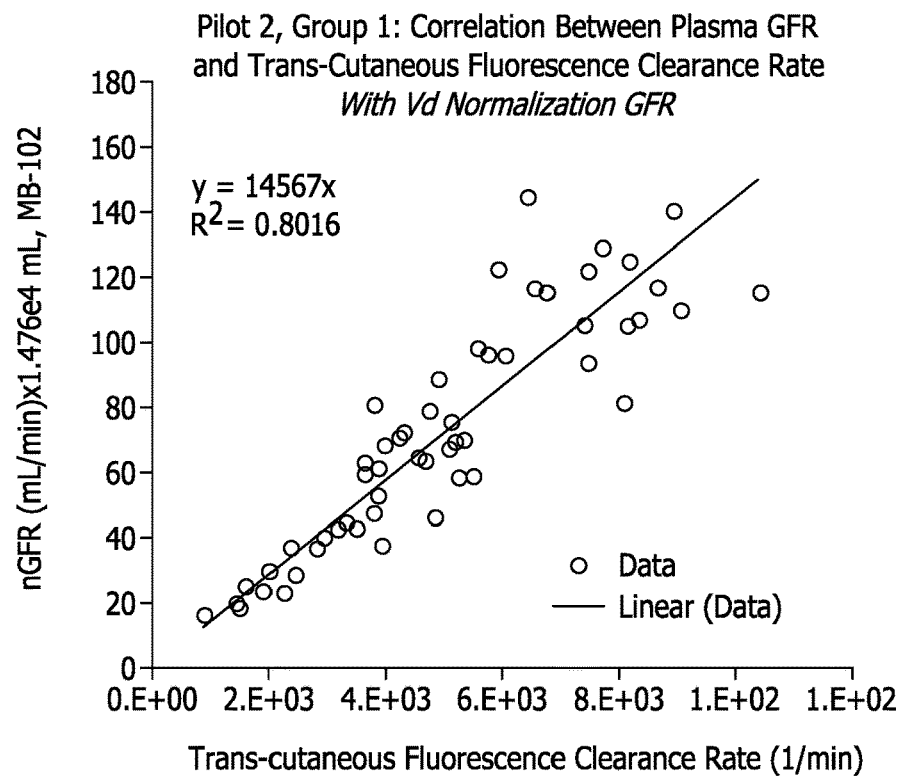
FIG. 17 is a graph correlating the plasma-determined GFR to the trans-cutaneous fluorescence clearance rate: GFR by MB-102, $V_d$—Normalized, Method 1 (No outlier exclusion; fixed offset fitting method).

The calibration slope determined from the above-described methods can be applied to generate transcutaneous measurements of body-size-corrected GFR (herein referred to as "tGFR"). FIG. 10 shows the correlation between the predicted and plasma GFR values with BSA normalization. The calibration accuracy can be depicted by plotting the tGFR against the "gold standard" determination of body-size-corrected GFR, derived from the plasma PK analysis. FIG. 10 shows the resulting correlation when the plasma-determined GFR values were normalized to patient body surface area (BSA), for which the correlation coefficient ($R^2$) is 0.89. Employing the volume of distribution ($V_d$) to correct for body size instead of BSA resulted in a substantially improved correlation of 0.96 (FIG. 11).

When compared to the most commonly used method for estimating GFR in clinical practice, eGFR, these tGFR results demonstrate a potential for substantially improved accuracy. High accuracy is important in guiding clinical decisions. FIG. 28 and Table 1 illustrate the 5 stages of chronic kidney disease (CKD). Misdiagnosis of the CKD may affect the clinical treatment course. A error grid plot was constructed to provide visualization of CKD misdiagnosis of GFR measurements relative to a gold standard, as shown in FIGS. 29a-c. Measurements falling within a box with all green borders are correctly classified by CKD stage. Measurements contained within yellow and green borders are misdiagnosed by one CKD stage. Measurements contained within red and yellow borders are misdiagnosed by two CKD stages. FIG. 29a shows the eGFR error grid for the same group of subjects as was used in the above-described analysis. In this case, 2 of the 60 subjects were misdiagnosed by 2 CKD stages, 16 subjects were misdiagnosed by 1 stage; and 41 subjects were correctly diagnosed. Table 5 provides a summary of the CKD diagnosis errors as a percent of total measurements. FIGS. 29b and c provide the error grid plots for transdermal GFR (tGFR) determination. Importantly, the tGFR error grids contain no misdiagnoses by 2 CKD stages. Further, tGFR by the $V_d$ normalization method shows a substantial reduction in 1-stage misdiagnoses, when compared to eGFR (see Table 5).

TABLE 5

| GFR Method | % of Measurements by CKD Stage Diagnosis Error | | |
|---|---|---|---|
| | 0 | ±1 | ±2 |
| eGFR | 70% | 27% | 3% |
| tGFR, BSA norm. | 71% | 29% | 0% |
| tGFR, $V_d$ norm. | 84% | 16% | 0% |

Transdermal GFR Determination (Windowed Fits)

In the above example, the full available data sets (i.e. following administration of the tracer agent and equilibration, 10 hours of fluorescence decay) were used for determining the GFR. This may be appropriate for patients with stable kidney function, but for patients with or at risk of acute kidney injury, a more rapid and real-time repeated assessment of GFR trend is needed. Even for patients with stable kidney function, waiting 12 hours for the GFR determination may be inconvenient. Tables 6 and 7 show the results of varying the Measurement Time Window and Single Injection Reporting Period for the same group of subjects as already described above.

The Measurement Time Windows (column 1 in Tables 6 and 7) were non-overlapping in this example, so that the Number of Windows (column 2 in Tables 6 and 7) multiplied by the Measurement Time Windows indicates the total number of hours after equilibration over which GFR estimates were made. The best results were obtained when the Measurement Time Window was long enough so that the fluorescence intensity decays substantially. The time needed to achieve the same fraction of fluorescence intensity decay will vary according to the health of the kidney. Therefore, the offset was fixed at zero, except for the widest Measurement Time Windows on subjects with healthy kidneys. The Standard Error of Calibration is summarized for all subjects (column 5 in Tables 6 and 7), as well as for subsets of subjects with nGFR below or above 75 mL/min.

Using BSA normalized GFR as the reference comparison (Table 6), for subjects with nGFR above 75, a Measurement Time Window of at least about 1.5 hours was used in order to achieve an nGFR calibration accuracy below 15 mL/min. For subjects with nGFR below 75, a Measurement Time Window of least about 3 hours was used in order to achieve nGFR calibration accuracy below 10 mL/min. Using $V_d$ normalized GFR as the reference comparison (Table 7), equivalent nGFR calibration accuracy were achieved with Measurement Time Windows of 0.5 hours and 2 hours, respectively. As can be seen in Tables 6 and 7, the calibration accuracy targets stated above were maintained across at least 2 non-overlapping Measurement Time Windows. However, a significant increase in the SEC was typically observed when the predictions were extended across 3 or 4 Measurement Time Windows. By increasing (e.g. doubling or tripling) the Measurement Window Time from that used for the first two GFR measurements, at least a third GFR measurement provided equivalent accuracy. These results show the utility of providing an automatically adjusting Measurement Time Window, not just for accounting for differing SNR across different patients, but also to account for the diminishing SNR over time, as the tracer agent is progressively cleared by the kidneys.

TABLE 6

| Meas. Window (hrs) | Num. Win-dows | Offset Method | N | SEC (mL/min/1.73 m²) | | |
|---|---|---|---|---|---|---|
| | | | | All | nGFR < 75 | nGFR ≥ 75 |
| 0.5 | 1 | Fixed | 44 | 18.8 | 19.0 | 18.2 |
| 0.5 | 2 | Fixed | 44 | 20.8 | 21.0 | 20.2 |
| 0.5 | 3 | Fixed | 44 | 21.0 | 20.8 | 21.5 |
| 0.5 | 4 | Fixed | 44 | 23.4 | 20.9 | 27.5 |
| 1 | 1 | Fixed | 44 | 16.0 | 16.4 | 15.1 |
| 1 | 2 | Fixed | 44 | 17.3 | 16.0 | 19.6 |
| 1 | 3 | Fixed | 44 | 17.4 | 16.2 | 19.5 |
| 1 | 4 | Fixed | 44 | 19.5 | 16.1 | 24.8 |
| 1.5 | 1 | Fixed | 45 | 12.0 | 11.2 | 13.3 |
| 1.5 | 2 | Fixed | 45 | 12.9 | 11.8 | 14.7 |
| 1.5 | 3 | Fixed | 45 | 17.4 | 12.4 | 24.0 |
| 1.5 | 4 | Fixed | 45 | 23.7 | 12.6 | 35.9 |
| 1.5 | 5 | Fixed | 45 | 28.5 | 18.3 | 41.1 |
| 1.5 | 6 | Fixed | 45 | 41.0 | 20.4 | 63.0 |
| 2 | 1 | Fixed | 45 | 11.4 | 10.3 | 13.0 |
| 2 | 2 | Fixed | 45 | 13.7 | 11.6 | 16.8 |
| 2 | 3 | Fixed | 45 | 21.1 | 12.1 | 31.4 |
| 2 | 4 | Fixed | 45 | 28.2 | 19.2 | 39.7 |
| 3 | 1 | Fixed | 45 | 10.7 | 9.4 | 12.7 |
| 3 | 2 | Fixed | 45 | 19.2 | 9.9 | 29.2 |
| 3 | 3 | Fixed | 45 | 29.6 | 16.5 | 44.4 |
| 4 | 1 | Fixed | 45 | 10.6 | 9.3 | 12.5 |
| 4 | 2 | Fixed | 45 | 53.3 | 11.4 | 88.0 |
| 5 | 1 | Fixed | 45 | 10.6 | 8.4 | 13.6 |
| 5 | 2 | Fixed | 45 | 19.5 | 15.6 | 25.2 |
| 5 | 1 | Variable | 45 | 24.9 | 28.2 | 17.3 |
| 5 | 1 | Hybrid | 45 | 13.9 | 11.6 | 17.3 |
| 5 | 2 | Hybrid | 45 | 20.2 | 14.6 | 27.6 |
| 10 | 1 | Fixed | 45 | 11.6 | 8.1 | 16.0 |
| 10 | 1 | Variable | 45 | 15.4 | 14.9 | 16.3 |
| 10 | 1 | Hybrid | 45 | 11.1 | 6.8 | 16.3 |

TABLE 7

| Window Length (hrs) | Num. Win-dows | Offset Method | N | SEC (mL/min/1.476e4 mL) | | |
|---|---|---|---|---|---|---|
| | | | | All | nGFR < 75 | nGFR ≥ 75 |
| 0.5 | 1 | Fixed | 44 | 17.4 | 19.5 | 11.5 |
| 0.5 | 2 | Fixed | 44 | 20.2 | 22.7 | 12.8 |
| 0.5 | 3 | Fixed | 44 | 20.4 | 21.9 | 16.8 |
| 0.5 | 4 | Fixed | 44 | 22.1 | 21.8 | 22.8 |
| 1 | 1 | Fixed | 44 | 14.9 | 16.7 | 10.3 |
| 1 | 2 | Fixed | 44 | 15.6 | 15.6 | 15.4 |
| 1 | 3 | Fixed | 44 | 16.8 | 15.8 | 18.8 |
| 1 | 4 | Fixed | 44 | 19.5 | 15.7 | 25.8 |
| 1.5 | 1 | Fixed | 45 | 10.4 | 11.5 | 8.0 |
| 1.5 | 2 | Fixed | 45 | 12.6 | 12.1 | 13.6 |
| 1.5 | 3 | Fixed | 45 | 17.2 | 12.6 | 24.0 |
| 1.5 | 4 | Fixed | 45 | 25.4 | 13.3 | 39.8 |
| 1.5 | 5 | Fixed | 45 | 29.7 | 18.8 | 44.1 |
| 1.5 | 6 | Fixed | 45 | 41.1 | 20.7 | 65.0 |
| 2 | 1 | Fixed | 45 | 8.9 | 9.6 | 7.5 |
| 2 | 2 | Fixed | 45 | 14.0 | 10.8 | 18.9 |
| 2 | 3 | Fixed | 45 | 22.3 | 12.5 | 34.3 |
| 2 | 4 | Fixed | 45 | 30.7 | 20.2 | 44.9 |
| 3 | 1 | Fixed | 45 | 8.9 | 8.8 | 9.1 |
| 3 | 2 | Fixed | 45 | 19.1 | 10.6 | 29.5 |
| 3 | 3 | Fixed | 45 | 32.3 | 17.9 | 50.0 |
| 4 | 1 | Fixed | 45 | 9.5 | 8.6 | 11.1 |
| 4 | 2 | Fixed | 45 | 53.4 | 12.4 | 90.9 |
| 5 | 1 | Fixed | 45 | 9.8 | 8.0 | 12.7 |
| 5 | 2 | Fixed | 45 | 20.8 | 16.7 | 27.3 |
| 5 | 1 | Variable | 45 | 23.2 | 27.3 | 11.5 |
| 5 | 1 | Hybrid | 45 | 11.0 | 10.8 | 11.5 |
| 5 | 2 | Hybrid | 45 | 19.1 | 13.8 | 26.8 |
| 10 | 1 | Fixed | 45 | 12.4 | 9.0 | 17.3 |
| 10 | 1 | Variable | 45 | 11.6 | 13.0 | 7.9 |
| 10 | 1 | Hybrid | 45 | 7.0 | 6.6 | 7.9 |

Real-Time Transdermal GFR Measurement

The methods disclosed herein enable real-time transdermal GFR determination in patients. After intravascular injection of the tracer agent into the subject, a waiting period of two hours was used to allow for equilibration of the tracer agent into the extravascular space. After the two hour mark data was accumulated for one more hour before performing a first fit to the RDTC. The first RDTC fit was performed with the offset term fixed at zero. If the RDTC was less than 3.5 hours the fit was repeated, allowing the slope to vary, otherwise the original RDTC (with fixed offset) was retained. The estimated error of the RDTC was then divided by the RDTC. If the resulting relative error was less than 1.7%, the RDTC was converted into BSA-normalized GFR by inverting the RDTC and multiplying by the slope shown in FIG. 23; otherwise the GFR was not reported. After the first RDTC fit, the fitting procedure was repeated at approximately 3 second intervals, with the subsequent fits incorporating all of the data that was in the first fit as well as all data that had been subsequently accumulated (at time intervals of about one second). The same procedure was applied to the data collected by two sensors: one placed over the manubrium of the sternum, and the second placed over the pectoralis major. The results generated in real-time during the measurement are displayed in FIG. 30. Over the full course of the study, the agreement between the tGFR reported by the two sensors and the variation in the tGFR reported by each sensor was within 2 mL/min/1.73 m².

Stability Testing of MB-102

Samples of MB-102 were prepared and stored at 25° C. and 60% relative humidity for 24 months. HPLC evaluation of each sample was performed at various time points to assess the stability of the samples. The results are shown in Table 8.

TABLE 8

| Months | Purity |
|---|---|
| 0 | >99% |
| 6 | >99% |
| 12 | 98.9% |
| 18 | 98.3% |
| 24 | 97.8% |

When introducing elements of the present disclosure or embodiments thereof, the articles "a," "an," "the," and "said" are intended to mean that there are one or more of the elements. The terms "comprising," including," and "having" are intended to be inclusive and mean that there may be additional elements other than the listed elements.

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

What is claimed is:

1. A method for determining a glomerular filtration rate (GFR) in a patient in need thereof, said method comprising:
   administering to said patient a compound of Formula I, or a pharmaceutically acceptable salt thereof,
   measuring a concentration of the compound of Formula I in said patient over a measurement time window, wherein the compound of Formula I is configured to emit spectral energy when exposed to electromagnetic radiation, and wherein measuring the concentration of the compound of Formula I comprises transdermally measuring the spectral energy emitted from by the compound of Formula I in said patient over the measurement time window, and determining the GFR in said patient based on the measured concentration of the compound of Formula I over the measurement time window;

wherein in the compound of Formula I,

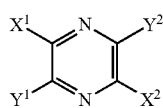

Formula I each of $X^1$ and $X^2$ is independently —$CO_2R^1$, —$CONR^1R^2$, —CO(AA) or —CONH(PS);

each of $Y^1$ and $Y^2$ is independently selected from the group consisting of —$NR^1R^2$ and

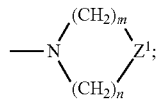

$Z^1$ is a single bond, —$CR^1R^2$—, —O—, —$NR^1$—, —$NCOR^1$—, —S—, —SO—, or —$SO_2$—;

each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_a$ $CO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_a NHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$;

AA is a single amino acid or a peptide chain comprising two or more amino acids, each amino acid selected from the group consisting of natural and unnatural amino acids, wherein the two or more amino acids of the peptide chain are linked together by peptide or amide bonds and each instance of AA may be the same or different than each other instance;

PS is a sulfated or non-sulfated polysaccharide chain comprising one or more monosaccharide units connected by glycosidic linkages;

a is a number from 1 to 10, c is a number from 1 to 100, and each of m and n are independently a number from 1 to 3; and wherein said patient in need thereof is a human and has at least stage 1 CKD;

wherein transdermally measuring the spectral energy comprises:

attaching a sensor on a body of said patient, the body comprising skin, wherein said sensor is configured to generate and deliver electromagnetic radiation to the compound of Formula I, and detect the spectral energy emitted by the compound of Formula I; and wherein the method is performed using a system that includes the compound of Formula I, the sensor, and a computing device communicatively coupled to the sensor, wherein the computing device determines the GFR by correlating a decrease in the spectral energy emitted by the compound of Formula I over the measurement time window to the GFR of said patient and by calculating a decay parameter associated with renal clearance over the measurement time window, wherein the decay parameter is a rate constant that is directly related to the GFR normalized to a body size metric of the patient, and wherein the rate constant is determined by fitting an exponential function to the spectral energy as a function of time or a linear function to the log of the spectral energy as a function of time.

2. The method of claim 1, wherein the measurement time window is from about 12 to about 48 hours.

3. The method of claim 1, wherein the compound of Formula I is combined with at least one pharmaceutically acceptable excipient selected from the group consisting of antibacterial agents, antioxidants, buffering agents, osmolarity adjusting agents, pH adjusting agents, preservatives, solvents, stabilizing agents, surfactants, tonicity modifying agents, viscosity adjusting agents, and combinations thereof.

4. The method of claim 3, wherein one of the at least one pharmaceutically acceptable excipients is phosphate buffered saline.

5. The method of claim 1, wherein the compound of Formula I is administered to said patient via enteral, intravenous, oral, parenteral, subcutaneous, or transdermal administration.

6. The method of claim 1, wherein at least one of $X^1$ and $X^2$ is —CO(PS) or —CO(AA).

7. The method of claim 1, wherein both $X^1$ and $X^2$ are —CO(AA).

8. The method of claim 7, wherein each instance of AA is one or more of D-a-amino acids.

9. The method of claim 7, wherein each instance of AA is a single D-a-amino acid.

10. The method of claim 7, wherein AA is selected from the group consisting of D-alanine, D-arginine, D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tyrosine, D-tryptophan and D-valine.

11. The method of claim 7, wherein AA is selected from the group consisting of D-arginine, D-asparagine, D-aspartic acid, D-glutamic acid, D-glutamine, glycine, D-histidine, D-homoserine, D-lysine, and D-serine.

12. The method of claim 7, wherein AA is selected from the group consisting of D-aspartic acid and D-serine.

13. The method of claim 9, wherein AA is D-serine.

14. The method of claim 9, wherein AA is D-serine, $Y^1$ and $Y^2$ are each —$NR^1R^2$ and $R^1=R^2=H$.

15. The method of claim 1, wherein the administering is done via intravenous or transdermal administration.

16. The method of claim 15, wherein the administering is done via single injection.

17. The method of claim 16, wherein the measuring is done via multiple measurements after the single injection, whereby determining the GFR is performed in real time.

18. The method of claim 1, further comprising measuring a diffuse reflectance of the skin prior to and/or after administering the compound of Formula I.

19. The method of claim 1, further comprising recording a baseline signal of fluorescence prior to administering the compound of Formula I.

20. The method of claim 1, further comprising monitoring equilibration of the compound of Formula I after administering the compound of Formula I.

21. The method of claim 20, wherein monitoring equilibration of the compound of Formula I comprises fitting a change in fluorescence intensity over time to a single exponential function and deeming the equilibration complete once the fitted time constant is stable.

22. The method of claim 1, wherein the body size metric is body surface area.

23. The method of claim 1, wherein the body size metric is the volume of distribution of the compound of Formula I.

24. A method for determining a glomerular filtration rate (GFR) in a patient in need thereof, said method comprising:
administering to said patient a compound of Formula I, or a pharmaceutically acceptable salt thereof,
measuring a concentration of the compound of Formula I in said patient over a measurement time window, wherein the compound of Formula I is configured to emit spectral energy when exposed to electromagnetic radiation, and wherein measuring the concentration of the compound of Formula I comprises transdermally measuring the spectral energy emitted from by the compound of Formula I in said patient over the measurement time window, and
determining the GFR in said patient based on the measured concentration of the compound of Formula I over the measurement time window;
wherein in the compound of Formula I,

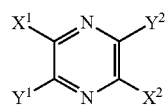

Formula I each of $X^1$ and $X^2$ is independently —$CO_2R^1$, —$CONR^1R^2$, —CO(AA) or —CONH(PS);
each of $Y^1$ and $Y^2$ is independently selected from the group consisting of —$NR^1R^2$ and

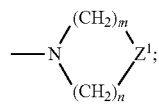

$Z^1$ is a single bond, —$CR^1R^2$—, —O—, —$NR^1$—, —$NCOR^1$—, —S—, —SO—, or —$SO_2$—;
each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_a$ $CO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_a$ $NHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$;
AA is a single amino acid or a peptide chain comprising two or more amino acids, each amino acid selected from the group consisting of natural and unnatural amino acids, wherein the two or more amino acids of the peptide chain are linked together by peptide or amide bonds and each instance of AA may be the same or different than each other instance;
PS is a sulfated or non-sulfated polysaccharide chain comprising one or more monosaccharide units connected by glycosidic linkages;
a is a number from 1 to 10, c is a number from 1 to 100, and each of m and n are independently a number from 1 to 3; and
wherein said patient in need thereof is a human;
wherein transdermally measuring the spectral energy comprises:
attaching a sensor on a body of said patient, the body comprising skin, wherein said sensor is configured to generate and deliver electromagnetic radiation to the compound of Formula I, and detect the spectral energy emitted by the compound of Formula I; and
wherein the method is performed using a system that includes the compound of Formula I, the sensor, and a computing device communicatively coupled to the sensor, wherein the computing device determines the GFR by correlating a decrease in the spectral energy emitted by the compound of Formula I over the measurement time window to the GFR of said patient and by calculating a decay parameter associated with renal clearance over the measurement time window, wherein the decay parameter is a rate constant that is directly related to the GFR normalized to a body size metric of the patient, and wherein the rate constant is determined by fitting an exponential function to the spectral energy as a function of time or a linear function to the log of the spectral energy as a function of time.

25. The method of claim 24, wherein the measurement time window is from about 12 to about 48 hours.

26. The method of claim 24, wherein the compound of Formula I is combined with at least one pharmaceutically acceptable excipient selected from the group consisting of antibacterial agents, antioxidants, buffering agents, osmolarity adjusting agents, pH adjusting agents, preservatives, solvents, stabilizing agents, surfactants, tonicity modifying agents, viscosity adjusting agents, and combinations thereof.

27. The method of claim 26, wherein one of the at least one pharmaceutically acceptable excipients is phosphate buffered saline.

28. The method of claim 24, wherein the compound of Formula I is administered to said patient via enteral, intravenous, oral, parenteral, subcutaneous, or transdermal administration.

29. The method of claim 24, wherein both $X^1$ and $X^2$ are —CO(AA).

30. The method of claim 29, wherein AA is D-serine, $Y^1$ and $Y^2$ are each —$NR^1R^2$ and $R^1=R^2=H$.

31. The method of claim 24, wherein the administering is done via intravenous or transdermal administration.

32. The method of claim 31, wherein the administering is done via single injection.

33. The method of claim 32, wherein the measuring is done via multiple measurements after the single injection, whereby determining the GFR is performed in real time.

34. The method of claim 24, further comprising measuring a diffuse reflectance of the skin prior to and/or after administering the compound of Formula I.

35. The method of claim 24, further comprising recording a baseline signal of fluorescence prior to administering the compound of Formula I.

36. The method of claim 24, further comprising monitoring equilibration of the compound of Formula I after administering the compound of Formula I.

37. The method of claim 36, wherein monitoring equilibration of the compound of Formula I comprises fitting a change in fluorescence intensity over time to a single exponential function and deeming the equilibration complete once the fitted time constant is stable.

38. The method of claim 24, wherein the body size metric is body surface area.

* * * * *